(12) United States Patent
Taylor et al.

(10) Patent No.: US 10,653,820 B2
(45) Date of Patent: *May 19, 2020

(54) COATED STENTS

(71) Applicant: Micell Technologies, Inc., Durham, NC (US)

(72) Inventors: Charles Douglas Taylor, Franklinton, NC (US); James B. McClain, Ocracoke, NC (US)

(73) Assignee: Micell Technologies, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/960,836

(22) Filed: Apr. 24, 2018

(65) Prior Publication Data

US 2018/0272043 A1 Sep. 27, 2018

Related U.S. Application Data

(63) Continuation of application No. 12/751,902, filed on Mar. 31, 2010, now Pat. No. 9,981,072.

(60) Provisional application No. 61/243,955, filed on Sep. 18, 2009, provisional application No. 61/212,964, filed on Apr. 17, 2009, provisional application No. 61/165,880, filed on Apr. 1, 2009.

(51) Int. Cl.
  *A61F 2/82* (2013.01)
  *A61L 31/10* (2006.01)
  *A61L 31/16* (2006.01)

(52) U.S. Cl.
  CPC ............. *A61L 31/10* (2013.01); *A61L 31/16* (2013.01); *A61F 2/82* (2013.01); *A61F 2210/0004* (2013.01); *A61F 2250/0067* (2013.01)

(58) Field of Classification Search
  CPC ........................................ A61F 2/82
  See application file for complete search history.

(56) References Cited

U.S. PATENT DOCUMENTS

| | | |
|---|---|---|
| 3,087,860 A | 4/1963 | Endicott et al. |
| 3,123,077 A | 3/1964 | Alcamo |
| 3,457,280 A | 7/1969 | Schmitt et al. |
| 3,597,449 A | 8/1971 | Deprospero et al. |
| 3,737,337 A | 6/1973 | Schnoring et al. |
| 3,773,919 A | 11/1973 | Boswell et al. |
| 3,929,992 A | 12/1975 | Sehgal et al. |
| 4,000,137 A | 12/1976 | Dvonch et al. |

(Continued)

FOREIGN PATENT DOCUMENTS

| | | |
|---|---|---|
| CA | 2237466 A1 | 11/1998 |
| CA | 2589761 A1 | 6/2006 |

(Continued)

OTHER PUBLICATIONS

PCT/EP01/05736 International Preliminary Examination Report dated Jan. 14, 2002.

(Continued)

*Primary Examiner* — Matthew W Schall
(74) *Attorney, Agent, or Firm* — Lerner, David, Littenberg, Krumholz & Mentlik, LLP

(57) ABSTRACT

Provided herein is a coated coronary stent, comprising: a. stent; b. a plurality of layers deposited on said stent to form said coronary stent; wherein at least one of said layers comprises a bioabsorbable polymer and at least one of said layers comprises one or more active agents; wherein at least part of the active agent is in crystalline form.

20 Claims, 5 Drawing Sheets

(56) References Cited

U.S. PATENT DOCUMENTS

| | | |
|---|---|---|
| 4,188,373 A | 2/1980 | Krezanoski |
| 4,285,987 A | 8/1981 | Ayer et al. |
| 4,326,532 A | 4/1982 | Hammar |
| 4,336,381 A | 6/1982 | Nagata et al. |
| 4,389,330 A | 6/1983 | Tice et al. |
| 4,474,572 A | 10/1984 | McNaughton et al. |
| 4,474,751 A | 10/1984 | Haslam et al. |
| 4,478,822 A | 10/1984 | Haslam et al. |
| 4,530,840 A | 7/1985 | Tice et al. |
| 4,582,731 A | 4/1986 | Smith |
| 4,606,347 A | 8/1986 | Fogarty et al. |
| 4,617,751 A | 10/1986 | Johansson |
| 4,655,771 A | 4/1987 | Wallsten |
| 4,675,189 A | 6/1987 | Kent et al. |
| 4,733,665 A | 3/1988 | Palmaz |
| 4,734,227 A | 3/1988 | Smith |
| 4,734,451 A | 3/1988 | Smith |
| 4,758,435 A | 7/1988 | Schaaf |
| 4,762,593 A | 8/1988 | Youngner |
| 4,931,037 A | 6/1990 | Wetterman |
| 4,950,239 A | 8/1990 | Gahara et al. |
| 4,985,625 A | 1/1991 | Hurst |
| 5,000,519 A | 3/1991 | Moore |
| 5,090,419 A | 2/1992 | Palestrant |
| 5,096,848 A | 3/1992 | Kawamura |
| 5,102,417 A | 4/1992 | Palmaz |
| 5,104,404 A | 4/1992 | Wolff |
| 5,106,650 A | 4/1992 | Hoy et al. |
| 5,125,570 A | 6/1992 | Jones |
| 5,158,986 A | 10/1992 | Cha et al. |
| 5,185,776 A | 2/1993 | Townsend |
| 5,195,969 A | 3/1993 | Wang et al. |
| 5,243,023 A | 9/1993 | Dezern |
| 5,270,086 A | 12/1993 | Hamlin |
| 5,288,711 A | 2/1994 | Mitchell et al. |
| 5,320,634 A | 6/1994 | Vigil et al. |
| 5,324,049 A | 6/1994 | Mistrater et al. |
| 5,340,614 A | 8/1994 | Perman et al. |
| 5,342,621 A | 8/1994 | Eury |
| 5,350,361 A | 9/1994 | Tsukashima et al. |
| 5,350,627 A | 9/1994 | Nemphos et al. |
| 5,356,433 A | 10/1994 | Rowland et al. |
| 5,360,403 A | 11/1994 | Mische |
| 5,362,718 A | 11/1994 | Skotnicki et al. |
| 5,366,504 A | 11/1994 | Andersen et al. |
| 5,368,045 A | 11/1994 | Clement et al. |
| 5,372,676 A | 12/1994 | Lowe |
| 5,385,776 A | 1/1995 | Maxfield et al. |
| 5,387,313 A | 2/1995 | Thorns |
| 5,403,347 A | 4/1995 | Roby et al. |
| 5,470,603 A | 11/1995 | Staniforth et al. |
| 5,494,620 A | 2/1996 | Liu et al. |
| 5,500,180 A | 3/1996 | Anderson et al. |
| 5,514,379 A | 5/1996 | Weissleder et al. |
| 5,545,208 A | 8/1996 | Wolff et al. |
| 5,556,383 A | 9/1996 | Wang et al. |
| 5,562,922 A | 10/1996 | Lambert |
| 5,569,463 A | 10/1996 | Helmus et al. |
| 5,570,537 A | 11/1996 | Black et al. |
| 5,578,709 A | 11/1996 | Woiszwillo |
| 5,599,576 A | 2/1997 | Opolski |
| 5,605,696 A | 2/1997 | Eury et al. |
| 5,607,442 A | 3/1997 | Fischell et al. |
| 5,609,629 A | 3/1997 | Fearnot et al. |
| 5,626,611 A | 5/1997 | Liu et al. |
| 5,626,862 A | 5/1997 | Brem et al. |
| 5,632,772 A | 5/1997 | Alcime et al. |
| 5,669,932 A | 9/1997 | Fischell et al. |
| 5,674,192 A | 10/1997 | Sahatjian et al. |
| 5,674,242 A | 10/1997 | Phan et al. |
| 5,674,286 A | 10/1997 | D'Alessio et al. |
| 5,725,570 A | 3/1998 | Heath |
| 5,733,303 A | 3/1998 | Israel et al. |
| 5,766,158 A | 6/1998 | Opolski |
| 5,800,511 A | 9/1998 | Mayer |
| 5,807,404 A | 9/1998 | Richter |
| 5,811,032 A | 9/1998 | Kawai et al. |
| 5,824,049 A | 10/1998 | Ragheb et al. |
| 5,837,313 A | 11/1998 | Ding et al. |
| 5,843,120 A | 12/1998 | Israel et al. |
| 5,871,436 A | 2/1999 | Eury |
| 5,873,904 A | 2/1999 | Ragheb et al. |
| 5,876,426 A | 3/1999 | Kume et al. |
| 5,876,452 A | 3/1999 | Athanasiou et al. |
| 5,913,895 A | 6/1999 | Burpee et al. |
| 5,924,631 A | 7/1999 | Rodrigues et al. |
| 5,948,020 A | 9/1999 | Yoon et al. |
| 5,957,975 A | 9/1999 | Lafont et al. |
| 5,981,568 A | 11/1999 | Kunz et al. |
| 5,981,719 A | 11/1999 | Woiszwillo et al. |
| 6,013,855 A | 1/2000 | McPherson et al. |
| 6,036,978 A | 3/2000 | Gombotz et al. |
| 6,039,721 A | 3/2000 | Johnson et al. |
| 6,068,656 A | 5/2000 | Von Oepen |
| 6,071,308 A | 6/2000 | Ballou et al. |
| 6,077,880 A | 6/2000 | Castillo et al. |
| 6,090,925 A | 7/2000 | Woiszwillo et al. |
| 6,099,562 A | 8/2000 | Ding et al. |
| 6,129,755 A | 10/2000 | Mathis et al. |
| 6,143,037 A | 11/2000 | Goldstein et al. |
| 6,143,314 A | 11/2000 | Chandrashekar et al. |
| 6,146,356 A | 11/2000 | Wang et al. |
| 6,146,404 A | 11/2000 | Kim et al. |
| 6,147,135 A | 11/2000 | Yuan et al. |
| 6,153,252 A | 11/2000 | Hossainy et al. |
| 6,171,327 B1 | 1/2001 | Daniel et al. |
| 6,190,699 B1 | 2/2001 | Luzzi et al. |
| 6,193,744 B1 | 2/2001 | Ehr et al. |
| 6,206,914 B1 | 3/2001 | Soykan et al. |
| 6,217,608 B1 | 4/2001 | Penn et al. |
| 6,231,599 B1 | 5/2001 | Ley |
| 6,231,600 B1 | 5/2001 | Zhong |
| 6,245,104 B1 | 6/2001 | Alt |
| 6,248,127 B1 | 6/2001 | Shah et al. |
| 6,248,129 B1 | 6/2001 | Froix |
| 6,251,980 B1 | 6/2001 | Lan et al. |
| 6,268,053 B1 | 7/2001 | Woiszwillo et al. |
| 6,273,913 B1 | 8/2001 | Wright et al. |
| 6,284,758 B1 | 9/2001 | Egi et al. |
| 6,299,635 B1 | 10/2001 | Frantzen |
| 6,309,669 B1 | 10/2001 | Setterstrom et al. |
| 6,319,541 B1 | 11/2001 | Pletcher et al. |
| 6,325,821 B1 | 12/2001 | Gaschino et al. |
| 6,336,934 B1 | 1/2002 | Gilson et al. |
| 6,342,062 B1 | 1/2002 | Suon et al. |
| 6,344,055 B1 | 2/2002 | Shukov |
| 6,355,691 B1 | 3/2002 | Goodman |
| 6,358,556 B1 | 3/2002 | Ding et al. |
| 6,361,819 B1 | 3/2002 | Tedeschi et al. |
| 6,362,718 B1 | 3/2002 | Patrick et al. |
| 6,364,903 B2 | 4/2002 | Tseng et al. |
| 6,368,658 B1 | 4/2002 | Schwarz et al. |
| 6,372,246 B1 | 4/2002 | Wei et al. |
| 6,387,121 B1 | 5/2002 | Alt |
| 6,409,716 B1 | 6/2002 | Sahatjian et al. |
| 6,414,050 B1 | 7/2002 | Howdle et al. |
| 6,416,779 B1 | 7/2002 | D'Augustine et al. |
| 6,448,315 B1 | 9/2002 | Lidgren et al. |
| 6,458,387 B1 | 10/2002 | Scott et al. |
| 6,461,380 B1 | 10/2002 | Cox |
| 6,461,644 B1 | 10/2002 | Jackson et al. |
| 6,488,703 B1 | 12/2002 | Kveen et al. |
| 6,495,163 B1 | 12/2002 | Jordan |
| 6,497,729 B1 | 12/2002 | Moussy et al. |
| 6,506,213 B1 | 1/2003 | Mandel et al. |
| 6,511,748 B1 | 1/2003 | Barrows |
| 6,517,860 B1 | 2/2003 | Roser et al. |
| 6,521,258 B1 | 2/2003 | Mandel et al. |
| 6,524,698 B1 | 2/2003 | Schmoock |
| 6,530,951 B1 | 3/2003 | Bates et al. |
| 6,537,310 B1 | 3/2003 | Palmaz et al. |
| 6,541,033 B1 | 4/2003 | Shah |
| 6,572,813 B1 | 6/2003 | Zhang et al. |
| 6,602,281 B1 | 8/2003 | Klein |

(56) References Cited

U.S. PATENT DOCUMENTS

| | | |
|---|---|---|
| 6,610,013 B1 | 8/2003 | Fenster et al. |
| 6,627,246 B2 | 9/2003 | Mehta et al. |
| 6,649,627 B1 | 11/2003 | Cecchi et al. |
| 6,660,176 B2 | 12/2003 | Tepper et al. |
| 6,669,785 B2 | 12/2003 | DeYoung et al. |
| 6,669,980 B2 | 12/2003 | Hansen |
| 6,670,407 B2 | 12/2003 | Howdle et al. |
| 6,682,757 B1 | 1/2004 | Wright |
| 6,706,283 B1 | 3/2004 | Appel et al. |
| 6,710,059 B1 | 3/2004 | Labrie et al. |
| 6,720,003 B2 | 4/2004 | Chen et al. |
| 6,723,913 B1 | 4/2004 | Barbetta |
| 6,726,712 B1 | 4/2004 | Raeder-Devens et al. |
| 6,736,996 B1 | 5/2004 | Carbonell et al. |
| 6,743,505 B2 | 6/2004 | Antal et al. |
| 6,749,902 B2 | 6/2004 | Yonker et al. |
| 6,755,871 B2 | 6/2004 | Damaso et al. |
| 6,756,084 B2 | 6/2004 | Fulton et al. |
| 6,767,558 B2 | 7/2004 | Wang |
| 6,780,475 B2 | 8/2004 | Fulton et al. |
| 6,794,902 B2 | 9/2004 | Becker et al. |
| 6,800,663 B2 | 10/2004 | Asgarzadeh et al. |
| 6,815,218 B1 | 11/2004 | Jacobson et al. |
| 6,821,549 B2 | 11/2004 | Jayaraman |
| 6,837,611 B2 | 1/2005 | Kuo |
| 6,838,089 B1 | 1/2005 | Carlsson et al. |
| 6,838,528 B2 | 1/2005 | Zhao |
| 6,858,598 B1 | 2/2005 | McKearn et al. |
| 6,860,123 B1 | 3/2005 | Uhlin |
| 6,868,123 B2 | 3/2005 | Uhlin |
| 6,884,377 B1 | 4/2005 | Burnham et al. |
| 6,884,823 B1 | 4/2005 | Pierick et al. |
| 6,897,205 B2 | 5/2005 | Beckert et al. |
| 6,905,555 B2 | 6/2005 | DeYoung et al. |
| 6,908,624 B2 | 6/2005 | Hossainy et al. |
| 6,916,800 B2 | 7/2005 | McKearn et al. |
| 6,923,979 B2 | 8/2005 | Fotland et al. |
| 6,936,270 B2 | 8/2005 | Watson et al. |
| 6,939,569 B1 | 9/2005 | Green et al. |
| 6,973,718 B2 | 12/2005 | Sheppard, Jr. et al. |
| 7,056,591 B1 | 6/2006 | Pacetti et al. |
| 7,094,256 B1 | 8/2006 | Shah et al. |
| 7,148,201 B2 | 12/2006 | Stern et al. |
| 7,152,452 B2 | 12/2006 | Kokish |
| 7,160,592 B2 | 1/2007 | Rypacek et al. |
| 7,163,715 B1 | 1/2007 | Kramer |
| 7,169,404 B2 | 1/2007 | Hossainy et al. |
| 7,171,255 B2 | 1/2007 | Holupka et al. |
| 7,201,750 B1 | 4/2007 | Eggers et al. |
| 7,201,940 B1 | 4/2007 | Kramer |
| 7,229,837 B2 | 6/2007 | Chen |
| 7,278,174 B2 | 10/2007 | Villalobos |
| 7,279,174 B2 | 10/2007 | Pacetti et al. |
| 7,282,020 B2 | 10/2007 | Kaplan |
| 7,308,748 B2 | 12/2007 | Kokish |
| 7,323,454 B2 | 1/2008 | De Nijs et al. |
| 7,326,734 B2 | 2/2008 | Zi et al. |
| 7,329,383 B2 | 2/2008 | Stinson |
| 7,378,105 B2 | 5/2008 | Burke et al. |
| 7,419,696 B2 | 9/2008 | Berg et al. |
| 7,429,378 B2 | 9/2008 | Serhan et al. |
| 7,444,162 B2 | 10/2008 | Hassan |
| 7,455,658 B2 | 11/2008 | Wang |
| 7,455,688 B2 | 11/2008 | Furst et al. |
| 7,456,151 B2 | 11/2008 | Li et al. |
| 7,462,593 B2 | 12/2008 | Cuttitta et al. |
| 7,485,113 B2 | 2/2009 | Varner et al. |
| 7,498,042 B2 | 3/2009 | Igaki et al. |
| 7,524,865 B2 | 4/2009 | D'Amato et al. |
| 7,537,610 B2 | 5/2009 | Reiss |
| 7,537,785 B2 | 5/2009 | Loscalzo et al. |
| 7,553,827 B2 | 6/2009 | Attawia et al. |
| 7,713,538 B2 | 5/2010 | Lewis et al. |
| 7,727,275 B2 | 6/2010 | Betts et al. |
| 7,745,566 B2 | 6/2010 | Chattopadhyay et al. |
| 7,763,277 B1 | 7/2010 | Canham et al. |
| 7,771,468 B2 | 8/2010 | Whitbourne et al. |
| 7,837,726 B2 | 11/2010 | Von Oepen et al. |
| 7,842,312 B2 | 11/2010 | Burgermeister et al. |
| 7,919,108 B2 | 4/2011 | Reyes et al. |
| 7,955,383 B2 | 6/2011 | Krivoruchko et al. |
| 7,967,855 B2 | 6/2011 | Furst et al. |
| 7,972,661 B2 | 7/2011 | Pui et al. |
| 8,070,796 B2 | 12/2011 | Furst et al. |
| 8,109,904 B1 | 2/2012 | Papp |
| 8,295,565 B2 | 10/2012 | Gu et al. |
| 8,298,565 B2 | 10/2012 | Taylor et al. |
| 8,333,803 B2 | 12/2012 | Park et al. |
| 8,377,356 B2 | 2/2013 | Huang et al. |
| 8,535,372 B1 | 9/2013 | Fox et al. |
| 8,709,071 B1 | 4/2014 | Huang et al. |
| 8,753,659 B2 | 6/2014 | Lewis et al. |
| 8,753,709 B2 | 6/2014 | Hossainy et al. |
| 8,758,429 B2 | 6/2014 | Taylor et al. |
| 8,795,762 B2 | 8/2014 | Fulton et al. |
| 8,834,913 B2 | 9/2014 | Shaw et al. |
| 8,852,625 B2 | 10/2014 | DeYoung et al. |
| 8,900,651 B2 | 12/2014 | McClain et al. |
| 9,090,029 B2 | 7/2015 | Prevost |
| 9,433,516 B2 | 9/2016 | McClain et al. |
| 9,486,431 B2 | 11/2016 | McClain et al. |
| 2001/0026804 A1 | 10/2001 | Boutignon |
| 2001/0034336 A1 | 10/2001 | Shah et al. |
| 2001/0037143 A1 | 11/2001 | Oepen |
| 2001/0044629 A1 | 11/2001 | Stinson |
| 2001/0049551 A1 | 12/2001 | Tseng et al. |
| 2002/0007209 A1 | 1/2002 | Scheerder et al. |
| 2002/0051485 A1 | 5/2002 | Bottomley |
| 2002/0051845 A1 | 5/2002 | Mehta et al. |
| 2002/0082680 A1 | 6/2002 | Shanley et al. |
| 2002/0091433 A1 | 7/2002 | Ding et al. |
| 2002/0099332 A1 | 7/2002 | Slepian et al. |
| 2002/0125860 A1 | 9/2002 | Schworm et al. |
| 2002/0133072 A1 | 9/2002 | Wang et al. |
| 2002/0144757 A1 | 10/2002 | Craig et al. |
| 2002/0151959 A1 | 10/2002 | Von Oepen |
| 2003/0001830 A1 | 1/2003 | Wampler et al. |
| 2003/0004563 A1 | 1/2003 | Jackson et al. |
| 2003/0028244 A1 | 2/2003 | Bates et al. |
| 2003/0031699 A1 | 2/2003 | Van Antwerp |
| 2003/0077200 A1 | 4/2003 | Craig et al. |
| 2003/0088307 A1 | 5/2003 | Shulze et al. |
| 2003/0125800 A1 | 7/2003 | Shulze et al. |
| 2003/0143315 A1 | 7/2003 | Pui et al. |
| 2003/0170305 A1 | 9/2003 | O'Neil et al. |
| 2003/0180376 A1 | 9/2003 | Dalal et al. |
| 2003/0185964 A1 | 10/2003 | Weber et al. |
| 2003/0204238 A1 | 10/2003 | Tedeschi |
| 2003/0209835 A1 | 11/2003 | Chun et al. |
| 2003/0222017 A1 | 12/2003 | Fulton et al. |
| 2003/0222018 A1 | 12/2003 | Yonker et al. |
| 2003/0232014 A1 | 12/2003 | Burke et al. |
| 2004/0013792 A1 | 1/2004 | Epstein et al. |
| 2004/0018228 A1 | 1/2004 | Fischell et al. |
| 2004/0022400 A1 | 2/2004 | Magrath |
| 2004/0022853 A1 | 2/2004 | Ashton et al. |
| 2004/0044397 A1 | 3/2004 | Stinson |
| 2004/0059290 A1 | 3/2004 | Palasis |
| 2004/0096477 A1 | 5/2004 | Chauhan et al. |
| 2004/0102758 A1 | 5/2004 | Davila et al. |
| 2004/0106982 A1 | 6/2004 | Jalisi |
| 2004/0122205 A1 | 6/2004 | Nathan |
| 2004/0126542 A1 | 7/2004 | Fujiwara et al. |
| 2004/0143317 A1 | 7/2004 | Stinson et al. |
| 2004/0144317 A1 | 7/2004 | Chuman et al. |
| 2004/0147904 A1 | 7/2004 | Hung et al. |
| 2004/0148007 A1 | 7/2004 | Jackson et al. |
| 2004/0157789 A1 | 8/2004 | Geall |
| 2004/0170685 A1 | 9/2004 | Carpenter et al. |
| 2004/0181278 A1 | 9/2004 | Tseng et al. |
| 2004/0193177 A1 | 9/2004 | Houghton et al. |
| 2004/0193262 A1 | 9/2004 | Shadduck |
| 2004/0220660 A1 | 11/2004 | Shanley et al. |
| 2004/0224001 A1 | 11/2004 | Pacetti et al. |

(56) References Cited

U.S. PATENT DOCUMENTS

| | | |
|---|---|---|
| 2004/0234748 A1 | 11/2004 | Stenzel |
| 2004/0236416 A1 | 11/2004 | Falotico |
| 2004/0260000 A1 | 12/2004 | Chaiko |
| 2005/0003074 A1 | 1/2005 | Brown et al. |
| 2005/0004661 A1 | 1/2005 | Lewis et al. |
| 2005/0004663 A1 | 1/2005 | Llanos et al. |
| 2005/0010275 A1 | 1/2005 | Sahatjian et al. |
| 2005/0013872 A1 | 1/2005 | Freyman |
| 2005/0015046 A1 | 1/2005 | Weber et al. |
| 2005/0019747 A1 | 1/2005 | Anderson et al. |
| 2005/0033414 A1 | 2/2005 | Zhang et al. |
| 2005/0033417 A1 | 2/2005 | Borges et al. |
| 2005/0038498 A1 | 2/2005 | Dubrow et al. |
| 2005/0048121 A1 | 3/2005 | East et al. |
| 2005/0049694 A1 | 3/2005 | Neary |
| 2005/0053639 A1 | 3/2005 | Shalaby |
| 2005/0060028 A1 | 3/2005 | Horres et al. |
| 2005/0069630 A1 | 3/2005 | Fox et al. |
| 2005/0070989 A1 | 3/2005 | Lye et al. |
| 2005/0070990 A1 | 3/2005 | Stinson |
| 2005/0070997 A1 | 3/2005 | Thornton et al. |
| 2005/0074479 A1 | 4/2005 | Weber et al. |
| 2005/0075714 A1 | 4/2005 | Cheng et al. |
| 2005/0079199 A1 | 4/2005 | Heruth et al. |
| 2005/0079274 A1 | 4/2005 | Palasis et al. |
| 2005/0084533 A1 | 4/2005 | Howdle et al. |
| 2005/0131008 A1 | 6/2005 | Betts et al. |
| 2005/0131513 A1 | 6/2005 | Myers |
| 2005/0147734 A1 | 7/2005 | Seppala et al. |
| 2005/0159704 A1 | 7/2005 | Scott et al. |
| 2005/0166841 A1 | 8/2005 | Robida |
| 2005/0175772 A1 | 8/2005 | Worsham et al. |
| 2005/0177223 A1 | 8/2005 | Palmaz |
| 2005/0191491 A1 | 9/2005 | Wang et al. |
| 2005/0196424 A1 | 9/2005 | Chappa |
| 2005/0208102 A1 | 9/2005 | Schultz |
| 2005/0209244 A1 | 9/2005 | Prescott et al. |
| 2005/0209680 A1 | 9/2005 | Gale et al. |
| 2005/0216075 A1 | 9/2005 | Wang et al. |
| 2005/0222676 A1 | 10/2005 | Shanley et al. |
| 2005/0238829 A1 | 10/2005 | Motherwell et al. |
| 2005/0245637 A1 | 11/2005 | Hossainy et al. |
| 2005/0255327 A1 | 11/2005 | Chaney et al. |
| 2005/0260186 A1 | 11/2005 | Bookbinder et al. |
| 2005/0268573 A1 | 12/2005 | Yan |
| 2005/0288481 A1 | 12/2005 | DesNoyer et al. |
| 2005/0288629 A1 | 12/2005 | Kunis |
| 2006/0001011 A1 | 1/2006 | Wilson et al. |
| 2006/0002974 A1 | 1/2006 | Pacetti et al. |
| 2006/0020325 A1 | 1/2006 | Burgermeister et al. |
| 2006/0030652 A1 | 2/2006 | Adams et al. |
| 2006/0045901 A1 | 3/2006 | Weber |
| 2006/0067974 A1 | 3/2006 | Labrecque et al. |
| 2006/0073329 A1 | 4/2006 | Boyce et al. |
| 2006/0089705 A1 | 4/2006 | Ding et al. |
| 2006/0093771 A1 | 5/2006 | Rypacek et al. |
| 2006/0094744 A1 | 5/2006 | Maryanoff et al. |
| 2006/0104969 A1 | 5/2006 | Oray et al. |
| 2006/0106455 A1 | 5/2006 | Furst et al. |
| 2006/0116755 A1 | 6/2006 | Stinson |
| 2006/0121080 A1 | 6/2006 | Lye et al. |
| 2006/0121089 A1 | 6/2006 | Michal et al. |
| 2006/0134168 A1 | 6/2006 | Chappa et al. |
| 2006/0134211 A1 | 6/2006 | Lien et al. |
| 2006/0136041 A1 | 6/2006 | Schmid et al. |
| 2006/0147698 A1 | 7/2006 | Carroll et al. |
| 2006/0153729 A1 | 7/2006 | Stinson et al. |
| 2006/0160455 A1 | 7/2006 | Sugyo et al. |
| 2006/0188547 A1 | 8/2006 | Bezwada |
| 2006/0193886 A1 | 8/2006 | Owens et al. |
| 2006/0193890 A1 | 8/2006 | Owens et al. |
| 2006/0198868 A1 | 9/2006 | DeWitt et al. |
| 2006/0210638 A1 | 9/2006 | Liversidge et al. |
| 2006/0216324 A1 | 9/2006 | Stucke et al. |
| 2006/0222756 A1 | 10/2006 | Davila et al. |
| 2006/0228415 A1 | 10/2006 | Oberegger et al. |
| 2006/0228453 A1 | 10/2006 | Cromack et al. |
| 2006/0235506 A1 | 10/2006 | Ta et al. |
| 2006/0276877 A1 | 12/2006 | Owens et al. |
| 2006/0287611 A1 | 12/2006 | Fleming |
| 2007/0009564 A1 | 1/2007 | McClain et al. |
| 2007/0009664 A1 | 1/2007 | Fallais et al. |
| 2007/0026041 A1 | 2/2007 | DesNoyer et al. |
| 2007/0026042 A1 | 2/2007 | Narayanan |
| 2007/0032864 A1 | 2/2007 | Furst et al. |
| 2007/0038227 A1 | 2/2007 | Massicotte et al. |
| 2007/0038289 A1 | 2/2007 | Nishide et al. |
| 2007/0043434 A1 | 2/2007 | Meerkin et al. |
| 2007/0059350 A1 | 3/2007 | Kennedy et al. |
| 2007/0065478 A1 | 3/2007 | Hossainy |
| 2007/0110888 A1 | 5/2007 | Radhakrishnan et al. |
| 2007/0123973 A1 | 5/2007 | Roth et al. |
| 2007/0123977 A1 | 5/2007 | Cottone et al. |
| 2007/0128274 A1 | 6/2007 | Zhu et al. |
| 2007/0148251 A1 | 6/2007 | Hossainy et al. |
| 2007/0154513 A1 | 7/2007 | Atanasoska et al. |
| 2007/0154554 A1 | 7/2007 | Burgermeister et al. |
| 2007/0196242 A1 | 8/2007 | Boozer et al. |
| 2007/0196423 A1 | 8/2007 | Ruane et al. |
| 2007/0198081 A1 | 8/2007 | Castro et al. |
| 2007/0200268 A1 | 8/2007 | Dave |
| 2007/0203569 A1 | 8/2007 | Burgermeister et al. |
| 2007/0219579 A1 | 9/2007 | Paul |
| 2007/0225795 A1 | 9/2007 | Granada et al. |
| 2007/0250157 A1 | 10/2007 | Nishide et al. |
| 2007/0259017 A1 | 11/2007 | Francis |
| 2007/0280992 A1 | 12/2007 | Margaron et al. |
| 2008/0030066 A1 | 2/2008 | Mercier et al. |
| 2008/0051866 A1 | 2/2008 | Chen et al. |
| 2008/0065192 A1 | 3/2008 | Berglund |
| 2008/0071347 A1 | 3/2008 | Cambronne |
| 2008/0071358 A1 | 3/2008 | Weber et al. |
| 2008/0071359 A1 | 3/2008 | Thornton et al. |
| 2008/0075753 A1 | 3/2008 | Chappa |
| 2008/0077232 A1 | 3/2008 | Nishide |
| 2008/0085880 A1 | 4/2008 | Viswanath et al. |
| 2008/0091008 A1 | 4/2008 | Viswanath et al. |
| 2008/0095919 A1 | 4/2008 | McClain et al. |
| 2008/0097575 A1 | 4/2008 | Cottone |
| 2008/0097591 A1 | 4/2008 | Savage et al. |
| 2008/0098178 A1 | 4/2008 | Veazey et al. |
| 2008/0107702 A1 | 5/2008 | Jennissen |
| 2008/0118543 A1 | 5/2008 | Pacetti et al. |
| 2008/0124372 A1 | 5/2008 | Hossainy et al. |
| 2008/0138375 A1 | 6/2008 | Yan et al. |
| 2008/0206304 A1 | 8/2008 | Lindquist et al. |
| 2008/0213464 A1 | 9/2008 | O'Connor |
| 2008/0233267 A1 | 9/2008 | Berglund |
| 2008/0255510 A1 | 10/2008 | Wang |
| 2008/0269449 A1 | 10/2008 | Chattopadhyay et al. |
| 2008/0286325 A1 | 11/2008 | Reyes et al. |
| 2008/0292776 A1 | 11/2008 | Dias et al. |
| 2008/0300669 A1 | 12/2008 | Hossainy |
| 2008/0300689 A1 | 12/2008 | McKinnon et al. |
| 2009/0043379 A1 | 2/2009 | Prescott |
| 2009/0062909 A1 | 3/2009 | Taylor et al. |
| 2009/0068266 A1 | 3/2009 | Raheja et al. |
| 2009/0076446 A1 | 3/2009 | Dubuclet, IV et al. |
| 2009/0076595 A1 | 3/2009 | Lindquist et al. |
| 2009/0082855 A1 | 3/2009 | Borges et al. |
| 2009/0098178 A1 | 4/2009 | Hofmann et al. |
| 2009/0105687 A1 | 4/2009 | Deckman et al. |
| 2009/0105809 A1 | 4/2009 | Lee et al. |
| 2009/0110711 A1 | 4/2009 | Trollsas et al. |
| 2009/0111787 A1 | 4/2009 | Lim et al. |
| 2009/0123515 A1 | 5/2009 | Taylor et al. |
| 2009/0123521 A1 | 5/2009 | Weber et al. |
| 2009/0186069 A1 | 7/2009 | DeYoung et al. |
| 2009/0202609 A1 | 8/2009 | Keough et al. |
| 2009/0216317 A1 | 8/2009 | Cromack et al. |
| 2009/0227949 A1 | 9/2009 | Knapp et al. |
| 2009/0231578 A1 | 9/2009 | Ling et al. |
| 2009/0263460 A1 | 10/2009 | McDonald |
| 2009/0285974 A1 | 11/2009 | Kerrigan et al. |

(56) References Cited

U.S. PATENT DOCUMENTS

| | | |
|---|---|---|
| 2009/0292351 A1 | 11/2009 | McClain et al. |
| 2009/0292776 A1 | 11/2009 | Nesbitt et al. |
| 2009/0297578 A1 | 12/2009 | Trollsas et al. |
| 2009/0300689 A1 | 12/2009 | Conte et al. |
| 2010/0000328 A1 | 1/2010 | Mahmoud |
| 2010/0006358 A1 | 1/2010 | Ishikawa |
| 2010/0015200 A1 | 1/2010 | McClain et al. |
| 2010/0030261 A1 | 2/2010 | McClain |
| 2010/0042206 A1 | 2/2010 | Yadav et al. |
| 2010/0055145 A1 | 3/2010 | Betts et al. |
| 2010/0055294 A1 | 3/2010 | Wang et al. |
| 2010/0063570 A1 | 3/2010 | Pacetti et al. |
| 2010/0063580 A1 | 3/2010 | McClain et al. |
| 2010/0074934 A1 | 3/2010 | Hunter |
| 2010/0131044 A1 | 5/2010 | Patel |
| 2010/0137491 A1 | 6/2010 | Rose et al. |
| 2010/0155496 A1 | 6/2010 | Stark et al. |
| 2010/0166869 A1 | 7/2010 | Desai et al. |
| 2010/0196482 A1 | 8/2010 | Radovic-Moreno et al. |
| 2010/0198330 A1 | 8/2010 | Hossainy et al. |
| 2010/0198331 A1 | 8/2010 | Rapoza et al. |
| 2010/0211164 A1 | 8/2010 | McClain et al. |
| 2010/0228348 A1 | 9/2010 | McClain et al. |
| 2010/0233332 A1 | 9/2010 | Xing et al. |
| 2010/0239635 A1 | 9/2010 | McClain et al. |
| 2010/0241220 A1 | 9/2010 | McClain et al. |
| 2010/0256746 A1 | 10/2010 | Taylor et al. |
| 2010/0256748 A1 | 10/2010 | Taylor et al. |
| 2010/0262224 A1 | 10/2010 | Kleiner |
| 2010/0272775 A1 | 10/2010 | Cleek et al. |
| 2010/0272778 A1 | 10/2010 | McClain et al. |
| 2010/0285085 A1 | 11/2010 | Stankus et al. |
| 2010/0298928 A1 | 11/2010 | McClain et al. |
| 2010/0303881 A1 | 12/2010 | Hoke et al. |
| 2010/0305689 A1 | 12/2010 | Venkatraman et al. |
| 2011/0009953 A1 | 1/2011 | Luk et al. |
| 2011/0034422 A1 | 2/2011 | Kannan et al. |
| 2011/0159069 A1 | 6/2011 | Shaw et al. |
| 2011/0160751 A1 | 6/2011 | Granja Filho |
| 2011/0172763 A1 | 7/2011 | Ndondo-Lay |
| 2011/0189299 A1 | 8/2011 | Okubo et al. |
| 2011/0190864 A1 | 8/2011 | McClain et al. |
| 2011/0223212 A1 | 9/2011 | Taton et al. |
| 2011/0238161 A1 | 9/2011 | Fulton et al. |
| 2011/0243884 A1 | 10/2011 | O'Shea et al. |
| 2011/0257732 A1 | 10/2011 | McClain et al. |
| 2011/0264190 A1 | 10/2011 | McClain et al. |
| 2011/0301697 A1 | 12/2011 | Hoffmann et al. |
| 2012/0064124 A1 | 3/2012 | McClain et al. |
| 2012/0064143 A1 | 3/2012 | Sharp et al. |
| 2012/0065723 A1 | 3/2012 | Drasler et al. |
| 2012/0101566 A1 | 4/2012 | Mews et al. |
| 2012/0150275 A1 | 6/2012 | Shaw-Klein |
| 2012/0160408 A1 | 6/2012 | Clerc et al. |
| 2012/0172787 A1 | 7/2012 | McClain et al. |
| 2012/0177742 A1 | 7/2012 | McClain et al. |
| 2012/0231037 A1 | 9/2012 | Levi et al. |
| 2012/0239161 A1 | 9/2012 | Datta et al. |
| 2012/0271396 A1 | 10/2012 | Zheng et al. |
| 2012/0280432 A1 | 11/2012 | Chen et al. |
| 2012/0290075 A1 | 11/2012 | Mortisen et al. |
| 2012/0323311 A1 | 12/2012 | McClain et al. |
| 2013/0006351 A1 | 1/2013 | Taylor et al. |
| 2013/0035754 A1 | 2/2013 | Shulze et al. |
| 2013/0087270 A1 | 4/2013 | Hossainy et al. |
| 2013/0110138 A1 | 5/2013 | Hurtado et al. |
| 2013/0172853 A1 | 7/2013 | McClain et al. |
| 2013/0291476 A1 | 11/2013 | Broughton, Jr. et al. |
| 2014/0343667 A1 | 11/2014 | McClain |
| 2014/0350522 A1 | 11/2014 | McClain et al. |
| 2014/0371717 A1 | 12/2014 | McClain et al. |
| 2015/0024116 A1 | 1/2015 | Matson et al. |
| 2015/0025620 A1 | 1/2015 | Taylor et al. |
| 2015/0250926 A1 | 9/2015 | McClain et al. |
| 2016/0095726 A1 | 4/2016 | McClain et al. |

FOREIGN PATENT DOCUMENTS

| | | |
|---|---|---|
| CA | 2615452 A1 | 1/2007 |
| CA | 2650590 A1 | 11/2007 |
| CA | 2679712 A1 | 7/2008 |
| CA | 2684482 A1 | 10/2008 |
| CA | 2721832 A1 | 12/2009 |
| CN | 2423899 Y | 3/2001 |
| CN | 1465410 A | 1/2004 |
| CN | 1575860 A | 2/2005 |
| CN | 1649551 A | 8/2005 |
| CN | 1684641 A | 10/2005 |
| CN | 101161300 A | 4/2008 |
| CN | 102481195 A | 5/2012 |
| DE | 4336209 A1 | 3/1995 |
| DE | 29702671 U1 | 4/1997 |
| DE | 29716476 U1 | 12/1997 |
| DE | 19633901 A1 | 2/1998 |
| DE | 29716467 U1 | 2/1998 |
| DE | 19740506 A1 | 3/1998 |
| DE | 19754870 A1 | 8/1998 |
| DE | 19822157 A1 | 11/1999 |
| DE | 69611186 T2 | 5/2001 |
| EP | 0335341 | 10/1989 |
| EP | 0604022 A1 | 6/1994 |
| EP | 800801 A1 | 10/1997 |
| EP | 0876806 A1 | 11/1998 |
| EP | 0982041 A1 | 3/2000 |
| EP | 1195822 A2 | 4/2002 |
| EP | 1325758 A2 | 7/2003 |
| EP | 1327422 A1 | 7/2003 |
| EP | 1454677 A2 | 9/2004 |
| EP | 1502655 A2 | 2/2005 |
| EP | 1810665 A1 | 7/2007 |
| EP | 1909973 A2 | 4/2008 |
| EP | 2197070 A1 | 6/2010 |
| EP | 2293357 A1 | 3/2011 |
| EP | 2293366 A1 | 3/2011 |
| FR | 2758253 A1 | 7/1998 |
| JP | 698902 | 4/1994 |
| JP | H06218063 A | 8/1994 |
| JP | H08206223 A | 8/1996 |
| JP | H0956807 A | 3/1997 |
| JP | H10295824 A | 2/1998 |
| JP | H10151207 A | 6/1998 |
| JP | H10314313 A | 12/1998 |
| JP | H1157018 A | 3/1999 |
| JP | 2000316981 A | 11/2000 |
| JP | 2001521503 A | 11/2001 |
| JP | 2003205037 A | 7/2003 |
| JP | 2003533286 A | 11/2003 |
| JP | 2003533492 A | 11/2003 |
| JP | 2003533493 A | 11/2003 |
| JP | 2004512059 A | 4/2004 |
| JP | 2004173770 A | 6/2004 |
| JP | 2004518458 A | 6/2004 |
| JP | 2004528060 A | 9/2004 |
| JP | 2004529674 A | 9/2004 |
| JP | 2005505318 | 2/2005 |
| JP | 2005519080 A | 6/2005 |
| JP | 2005523119 A | 8/2005 |
| JP | 2005523332 A | 8/2005 |
| JP | 2005296690 A | 10/2005 |
| JP | 2006506191 A | 2/2006 |
| JP | 2006512175 A | 4/2006 |
| JP | 2007502281 A | 2/2007 |
| JP | 2007215620 A | 8/2007 |
| JP | 2009501566 A | 1/2009 |
| JP | 2009529399 A | 8/2009 |
| JP | 2010052503 A | 3/2010 |
| JP | 2010515539 A | 5/2010 |
| JP | 2010516307 A | 5/2010 |
| JP | 2011517589 A | 6/2011 |
| JP | 2012527318 A | 11/2012 |
| KR | 1020040034064 | 4/2004 |
| KR | 101231197 B1 | 2/2013 |
| WO | 9409010 A1 | 4/1994 |
| WO | 9506487 A2 | 3/1995 |
| WO | 9616691 A1 | 6/1996 |

(56) References Cited

FOREIGN PATENT DOCUMENTS

| | | |
|---|---|---|
| WO | 9620698 A2 | 7/1996 |
| WO | 9632907 A1 | 10/1996 |
| WO | 9641807 A1 | 12/1996 |
| WO | 9745502 A1 | 12/1997 |
| WO | 9802441 A2 | 1/1998 |
| WO | 9908729 A1 | 2/1999 |
| WO | 9915530 A1 | 4/1999 |
| WO | 9917680 A1 | 4/1999 |
| WO | 99016388 A1 | 4/1999 |
| WO | 0006051 A1 | 2/2000 |
| WO | 0025702 A1 | 5/2000 |
| WO | 00032238 A1 | 6/2000 |
| WO | 0114387 A1 | 3/2001 |
| WO | 2001054662 | 8/2001 |
| WO | 0187345 A1 | 11/2001 |
| WO | 0187368 A1 | 11/2001 |
| WO | 0187372 A1 | 11/2001 |
| WO | 01087371 A2 | 11/2001 |
| WO | 0226281 A1 | 4/2002 |
| WO | 0240702 | 5/2002 |
| WO | 0243799 | 6/2002 |
| WO | 02055122 A1 | 7/2002 |
| WO | 02074194 A2 | 9/2002 |
| WO | 02090085 A1 | 11/2002 |
| WO | 02100456 A1 | 12/2002 |
| WO | 03039553 A1 | 5/2003 |
| WO | 03082368 A1 | 10/2003 |
| WO | 03090684 A2 | 11/2003 |
| WO | 03101624 A1 | 12/2003 |
| WO | 2004009145 A1 | 1/2004 |
| WO | 2004028406 A1 | 4/2004 |
| WO | 2004028589 A2 | 4/2004 |
| WO | 2004043506 A1 | 5/2004 |
| WO | 2004045450 A2 | 6/2004 |
| WO | 04098574 A1 | 11/2004 |
| WO | 2004101017 A2 | 11/2004 |
| WO | 2005018696 A1 | 3/2005 |
| WO | 05042623 A1 | 5/2005 |
| WO | 2005063319 A1 | 7/2005 |
| WO | 05069889 A2 | 8/2005 |
| WO | 2005117942 A2 | 12/2005 |
| WO | 2006014534 A2 | 2/2006 |
| WO | 2006052575 A2 | 5/2006 |
| WO | 2006063021 A2 | 6/2006 |
| WO | 2006063430 A1 | 6/2006 |
| WO | 2006065685 A2 | 6/2006 |
| WO | 06083796 A2 | 8/2006 |
| WO | 2006099276 A2 | 9/2006 |
| WO | 07002238 A2 | 1/2007 |
| WO | 2007011707 A2 | 1/2007 |
| WO | 2007011708 A2 | 1/2007 |
| WO | 2007017707 A2 | 1/2007 |
| WO | 2007017708 A3 | 1/2007 |
| WO | 007092179 A2 | 8/2007 |
| WO | 2007106441 A2 | 9/2007 |
| WO | 2007127363 A2 | 11/2007 |
| WO | 07143609 A2 | 12/2007 |
| WO | 2008024626 A2 | 2/2008 |
| WO | 08046641 A2 | 4/2008 |
| WO | 08046642 A2 | 4/2008 |
| WO | 2008042909 A2 | 4/2008 |
| WO | 08052000 A2 | 5/2008 |
| WO | 2008070996 A1 | 6/2008 |
| WO | 2008086369 A1 | 7/2008 |
| WO | 2008131131 A1 | 10/2008 |
| WO | 2008148013 A1 | 12/2008 |
| WO | 09039553 A1 | 4/2009 |
| WO | 09051614 A1 | 4/2009 |
| WO | 2009051780 A1 | 4/2009 |
| WO | 2009096822 A1 | 8/2009 |
| WO | 2009113605 A1 | 9/2009 |
| WO | 2009120361 A2 | 10/2009 |
| WO | 2009146209 A1 | 12/2009 |
| WO | 2010001932 A1 | 1/2010 |
| WO | 2010009335 A1 | 1/2010 |
| WO | 10075590 A2 | 7/2010 |
| WO | 2010086863 A2 | 8/2010 |
| WO | 2010111196 A2 | 9/2010 |
| WO | 2010111232 A2 | 9/2010 |
| WO | 2010111238 A2 | 9/2010 |
| WO | 2010120552 A2 | 10/2010 |
| WO | 2010121187 A2 | 10/2010 |
| WO | 2010135369 A1 | 11/2010 |
| WO | 10136604 A1 | 12/2010 |
| WO | 2011009096 A1 | 1/2011 |
| WO | 2011097103 A1 | 8/2011 |
| WO | 11119762 A1 | 9/2011 |
| WO | 2011119159 A1 | 9/2011 |
| WO | 11130448 A1 | 10/2011 |
| WO | 11133655 A1 | 10/2011 |
| WO | 2011140519 A2 | 11/2011 |
| WO | 12009684 A2 | 1/2012 |
| WO | 12034079 A2 | 3/2012 |
| WO | 2012078955 A1 | 6/2012 |
| WO | 2012082502 A1 | 6/2012 |
| WO | 12092504 A2 | 7/2012 |
| WO | 12142319 A1 | 10/2012 |
| WO | 12166819 A1 | 12/2012 |
| WO | 2013003644 A1 | 1/2013 |
| WO | 2013012689 A1 | 1/2013 |
| WO | 2013025535 A1 | 2/2013 |
| WO | 13059509 A1 | 4/2013 |
| WO | 13177211 A1 | 11/2013 |
| WO | 2013173657 A1 | 11/2013 |
| WO | 2014063111 A1 | 4/2014 |
| WO | 2014165264 A1 | 10/2014 |
| WO | 2014186532 A1 | 11/2014 |

OTHER PUBLICATIONS

PCT/EP2000/004658 International Search Report from dated Sep. 15, 2000.
PCT/US06/24221 International Preliminary Report on Patentability dated Dec. 24, 2007.
PCT/US06/24221 International Search Report dated Jan. 29, 2007.
PCT/US06/27321 International Preliminary Report on Patentability dated Jan. 16, 2008.
PCT/US06/27321 International Search Report dated Oct. 16, 2007.
PCT/US06/27321 Written Opinion dated Oct. 16, 2007.
PCT/US06/27322 International Preliminary Report on Patentability dated Jan. 16, 2008.
PCT/US06/27322 International Search Report dated Apr. 25, 2007.
PCT/US07/10227 International Preliminary Report on Patentability dated Oct. 28, 2008.
PCT/US07/10227 International Search Report dated Aug. 8, 2008.
PCT/US07/80213 International Preliminary Report on Patentability dated Apr. 7, 2009.
PCT/US07/80213 International Search Report dated Apr. 16, 2008.
PCT/US07/82275 International Search Report dated Apr. 18, 2008.
PCT/US07/82775 International Preliminary Report on Patentablity dated May 5, 2009.
PCT/US08/11852 International Preliminary Report on Patentability dated Apr. 20, 2010.
PCT/US08/11852 International Search Report dated Dec. 19, 2008.
PCT/US08/50536 International Preliminary Report on Patentability dated Jul. 14, 2009.
PCT/US08/50536 International Search Report dated Jun. 2, 2008.
PCT/US08/60671 International Preliminary Report on Patentability dated Oct. 20, 2009.
PCT/US08/60671 International Search Report dated Sep. 5, 2008.
PCT/US08/64732 International Preliminary Report on Patentability dated Dec. 1, 2009.
PCT/US08/64732 International Search Report dated Sep. 4, 2008.
PCT/US09/41045 International Preliminary Report on Patentability dated Oct. 19, 2010.
PCT/US09/41045 International Search Report dated Aug. 11, 2009.
PCT/US09/50883 International Preliminary Report on Patentability dated Jan. 18, 2011.
PCT/US09/50883 International Search Report dated Nov. 17, 2009.

(56) References Cited

OTHER PUBLICATIONS

PCT/US09/69603 International Preliminary Report on Patentability dated Jun. 29, 2011.
PCT/US09/69603 International Search Report dated Nov. 5, 2010.
PCT/US10/28195 International Preliminary Report on Patentability dated Sep. 27, 2011.
PCT/US10/28195 Search Report and Written Opinion dated Jan. 21, 2011.
PCT/US10/28253 International Preliminary Report on Patentability dated Sep. 27, 2011.
PCT/US10/28253 Search Report and Written Opinion dated Dec. 6, 2010.
PCT/US10/28265 International Report on Patentability dated Sep. 27, 2011.
PCT/US10/28265 Search Report and Written Opinion dated Dec. 13, 2010.
PCT/US10/29494 International Preliminary Report on Patentability dated Oct. 4, 2011.
PCT/US10/29494 Search Report and Written Opinion dated Feb. 7, 2011.
PCT/US10/31470 International Preliminary Report on Patentability dated Oct. 18, 2011.
PCT/US10/31470 Search Report and Written Opinion dated Jan. 28, 2011.
PCT/US10/42355 International Preliminary Report on Patentability dated Jan. 17, 2012.
PCT/US10/42355 Search Report dated Sep. 2, 2010.
PCT/US11/22623 International Preliminary Report on Patentability dated Aug. 7, 2012.
PCT/US11/22623 Search Report and Written Opinion dated Mar. 28, 2011.
PCT/US11/29667 International Search Report and Written Opinion dated Jun. 1, 2011.
PCT/US11/32371 International Report on Patentability dated Oct. 16, 2012.
PCT/US11/32371 International Search Report dated Jul. 7, 2011.
PCT/US11/33225 International Search Report and Written Opinion dated Jul. 7, 2011.
PCT/US11/44263 International Preliminary Report on Patentability dated Jan. 22, 2013.
PCT/US11/44263 International Search Report and Written Opinion dated Feb. 9, 2012.
PCT/US11/51092 International Preliminary Report on Patentability dated Mar. 12, 2013.
Third Party Submission for Application No. JP2015-538086 dated Jun. 4, 2018.
Wagenlehner et al., "A pollen extract (Cemilton) in patients with inflammatory chronic prostatitis/chronic pelvic pain syndrome: a multicentre, randomized, prospective, double-blind, placebo-controlled phase 3 study," Eur Urol 9 (Epub) (Jun. 3, 2009).
Wang et al. "Synthesis, characterization, biodegradation, and drug delivery application of biodegradable lactic/glycolic acid polymers: I. Synthesis and characterization" J. Biomater. Sci. Polymer Edn. 11(3):301-318 (2000).
Wang et al., "Treatment with melagatran alone or in combination with thrombolytic therapy reduced ischemic brain injury", Exp. Neuro. 213(1):171-175 (2008).
Wang, X.; Venkatraman, S.S.; Boey, F.Y.C.; Loo, J.S.C.; Tan, L.P. "Controlled release of sirolimus from a multilayered PLGA stent matrix" Biomaterials 2006, 27, 5588-5595.
Warner et al., "Mitomycin C and airway surgery: how well does it work?" Ontolaryngol Head Neck Surg. 138(6):700-709 (2008).
Wermuth, CG, "Similarity in drugs: reflections on analogue design", Drug Discov Today. Apr. 11, 2006(7-8):348-54.
Witjes et al., "Intravesical pharmacotherapy for non-muscle-invasive bladder cancer: a critical analysis of currently available drugs, treatment schedules, and long-term results," Eur. Urol. 53(1):45-52.

Wu et al., "Study on the preparation and characterization of biodegradable polylactide/multi-walled carbon nanotubes nanocomposites", Polymer 48 (2007) 4449-4458.
Xu et al., "Biodegradation of poly(L-lactide-co-glycolide) tube stents in bile", Polymer Degradation and Stability. 93:811-817 (2008).
Xue et al., "Spray-as-you-go airway topical anesthesia in patients with a difficult airway: a randomized, double-blind comparison of 2% and 4% lidocaine, Anesth. blind comparison of 2% and 4% lidocaine," Anesth. Analg. 108(2): 536-543 (2009).
Yepes et al., "Tissue-type plasminogen activator in the ischemic brain: more than a thrombolytic," Trends Neurosci. 32(1):48-55 (2009).
Yousuf et al., "Resveratrol exerts its neuroprotective effect by modulating mitochondrial dysfunction and associated cell death during cerebral ischemia", Brain Res. 1250:242-253 (2009).
Zhou, S.; Deng, X.; Li, X.; Jia, W.; Liu, L. "Synthesis and Characterization of Biodegradable Low Molecular Weight Aliphatic Polyesters and Their Use in Protein-Delivery Systems" J. Appl. Polym. Sci. 2004, 91, 1848-1856.
Zilberman et al., Drug-Eluting bioresorbable steuts for various applications, Annu Rev Biomed Eng,., 2006;8: 158-180.
PCT/US11/51092 International Search Report dated Mar. 27, 2012.
PCT/US11/51092 Written Opinion dated Mar. 27, 2012.
PCT/US11/67921 International Preliminary Report on Patentability dated Jul. 2, 2013.
PCT/US11/67921 Search Report and Written Opinion dated Jun. 22, 2012.
PCT/US12/33367 International Preliminary Report on Patentability dated Oct. 15, 2013.
PCT/US12/33367 International Search Report dated Aug. 1, 2012.
PCT/US12/40040 International Search Report dated Sep. 7, 2012.
PCT/US12/46545 International Search Report dated Nov. 20, 2012.
PCT/US12/50408 International Search Report dated Oct. 16, 2012.
PCT/US12/60896 International Search Report and Written Opinion dated Dec. 28, 2012.
PCT/US13/41466 International Preliminary Report on Patentability dated Nov. 18, 2014.
PCT/US13/41466 International Search Report and Written Opinion dated Oct. 17, 2013.
PCT/US13/42093 International Preliminary Report on Patentability dated Nov. 25, 2014.
PCT/US13/42093 International Search Report and Written Opinion dated Oct. 24, 2013.
PCT/US13/65777 International Search Report and Written Opinion dated Jan. 29, 2014.
PCT/US14/25017 International Search Report and Written Opinion dated Jul. 7, 2014.
PCT/US14/38117 International Search Report and Written Opinion dated Oct. 7, 2014.
Perry et al., Chemical Engineers Handbook, 5th Edition, McGraw-Hill, New York, 1973; 20-106.
Plas et al., "Tubers and tumors: rapamycin therapy for benign and malignant tumors", Curr Opin Cell Bio 21:230-236, (2009).
Poling et al., The Properties of Gases and Liquids. McGraw-Hill. 2001; 9:1-9.97.
Pontari, "Chronic prostatitis/chronic pelvic pain syndrome in elderly men: toward better understanding and treatment," Drugs Aging 20(15): 1111-1115 (2003).
Pontari, "Inflammation and anti-inflammatory therapy in chronic prostatits," Urology 60(6Suppl):29-33 (2002).
Putkisto, K. et al. "Polymer Coating of Paper Using Dry Surface Treatment—Coating Structure and Performance", ePlace newsletter, Apr. 12, 2004, vol. 1, No. 8, pp. 1-20.
Ranade et al., "Physical characterization of controlled release of paclitaxel from the TAXUS Express2 drug-eluting stent," J. Biomed Mater. Res. 71 (4):625-634 (2004).
Ranganath et al., "Hydrogel matrix entrapping PLGA-paclitaxel microspheres: drug delivery with near zero-order release and implantability advantages for malignant brain tumour chemotherapy," Pharm Res (Epub) Jun. 20, 2009).

(56) References Cited

OTHER PUBLICATIONS

Reddy et al., "Inhibition of apoptosis through localized delivery of rapamycin-loaded nanoparticles prevented neointimal hyperplasia and reendothelialized injured artery," Circ Cardiovasc Interv 2008;1;209-216.

Ristikankare et al., "Sedation, topical phamygeal anesthesia and cardiorespiratory safety during gastroscopy," J. Clin Gastorenterol. 40(1 ):899-905 (2006).

Sahajanand Medical Technologies, Pledged to Save Millions, Supralimus Core Sirolimus Eluting Coronary Stent: Sahajanand, Jul. 6, 2008.

Salo et al., "Biofilm formation by *Escherichia coli* isolated from patients with urinary tract infections," Clin Nephrol. 71 (5):501-507 (2009).

Saxena et al., "Haemodialysis catheter-related bloodstream infections: current treatment options and strategies for prevention," Swiss Med Wkly 135:127-138 (2005).

Schetsky, L. McDonald, "Shape Memory Alloys", Encyclopedia of Chemical Technology (3d Ed), John Wiley & Sons 1982, vol. 20 pp. 726-736.

Scheufler et al., "Crystal Structure of Human Bone Morphogenetic Protein-2 at 2.7 Angstrom resolution," Journal of Molecular Biology, vol. 287, Issue 1, Mar. 1999, pp. 103-115, [retrieved online] at http://www.sciencedirect.comIscience/article/pii/S002283 699925901.

Schmidt et al., "A Comparison of the Mechanical Performance Characteristics of Seven Drug-Eluting Stent Systems," Catheterization and Cardiovascular Interventions 73:350-360 (2009).

Schmidt et al., "In vitro measurement of quality parameters of stent-catheter systems," Biomed Techn 50 (SI):1505-1506 (2005).

Schmidt et al., "New aspects of in vitro testing of arterial stents based on the new European standard," EN 14299, [online] (2009), [retrieved on Mar. 10, 2001] <http://www.libOev .de/pl/pdf/EN14 299. pdf> (2009).

Schmidt et al., "Trackability, Crossability, and Pushability of Coronary Stent Systems—An Experimental Approach," Biomed Techn 47 (2002), Erg. 1, S. 124-126.

Schreiber, S.L. et al., "Atomic Structure of the Rapamycin Human Immunophilin FKBP-12 Complex," J. Am. Chem. Soc. 113:7433-7435 (1991).

Search Report from Singapore Application No. 2013054127 dated Jul. 26, 2017, 5 pages.

Sen et al., "Topical heparin: A promising agent for the prevention of tracheal stenosis in airway surgery," J. Surg. Res (Epub ahead of print) Feb. 21, 2009.

Serruys, Patrick et al., Comparison of Coronary-Artery Bypass Surgery and Stenting for the Treatment of Multivessel Disease, N. Engl. J. Med., 2001, vol. 344, No. 15, pp. 1117-1124.

Shekunov et al., "Crystallization Processes in Pharmaceutical Technology and Drup Delivery Design", Journal of Crystal Growth 211 (2000), pp. 122-136.

Simpson et al., "Hyaluronan and hyaluronidase in genitourinary tumors."Front Biosci. 13:5664-5680.

Smith et al., "Mitomycin C and the endoscopic treatment of laryngotracheal stenosis: Are two applications better than one?" Laryngoscope 119(2):272-283 (2009).

Sumathi et al., "Controlled comparison between betamethasone gel and lidocaine jelly applied over tracheal tube to reduce postoperative sore throat, cough, and hoarseness of voice," Br. J. Anaesth. 100(2):215-218 (2008).

Szabadits et al., "Flexibility and trackability of laser cut coronary stent systems," Acta of Bioengineering and Biomechanics 11 (3 ): 11-18 (2009).

Testa, B., "Prodrug research: futile or fertile?", Biochem. Pharmacal. Dec. 1, 2004;68(11):2097-2106.

Thalmann et al., "Long-term experience with bacillus Calmette-Guerin therapy of upper urinary tract transitional cell carcinoma in patients not eligible for surgery," J Urol. 168(4 Pt 1):1381-1385 (2002).

Torchlin, "Micellar Nanocarriers: Pharmaecutial Perspectives," Pharmaceutical Research, vol. 24, No. 1, Jan. 2007.

Unger et al., "Poly(ethylene carbonate): A thermoelastic and biodegradable biomaterial for drug eluting stent coatings?" Journal to Controlled Release, vol. 117, Issue 3, 312-321 (2007).

Verma et al., "Effect of surface properties on nanoparticle-cell interactions," Small 2010,6,No. 1, 12-21.

Iconomidou et al., "Secondary Structure of Chorion Proteins ofthe Teleosatan Fish Dentex dentex by ATR FR-IR and FT-Raman Spectroscopy," J. of Structural Biology, 132, 112-122(2000).

Jackson et al., "Characterization of perivascular poly(lactic-co-glycolic acid) films containing paclitaxel" Int. J. ofPhannaceutics, 283:97-109 (2004), incorporated in its entirety herein by reference.

Jensen et al., Neointimal hyperplasia after sirollmus-eluting and paclitaxel-eluting stend implantation in diabetic patients: the randomized diabetes and dmg eluting stent (DiabeDES) intravascular ultrasound trial. European heartjournal (29), pp. 2733-2741. Oct. 2, 2008. Retrieved from the Internet. Retrieved on [Jul. 17, 20 12]. URL: <http :/ /eurheartj .oxfordjournals.org/ content/2 9/22/2 73 3. full. pdf> entire document.

Jewell, et al., "Release ofPlasmid DNA from Intravascular Stents Coated with Ultrathin Multilayered Polyelectrolyte Films" Biomacromolecules. 7: 2483-2491 (2006).

Ji, et al., "96-Wellliquid-liquid extraction liquid chromatographytandem mass spectrometry method for the quantitative determination of ABT-578 in human blood samples" Journal of Chromatography B. 805:67-75 (2004).

Johns, H.E., J.R.Cunningham, Thomas, Charles C., Publisher, "The Physics of Radiology," 1983, Springfield, IL, pp. 133-143.

Joner et al. "Site-specific targeting of nanoparticle prednisolone reduces in-stent restenosis in a rabbit model of established atheroma," Arterioscler Thromb Vase Biol.2008 ;28: 1960-1966.

Jovanovic et al. "Stabilization of Proteins in Dry Powder Formulations Using Supercritical Fluid Technology," Pharm. Res. 2004; 21(11).

Ju, et al., Drug Release from Hydrophilic Matrices. 1. New Scaling Laws for Predicting Polymer and Drug Release Based on the Polymer Disentanglement Concentration and the Diffusion Layer, J. Pharm. Sci. vol. 84, No. 12, 1455-1463, Dec. 1995.

Kazemi et al., "The effect ofbetamethasone gel in reducing sore throat, cough, and hoarseness after laryngo-tracheal intubation," Middle East J. Anesthesiol. 19(1):197-204 (2007).

Kehinde et al., "Bacteriology of urinary tract infection associated with indwelling J ureteral stents," J. Endourol. 18(9):891-896 (2004).

Kelly et al., "Double-balloon trapping technique for embolization of a large widenecked superior cerebellar artery aneurysm: case report," Neurosurgery 63(4 Suppl 2):291-292 (2008).

Khan et al., "Chemistry and the new uses or Sucrose: How Important?" Pur and Appl. Chem (1984) 56:833-844.

Khan et al., "Enzymic Regioselective Hydrolysis of Peracctylated Reducing Disaccharides, Specifically at the Anomeric Centre: Intermediates for the Synthesis of Oligosaccharides." Tetrahedron Letters (1933) 34:7767.

Khan et al., Cyclic Acetals of 4,1',6'-Trichloro-4,1',6',-Trideoxy-Trideoxy-galacto-Sucrose and their Conversion into Methyl Ether Derivatives. Carb. ResCarb. Res. (1990) 198:275-283.

Khayankarn et al., "Adhesion and Permeability of Polyimide-Clay Nanocomposite Films for Protective Coatings," Journal of Applied Polymer Science, vol. 89,2875-2881 (2003).

Koh et al., "A novel nanostructured poly(lactic-co-glycolic-acid) multi-walled carbon nanotube composite for blood-contacting application. Thrombogenicity studies", Acta Biomaterials 5 (2009): 3411-3422.

Kurt et al., "Tandem oral, rectal and nasal administrations of Ankaferd Blood Stopper to control profuse bleeding leading to hemodynamic instability," Am J. Emerg. Med. 27(5):631, e1-2 (2009).

Labhasetwar et al., "Arterial uptake of biodegradable nanoparticles: effect of surface modifications," Journal of Pharmaceutical Sciences, vol. 87, No. 10, Oct. 1998; 1229-1234.

Lamm et al., "Bladder Cancer: Current Optimal Intravesical Treatment: Pharmacologic Treatment," Urologic Nursing 25 (5):323-6, 331-2 (Oct. 26, 2005).

(56) References Cited

OTHER PUBLICATIONS

Latella et al., "Nanoindentation hardness. Young's modulus, and creep behavior of organic-inorganic silica-based sol-gel thin films on copper," J Mater Res 23(9): 2357-2365 (2008).
Lawrance et al., "Rectal tacrolimus in the treatment of resistant ulcerative proctitis," Aliment. Pharmacol Ther. 28 (10):1214-20 (2008).
Lee et al., "Novel therapy for hearing loss: delivery of insulin-like growth factor 1 to the cochlea using gelatin hydrogel," Otol. Neurotol. 28(7):976-81 (2007).
Lehmann et al, "Drug treatment of nonviral sexually transmitted diseases: specific issues in adolescents," Paediatr Drugs 3(7):481-494 (2001).
Levit et al., "Supercritical C02 Assisted Electrospinning" J. of Supercritical Fluids, 329-333, vol. 31, Issue 3, (Nov. 2004).
Lewis, D. H., "Controlled Release of Bioactive Agents from Lactides/Glycolide Polymers" in Biodegradable Polymers as Drug Delivery Systems, Chasin, M. and Langer, R., eds., Marcel Decker (1990).
Luzzi, L.A.,, Microencapsulation, J. Pharm. Sciences, vol. 59, No. 10, Oct. 1970, pp. 1367-1376.
Machtle and Borger, Analytical Ultracentrifugation of Polymers and Nanoparticles, W. Machtle and L. Borger, (Springer) 2006, p. 41.
Mahoney et al., "Three-Dimensional Compositional Analysis ofDmg Eluting Stent Coatings Using Cluster Secondary Ion mass Spectrometry," Anal. Chem. , 80, 624-632 (2008).
Matsumoto, D, et al. Neointimal Coverage of Sirolimus-Eluting Stents at 6-month Follow-up: Evaluated by Optical Coherence Tomography, European Heart Journal, Nov. 29, 2006; 28:961-967.
McAlpine, J.B. et al., "Revised NMR Assignments for Rapamycine," J. Antibiotics 44:688-690 (1991).
Mehik et al., "Alfuzosin treatment for chronic prostatitis/chronic pelvic pain syndrome: a prospecitve, randomized, double-blind, placebo-controlled, pilot study," Urology 62(3):425-429 (2003).
Mei et al., "Local Delivery of Modified Paclitaxel-Loaded Poly(£-caprolactone)/Pluronic F68 Nanoparticles for Long-Term Inhibition of Hyperplasia," Journal of Pharmaceutical Sciences, vol. 98, No. 6, June 2009.
Melonakos et al., Treatment of low-grade bulbar transitional cell carcinoma with urethral instillation ormitmnycin C, Oct. 28, 2008, Adv. Urol., 173694 Epub.
Merrett et al., "Interaction of corneal cells with transforming growth factor beta2-modified poly dimethyl siloxane surfaces," Journal of Biomedical Materials Research, Part A, vol. 67A, No. 3, pp. 981-993 (2003).
Merriam-Webster Online Dictionary, obtained online at: <http://www.merriamwebster.com/dictionay/derivative>, downloaded Jan. 23, 2013.
Middleton and Tipton, Synthetic biodegradable polymers as orthopedic devises. Biomaterials 2000; 21:2335-46.
Minchin, "Nanomedicine: sizing up targets with nanoparticles," Nature Nanotechnology, vol. 33, Jan. 2008, 12-13.
Minoque et al., "Laryngotracheal topicalization with lidocaine before intubation decreases the incidence of coughing on emergence from general anesthesia," Anesth. Analg. 99(4):1253-1257 (2004).
Mishima et al. "Microencapsulation of Proteins by Rapid Expansion orSupercritical Solution with a Nonsolvent," AlChE J. 2000;46(4):857-65.
Mocco et al., "Pharos neurovascular intracranail stent: Elective use for a symptomatic stenosis refractory to medical therapy," Catheter Cardiovasc. Interv. (epub) (Mar. 2009).
Mollen et al., "Prevalence oftubo-ovarian abcess in adolescents diagnosed with pelvice inflammatory disease in a pediatric emergency department," Pediatr. Emerg. Care, 22(9): 621-625 (2006).
Moroni et al., "Post-ischemic brain damage:targeting PARP-1 within the ischemic neurovaschular units as a realistic avenue to stroke treatment," FEBS J. 276(1 ):36-45 (2009).
Muhlen et al., "Magnetic Resonance Imaging Contrast Agent Targeted Toward Activated Platelets Allows in Vivo Detection of Thrombosis and Monitoring of Thrombolysis Circulation," 118:258-267 (2008).

Murphy et al., "Chronic prostatitis: management strategies," Drugs 69(1): 71-84 (2009).
O'Donnell et al., "Salvage intravesical therapy with interferon-alpha 2b plus low dose bacillus Calmette-Guerin is effective in patients with superficial bladder cancer in whom bacillus calmette-guerin alone previously failed," Journ. Urology, 166(4): 1300-1304 (2001).
O'Neil et al., "Extracellular matrix binding mixed micelles for drug delivery applications," Journal of Controlled Release 137 (2009) 146-151.
Olbert et al., "In vitro and in vivo effects of CpG-Oligodeoxynucleotides (CpG-ODN) on murine transitional cell carcinoma and on the native murine urinary bladder wall," Anticancer Res. 29(6):2067-2076 (2009).
Ong and Serruys, "Technology Insight: an overview of research in drug-eluting stents," Nat. Clin. Parct. Cardiovas. Med. 2(12):647 (2005).
Park et al., Mechanisms of Mucoadhesion of Poly(acrylic Acid) Hydrogels, Pharm. Res. (1987) vol. 4, No. 6, pp. 457-464.
Abreu Filho et al., "Influence of metal alloy and the profile of coronary stents in patients with multivessel coronary disease," Clinics 2011 ;66(6):985-989.
Akoh et al., "One-Stage Synthesis of Raffinose Fatty Acid Polyesters. "Journal Food Science (1987) 52:1570.
Albert et al., "Antibiotics tor preventing recurrent urinary tract infection in nonpregnant women," Cochrane Database System Rev. 3, CD001209 (2004).
Au et al., "Methods to improve efficacy of intravesical mitomycin C: Results of a randomized phase III trial," Journal of the National Cancer Institute, 93 (8 ), 597-604 (2001).
Balss et al., "Quantitative spatial distribution of sirolumus and polymers in drugeluting stents using confocal Raman microscopy," J. of Biomedical Materials Research Part A, 258-270 (2007).
Belu el al., "Three-Dimensional Compositional Analysis of Drug Eluting Stent Coatings Using Cluster Secondary loan Mass Spectrometry," Anal. Chem. 80:624-632 (2008).
Belu, et al., "Chemical imaging of drug eluting coatings: Combining surface analysis and confocal Rama microscopy" J. Controlled Release 126: 111-121 (2008).
Boneff, "Topical Treatment of Chronic Prostatitis and Premature Ejaculation," International Urology and Nephrology 4(2):183-186 (1971).
Bookbinder et al., "A recombinant human enzyme for enhanced interstitial transport of therapeutics," Journal of Controlled Release 114:230-241 (2006).
Borchert et al., "Prevention and treatment of urinary tract infection with probiotics: Review and research perspective," Indian Journal Urol. 24(2): 139-144 (2008).
Brunstein et al., "Histamine, a vasoactive agent with vascular disrupting potential, improves tumour response by enhancing local drug delivery," British Journal of Cancer 95:1663-1669 (2006).
Bugay et al., "Raman Analysis of Pharmaceuticals," in "Applications of Vibrational Spectroscopy in Pharmaceutical Research and Development," Edited by Pivonka, D.E., Chalmers, J.M., Griffiths, P.R. (2007) Wiley and Sons.
Cadieux et al., "Use of triclosan-eluting ureteral stents in patients with long-term stents," J. Endourol (Epub) (Jun. 19, 2009).
Channon et al., "Nitric Oxide Synthase in Atherosclerosis and Vascular Injury: Insights from Experimental Gene Therapy," Arteriosclerosis, Thrombosis and Vascular Biology, 20(8):1873-1881 (2000).
Chen et al. Immobilization of heparin on a silicone surface through a heterobifunctional PEG spacer. Biomaterials. Dec. 2005;26(35):7418-24.
Chlopek et al., "The influence of carbon fibres on the resorption time and mechanical properties of the lactide-glycolide co-polymer", J. Biomater. Sci. Polymer Edn. vol. 18, No. 11, pp. 1355-1368 (2007).
Clair and Burks, "Thermoplastic/Melt-Processable Polyimides," NASA Conf. Pub. #2334 (1984), pp. 337-355.
Cohen et al., "Sintering Technique for the Preparation of Polymer Matrices for the Controlled Release of Macromolecules", Journal of Pharmaceutical Sciences, vol. 73, No. 8, 1984, p. 1034-1037.

(56) References Cited

OTHER PUBLICATIONS

Colombo et al. "Selection of Coronary Stents," Journal of the American College of Cardiology, vol. 40, No. 6, 2002, p. 1021-1033.
CRC Handbook of chemistry and physics. 71st ed. David R. Lide, Editor-in-Chief. Boca Raton, FL, CRC Press; 1990; 6-140.
Cyrus et al., "Intramural delivery of rapamycin with alphavbeta3-targeted paramagnetic nanoparticles inhibits stenosis after balloon injury," Arterioscler Thromb Vasc Biol 2008; 28:820-826.
David Grant, Crystallization Impact on the Nature and Properties of the Crystalline Product, 2003, SSCI, http://www.ssci-inc.com/Information/RecentPublications/ApplicationNotes/CrystallizationImpact/tabid/138/Default.aspx.
Derwent-ACC-No. 2004-108578 Abstracting 2004003077; Jan. 8, 2004; 3 pages.
Di Mario, C. et al., "Drug-Eluting Bioabsorbable Magnesium Stent," J. Interventional Cardiology 16(6):391-395 (2004).
Di Stasi et al., "Percutaneous sequential bacillus Calmette-Guerin and mitomycin C for panurothelial carcinomatosis," Can. J. Urol. 12(6):2895-2898 (2005).
Domb and Langer, "Polyanhydrides. I. Preparation of High Molecular Weight Polyanhydrides." J. Polym Sci. 25:3373-3386 (1987).
Domingo, C., et al., "Precipication of ultrafine organic crystals from the rapid expansion of supercritical solutions ove a capillary and a frit nozzle", J. Supercritical Fluids 10:39-55 (1997).
Dzik-Jurasz, "Molecular imaging in vivo: an introduction," The British Journal of Radiology, 76:S98-S109 (2003).
Electrostatic Process, Wiley Encyclopedia of Electrical and Electronics Engineering, John Wiley & Sons, Inc. 1999; 7:15-39.
Eltze et al., "Imidazoquinolinon, imidazopyridine, and isoquinolindione derivatives as novel and potent inhibitors of the poly (ADP-ribose) polymerase (PARP): a comparison with standard PARP inhibitors," Mol. Pharmacal 74(6):1587-1598 (2008).
Ettmayer et al. Lessons learned from marketed and investigational prodrugs. J Med Chem. May 6, 2004;47(10)2393-404.
European International Search Report of PCT/EP01/05736 dated Oct. 24, 2001.
Extended European Search Report for Application No. 14797966.0 dated Dec. 19, 2016.
Fibbi et al., "Chronic inflammation in the pathogenesis of benign prostatic hyperplasia," Int J Androl. Jun. 1, 2010;33(3)475-88.
Finn et al. Differential Response of Delayed Healing . . . Circulation vol. 112 (2005) 270-8.
Fleischmann et al., "High Expression of Gastrin-Releasing Peptide Receptors in the Vascular bed of Urinary Tract Cancers: Promising Candidates for Vascular Targeting Applications." Jun. 2009, Endocr. Relat. Cancer 16(2):623-33.
Froehlich et al., "Conscious sedation for gastroscopy: patient tolerance and cardiorespiratory parameters," Gastroenterology 108(3):697-704 (1995).
Fujiwara et al., "Insulin-like growth factor 1 treatment via hydrogels rescues cochlear hair cells from ischemic injury," Oct. 29, 2008, NeuroReport 19(16):1585-1588.
Fulton et al. Thin Fluoropolymer films and nanoparticle coatings from the rapid expansion of supercritical carbon dioxide solutions with electrostatic collection, Polymer Communication. 2003; 2627-3632.
Greco et al., Polymer Melting and Polymer Powder Sintering by Thermal Analysis, (Journal of Thermal Analysis and Calorimetry, vol. 72 (2003) (1167-1174.).
Green et al., "Simple conjugated polymer nanoparticles as biological labels," Proc Roy Soc A. published online Jun. 24, 2009 doi:10.1098/rspa.2009.0181.
Griebenow et al., "On Protein Denaturation in Aqueous-Organic Mixtures but not in Pure Organic Solvents," J. Am Chem Soc., vol. 118. No. 47, 11695-11700 (1996).
Hamilos et al., "Ditlerential etlects ofDmg-Eluting Stents on Local Endothelium-Dependent Coronary Vasomotion." JACC vol. 51, No. 22,2008, Endothelium and DES Jun. 3, 2008:2123-9.
Han, et al., "Studies of a Novel Human Thrombomodulin Immobilized Substrate: Surface Characterization and Anticoagulation Activity Evaluation." J. Biomater. Sci. Polymer Edn, 2001, 12 (10), 1075-1089.
Handschumacher, R.E. and Cheng, Y-C., Purine and Pyrimidine Antimetabolites, In: Cancer Medicine, pp. 712-732, Ch. XV1-2, 3rd Edition, Edited by J. Holland and E. Frei III (eds.), Lea and Febiger, 1992.
Hartmann et al., "Tubo-ovarian abscess in virginal adolescents: exposure or the underlying etiology," J. Pediatr Adolesc Gynecol, 22(3):313-16 (2009).
Hasegawa et al., "Nylong 6/Na-montmorillonite nanocomposites prepared by compounding Nylon 6 with Na-montmorillonite slurry," Polymer 44 (2003) 2933-2937.
Higuchi, Rate of Release of Medicaments from Ointment Bases Containing Drugs in Suspension, Journal of Pharmaceutical Sciences, vol. 50, No. 10, p. 874, Oct. 1961.
Hinds, WC. Aerosol Technology, Properties, Behavior and Measurement of Airborne Particles, Department of Environmental Health Sciences, Harvard University School of Public Health, Boston, Massachusetts. 1982; 283-314.
Hladik et al., "Can a topical microbicide prevent rectal HIV transmission?" PLoS Med. 5(8):e167 (2008).
Datenblatt NIRflex®der Firma Medinol, NIRFlex TM Premounted Coronary Stent System, Instructions for Use, Medinol Ingenuity for Life, Doc #912000012 Draft F, Oct. 8, 2003, 18 pages.
Stoeckel et al., "A survey of stent designs", Minimally Invasive Therapy & Allied Technologies, Jan. 2002, 11 (4), Seite 137-147.
Third Party Submission for Application No. JP2017-130734 dated Nov. 7, 2018, 2 pages.

COATED STENTS

CROSS-REFERENCE TO RELATED APPLICATIONS

This application is a continuation of U.S. patent application Ser. No. 12/751,902, filed Mar. 31, 2010, which claims the benefit of U.S. Provisional Application No. 61/165,880, filed Apr. 1, 2009, U.S. Provisional Application No. 61/212, 964, filed Apr. 17, 2009, and U.S. Provisional Application No. 61/243,955, filed Sep. 18, 2009. The contents of these applications are incorporated herein by reference in their entirety.

BACKGROUND OF THE INVENTION

The present invention relates to methods for forming stents comprising a bioabsorbable polymer and a pharmaceutical or biological agent in powder form onto a substrate.

It is desirable to have a drug-eluting stent with minimal physical, chemical and therapeutic legacy in the vessel after a proscribed period of time. This period of time is based on the effective healing of the vessel after opening the blockage by PCI/stenting (currently believed by leading clinicians to be 6-18 months).

It is also desirable to have drug-eluting stents of minimal cross-sectional thickness for (a) flexibility of deployment (b) access to small and large vessels (c) minimized intrusion into the vessel wall and blood.

BRIEF SUMMARY OF THE INVENTION

Provided herein is a coated stent, comprising a stent comprising a plurality of stent struts each having an abluminal surface, a luminal surface, and two sidewall surfaces; a coating comprising an active agent and a polymer; wherein the coating is substantially conformal to the abluminal, luminal, and sidewall surfaces of the struts of the stent.

In some embodiments, the coating adheres to the abluminal, luminal, and sidewall surfaces of the struts of the stent. In some embodiments, the coating adheres to at least 70% of the abluminal, luminal, and sidewall surfaces of the struts of the stent. In some embodiments, the coating adheres to at least 75% of the abluminal, luminal, and sidewall surfaces of the struts of the stent. In some embodiments, the coating adheres to at least 80% of the abluminal, luminal, and sidewall surfaces of the struts of the stent. In some embodiments, the coating adheres to at least 85% of the abluminal, luminal, and sidewall surfaces of the struts of the stent. In some embodiments, the coating adheres to at least 90% of the abluminal, luminal, and sidewall surfaces of the struts of the stent. In some embodiments, coating adheres to at least 95% of the abluminal, luminal, and sidewall surfaces of the struts of the stent. In some embodiments, coating adheres to at least 99% of the abluminal, luminal, and sidewall surfaces of the struts of the stent.

In some embodiments, adherence of the coating is measured by scanning electron microscopy of at least one cross section of a strut of the stent.

In some embodiments, adherence of the coating is measured by when the stent is in a collapsed condition. In some embodiments, adherence of the coating is measured by when the stent is in an expanded condition.

In some embodiments, the coating contacts the abluminal, luminal, and sidewall surfaces of the struts of the stent. In some embodiments, the coating contacts at least 70% of the abluminal, luminal, and sidewall surfaces of the struts of the stent. In some embodiments, the coating contacts at least 75% of the abluminal, luminal, and sidewall surfaces of the struts of the stent. In some embodiments, the coating contacts at least 80% of the abluminal, luminal, and sidewall surfaces of the struts of the stent. In some embodiments, the coating contacts at least 85% of the abluminal, luminal, and sidewall surfaces of the struts of the stent. In some embodiments, coating contacts at least 90% of the abluminal, luminal, and sidewall surfaces of the struts of the stent. In some embodiments, the coating contacts at least 95% of the abluminal, luminal, and sidewall surfaces of the struts of the stent. In some embodiments, the coating contacts at least 99% of the abluminal, luminal, and sidewall surfaces of the struts of the stent.

In some embodiments, contact of the coating to the stent surfaces is measured by scanning electron microscopy of at least one cross section of a strut of the stent.

In some embodiments, contact of the coating is measured by when the stent is in a collapsed condition. In some embodiments, contact of the coating is measured by when the stent is in an expanded condition.

In some embodiments, at least a part of the polymer is bioabsorbable, as further described herein.

In some embodiments, the active agent comprises at least one of a pharmaceutical agent and a biological agent as further described herein.

In some embodiments, the active agent comprises rapamycin.

In some embodiments, at least a part of the polymer is durable.

Provided herein is a coated stent, comprising a stent comprising a plurality of stent struts each having an abluminal surface, a luminal surface, and two sidewall surfaces; a coating comprising an active agent and a bioabsorbable polymer; wherein an abluminal coating thickness on the abluminal surface and a luminal coating thickness on the luminal surface are substantially the same.

In some embodiments, the abluminal coating thickness is at most 10% greater than the luminal coating thickness. In some embodiments, the abluminal coating thickness is at most 20% greater than the luminal coating thickness. In some embodiments, the abluminal coating thickness is at most 30% greater than the luminal coating thickness. In some embodiments, the abluminal coating thickness is at most 50% greater than the luminal coating thickness.

Provided herein is a coated stent, comprising a stent comprising a plurality of stent struts each having an abluminal surface, a luminal surface, and two sidewall surfaces; a coating comprising an active agent and a bioabsorbable polymer; wherein a ratio of an abluminal coating thickness on the abluminal surface to a luminal coating thickness on the luminal surface is at most 90:10.

In some embodiments, the ratio of abluminal coating thickness to luminal coating thickness is at most 50:50. In some embodiments, the ratio of abluminal coating thickness to luminal coating thickness is at most 65:35. In some embodiments, the ratio of abluminal coating thickness to luminal coating thickness is at most 70:30. In some embodiments, the ratio of abluminal coating thickness to luminal coating thickness is at most 75:25. In some embodiments, the ratio of abluminal coating thickness to luminal coating thickness is at most 80:20. In some embodiments, the ratio of abluminal coating thickness to luminal coating thickness is achieved during coating of the stent with the coating without a masking element. In some embodiments, the ratio of abluminal coating thickness to luminal coating thickness is achieved during coating of the stent with the coating without shielding the luminal surfaces. In some embodiments, the ratio of abluminal coating thickness to luminal coating thickness is achieved during coating of the stent with the coating wherein the stent is in a collapsed condition.

In some embodiments, the ratio of abluminal coating thickness to luminal coating thickness is achieved during coating of the stent with the coating wherein the stent is in an expanded condition.

In some embodiments, the ratio of abluminal coating thickness to luminal coating thickness is achieved during coating of the stent with the coating wherein the stent is in an intermediate condition. In some embodiments, an inner diameter of the stent in the intermediate condition is between an inner diameter of the stent in the expanded condition and an inner diameter of the stent in the collapsed condition. In some embodiments, an outer diameter of the stent in the intermediate condition is between an outer diameter of the stent in the expanded condition and an outer diameter of the stent in the collapsed condition.

In some embodiments, an average strut thickness of the stent when measured from the abluminal surface to the luminal surface is at most 140 microns. In some embodiments, an average strut thickness of the stent when measured from the abluminal surface to the luminal surface is at most 125 microns. In some embodiments, average strut thickness of the stent when measured from the abluminal surface to the luminal surface is at most 100 microns. In some embodiments, an average strut thickness of the stent when measured from the abluminal surface to the luminal surface is at most 90 microns. In some embodiments, an average strut thickness of the stent when measured from the abluminal surface to the luminal surface is at most 80 microns. In some embodiments, an average strut thickness of the stent when measured from the abluminal surface to the luminal surface is at most 75 microns. In some embodiments, an average strut thickness of the stent when measured from the abluminal surface to the luminal surface is about 65 microns. In some embodiments, an average strut thickness of the stent when measured from the abluminal surface to the luminal surface is about 63 microns. In some embodiments, an average strut thickness of the stent when measured from the abluminal surface to the luminal surface is 63 microns.

Provided herein is a method of preparing a stent comprising: providing the stent; depositing a plurality of layers on said stent to form said stent; wherein at least one of said layers comprises a drug-polymer coating wherein at least part of the drug of the drug-polymer coating is in crystalline form and the polymer of the drug-polymer coating is a bioabsorbable polymer.

Provided herein is a method of preparing a stent comprising: providing the stent; depositing a plurality of layers on said stent to form said stent; wherein at least one of said layers comprises a drug-polymer coating wherein at least part of the drug of the drug-polymer coating is in crystalline form and the polymer of the drug-polymer coating is a durable polymer.

In some embodiments, the drug and polymer are in the same layer; in separate layers or in overlapping layers.

In some embodiments, the stent is made of stainless steel.

In some embodiments, the stent is formed from a metal alloy.

In some embodiments, the stent is formed from a cobalt chromium alloy.

In some embodiments, the stent is formed from a material comprising the following percentages by weight: 0.05-0.15 C, 1.00-2.00 Mn, 0.040 Si, 0.030 P, 0.3 S, 19.00-21.00 Cr, 9.00-11.00 Ni, 14.00-16.00 W, 3.00 Fe, and Bal. Co.

In some embodiments, the stent is formed from a material comprising at most the following percentages by weight: about 0.025 maximum C, 0.15 maximum Mn, 0.15 maximum Si, 0.015 maximum P, 0.01 maximum S, 19.00-21.00 maximum Cr, 33-37 Ni, 9.0-10.5 Mo, 1.0 maximum Fe, 1.0 maximum Ti, and Bal. Co.

In some embodiments, the stent has a thickness of about 50% or less of a thickness of the coated stent. In some embodiments, the stent has a thickness of about 100 µm or less.

In some embodiments, the bioabsorbable polymer is selected from PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid).

Some embodiments comprise depositing 3 or more layers. Some embodiments comprise depositing 4 or more layers. Some embodiments comprise depositing 5 or more layers. Some embodiments comprise depositing 6 or more layers. Some embodiments comprise depositing 7 or more layers. Some embodiments comprise depositing 8 or more layers. Some embodiments comprise depositing 9 or more layers. Some embodiments comprise depositing 10, 20, 50, or 100 layers. Some embodiments comprise depositing at least one of: at least 10, at least 20, at least 50, and at least 100 layers. In some embodiments, the layers comprise alternate drug and polymer layers. In some embodiments, the drug layers are substantially free of polymer and the polymer layers are substantially free of drug.

In some embodiments, the active agent comprises a macrolide immunosuppressive (limus) drug. In some embodiments, the macrolide immunosuppressive drug comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycarbonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 4O—O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), and salts, derivatives, isomers, racemates, diastereoisomers, prodrugs, hydrate, ester, or analogs thereof.

In some embodiments, the macrolide immunosuppressive drug is at least 50% crystalline.

Some embodiments comprise depositing a plurality of layers on said stent to form said coronary stent comprises depositing polymer particles on said stent by an RESS process. In some embodiments, depositing a plurality of layers on said stent to form said coronary stent comprises depositing polymer particles on said stent in dry powder form.

Provided herein is a method of preparing a stent comprising: providing a stent; depositing a plurality of layers on said stent to form said stent; wherein at least one of said layers comprises a bioabsorbable polymer; wherein depositing each layer of said plurality of layers on said stent comprises the following steps: discharging at least one pharmaceutical agent and/or at least one active biological agent in dry powder form through a first orifice; discharging the at least one polymer in dry powder form through said first orifice or through a second orifice; depositing the polymer and pharmaceutical agent and/or active biological agent particles onto said stent, wherein an electrical potential is maintained between the stent and the polymer and pharmaceutical agent and/or active biological agent particles, thereby forming said layer; and sintering said layer under conditions that do not substantially modify the morphology of said pharmaceutical agent and/or the activity of said biological agent, wherein the coating is substantially conformal to each of an abluminal, luminal, and sidewall surface of the struts of the stent.

Provided herein is a method of preparing a stent comprising: providing a stent; depositing a plurality of layers on said stent to form said stent; wherein at least one of said layers comprises a bioabsorbable polymer; wherein depositing each layer of said plurality of layers on said stent comprises the following steps: discharging at least one pharmaceutical agent and/or at least one active biological agent in dry powder form through a first orifice; discharging the at least one polymer in dry powder form through said first orifice or through a second orifice; depositing the polymer and pharmaceutical agent and/or active biological agent particles onto said stent, wherein an electrical potential is maintained between the stent and the polymer and pharmaceutical agent and/or active biological agent particles, thereby forming said layer; and sintering said layer under conditions that do not substantially modify the morphology of said pharmaceutical agent and/or the activity of said biological agent, wherein an abluminal coating thickness on the abluminal surface and a luminal coating thickness on the luminal surface are substantially the same.

Provided herein is a method of preparing a stent comprising: providing a stent; depositing a plurality of layers on said stent to form said stent; wherein at least one of said layers comprises a bioabsorbable polymer; wherein depositing each layer of said plurality of layers on said stent comprises the following steps: discharging at least one pharmaceutical agent and/or at least one active biological agent in dry powder form through a first orifice; discharging the at least one polymer in dry powder form through said first orifice or through a second orifice; depositing the polymer and pharmaceutical agent and/or active biological agent particles onto said stent, wherein an electrical potential is maintained between the stent and the polymer and pharmaceutical agent and/or active biological agent particles, thereby forming said layer; and sintering said layer under conditions that do not substantially modify the morphology of said pharmaceutical agent and/or the activity of said biological agent, wherein a ratio of an abluminal coating thickness on the abluminal surface to a luminal coating thickness on the luminal surface is at most 90:10.

Some embodiments further comprise discharging a third dry powder comprising a second pharmaceutical agent in a therapeutically desirable morphology in dry powder form and/or active biological agent whereby a layer comprising at least two different pharmaceutical agents and/or active biological agents is deposited on said stent or at least two layers each comprising one of two different pharmaceutical agents and/or active biological agents are deposited on said stent.

In some embodiments, the stent is electrostatically charged.

In some embodiments, the stent is biodegradable.

In some embodiments, the therapeutically desirable morphology of said pharmaceutical agent is crystalline or semicrystalline.

In some embodiments, at least 50% of said pharmaceutical agent in powder form is crystalline or semicrystalline.

In some embodiments, the pharmaceutical agent comprises at least one drug.

In some embodiments, the at least one drug is selected from the group consisting of antirestenotic agents, antidiabetics, analgesics, anti-inflammatory agents, antirheumatics, antihypotensive agents, antihypertensive agents.

In some embodiments, the activity of said active biological agent is of therapeutic or prophylactic value.

In some embodiments, the biological agent is selected from the group comprising peptides, proteins, enzymes, nucleic acids, antisense nucleic acids, antimicrobials, vitamins, hormones, steroids, lipids, polysaccharides and carbohydrates.

In some embodiments, the activity of said active biological agent is influenced by the secondary, tertiary or quaternary structure of said active biological agent.

In some embodiments, the active biological agent possesses a secondary, tertiary or quaternary structure which is not substantially changed after the step of sintering said layer.

In some embodiments, the active biological agent further comprises a stabilizing agent.

In some embodiments, the sintering comprises treating said layer with a compressed gas, compressed liquid or supercritical fluid that is a non-solvent for both the polymer and the pharmaceutical and/or biological agents.

In some embodiments, the compressed gas, compressed liquid or supercritical fluid comprises carbon dioxide, isobutylene or a mixture thereof.

In some embodiments, the layer comprises a microstructure. In some embodiments, the microstructure comprises microchannels, micropores and/or microcavities. In some embodiments, the particles of said pharmaceutical agent and/or active biological agent are sequestered or encapsulated within said microstructure. In some embodiments, the microstructure is selected to allow controlled release of said pharmaceutical agent and/or active biological agent. In some embodiments, the microstructure is selected to allow sustained release of said pharmaceutical agent and/or active biological agent. In some embodiments, the microstructure is selected to allow continuous release of said pharmaceutical agent and/or active biological agent. In some embodiments, the microstructure is selected to allow pulsatile release of said pharmaceutical agent and/or active biological agent.

In some embodiments, the bioabsorbable polymer is selected from PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid).

Some embodiments of the methods comprise depositing 3 or more layers. Some embodiments comprise depositing 4 or more layers. Some embodiments comprise depositing 5 or more layers. Some embodiments comprise depositing 6 or more layers. Some embodiments comprise depositing 7 or more layers. Some embodiments comprise depositing 8 or more layers. Some embodiments comprise depositing 9 or more layers.

Some embodiments of the methods comprise depositing 10, 20, 50, or 100 layers. Some embodiments of the methods comprise depositing at least one of: at least 10, at least 20, at least 50, and at least 100 layers.

In some embodiments, the layers comprise alternate drug and polymer layers.

In some embodiments, the drug layers are substantially free of polymer and the polymer layers are substantially free of drug.

In some embodiments, the one or more active agents comprise a macrolide immunosuppressive (limus) drug.

In some embodiments, the macrolide immunosuppressive drug comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), and salts, derivatives, isomers, racemates, diastereoisomers, prodrugs, hydrate, ester, or analogs thereof.

Provided herein is a coated coronary stent, comprising: a stent; a first layer of bioabsorbable polymer; and a rapamycin-polymer coating comprising rapamycin and a second bioabsorbable polymer wherein at least part of rapamycin is in crystalline form and wherein the first polymer is a slow absorbing polymer and the second polymer is a fast absorbing polymer, and wherein the coating is substantially conformal to each of an abluminal, luminal, and sidewall surface of the struts of the stent.

Provided herein is a coated coronary stent, comprising: a stent; a first layer of bioabsorbable polymer; and a rapamycin-polymer coating comprising rapamycin and a second bioabsorbable polymer wherein at least part of rapamycin is in crystalline form and wherein the first polymer is a slow absorbing polymer and the second polymer is a fast absorbing polymer, and wherein an abluminal coating thickness on the abluminal surface and a luminal coating thickness on the luminal surface are substantially the same.

Provided herein is a coated coronary stent, comprising: a stent; a first layer of bioabsorbable polymer; and a rapamycin-polymer coating comprising rapamycin and a second bioabsorbable polymer wherein at least part of rapamycin is in crystalline form and wherein the first polymer is a slow absorbing polymer and the second polymer is a fast absorbing polymer, and wherein a ratio of an abluminal coating thickness on the abluminal surface to a luminal coating thickness on the luminal surface is at most 90:10

In some embodiments, the fast absorbing polymer is PLGA copolymer with a ratio of about 40:60 to about 60:40 and the slow absorbing polymer is a PLGA copolymer with a ration of about 70:30 to about 90:10.

INCORPORATION BY REFERENCE

All publications and patent applications mentioned in this specification are herein incorporated by reference to the same extent as if each individual publication or patent application were specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
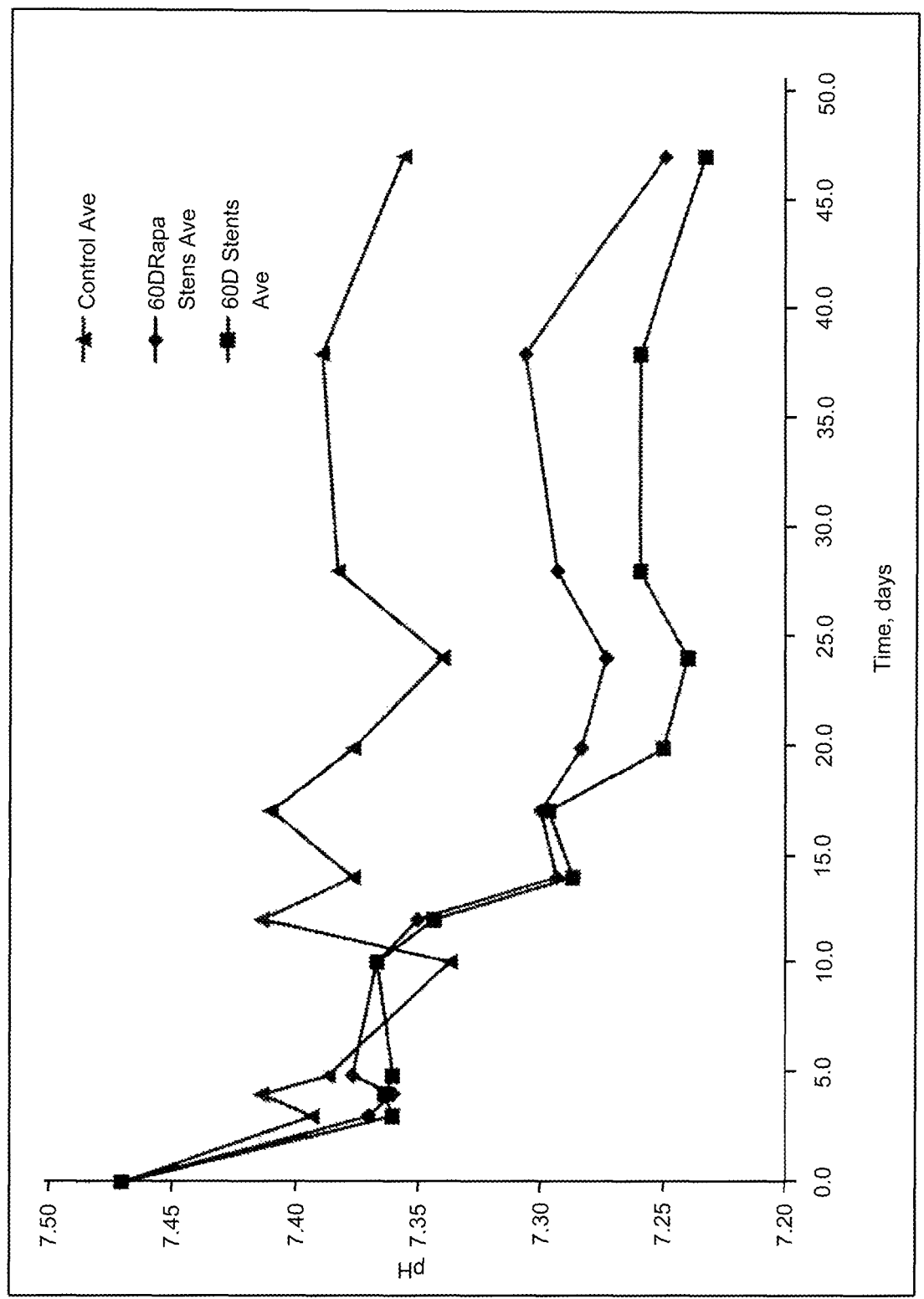
FIG. 1: Bioabsorbability testing of 50:50 PLGA-ester end group (MW~19 kD) polymer coating formulations on stents by determination of pH Changes with Polymer Film Degradation in 20% Ethanol/Phosphate Buffered Saline as set forth in Example 3 described herein.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

Definitions

As used in the present specification, the following words and phrases are generally intended to have the meanings as set forth below, except to the extent that the context in which they are used indicates otherwise.

"Substrate" as used herein, refers to any surface upon which it is desirable to deposit a coating comprising a polymer and a pharmaceutical or biological agent, wherein the coating process does not substantially modify the morphology of the pharmaceutical agent or the activity of the biological agent. Biomedical implants are of particular interest for the present invention; however the present invention is not intended to be restricted to this class of substrates. Those of skill in the art will appreciate alternate substrates that could benefit from the coating process described herein, such as pharmaceutical tablet cores, as part of an assay apparatus or as components in a diagnostic kit (e.g. a test strip).

"Biomedical implant" as used herein refers to any implant for insertion into the body of a human or animal subject, including but not limited to stents (e.g., vascular stents), electrodes, catheters, leads, implantable pacemaker, cardioverter or defibrillator housings, joints, screws, rods, ophthalmic implants, femoral pins, bone plates, grafts, anastomotic devices, perivascular wraps, sutures, staples, shunts for hydrocephalus, dialysis grafts, colostomy bag attachment devices, ear drainage tubes, leads for pace makers and implantable cardioverters and defibrillators, vertebral disks, bone pins, suture anchors, hemostatic barriers, clamps, screws, plates, clips, vascular implants, tissue adhesives and sealants, tissue scaffolds, various types of dressings (e.g., wound dressings), bone substitutes, intraluminal devices, vascular supports, etc.

The implants may be formed from any suitable material, including but not limited to organic polymers (including stable or inert polymers and biodegradable polymers), metals, inorganic materials such as silicon, and composites thereof, including layered structures with a core of one material and one or more coatings of a different material. Substrates made of a conducting material facilitate electrostatic capture. However, the invention contemplates the use of electrostatic capture in conjunction with substrate having low conductivity or which non-conductive. To enhance electrostatic capture when a non-conductive substrate is employed, the substrate is processed while maintaining a strong electrical field in the vicinity of the substrate. In some embodiments, however, no electrostatic capture is employed in applying a coating to the substrate. In some embodiments of the methods and/or devices provided herein, the substrate is not charged in the coating process. In some embodiments of the methods and/or devices provided herein, an electrical potential is not created between the substrate and the coating apparatus.

Subjects into which biomedical implants of the invention may be applied or inserted include both human subjects (including male and female subjects and infant, juvenile, adolescent, adult and geriatric subjects) as well as animal subjects (including but not limited to dog, cat, horse, monkey, etc.) for veterinary purposes and/or medical research.

In a preferred embodiment the biomedical implant is an expandable intraluminal vascular graft or stent (e.g., comprising a wire mesh tube) that can be expanded within a blood vessel by an angioplasty balloon associated with a catheter to dilate and expand the lumen of a blood vessel, such as described in U.S. Pat. No. 4,733,665 to Palmaz Shaz.

"Active agent" as used herein refers to any pharmaceutical agent or active biological agent as described herein.

"Pharmaceutical agent" as used herein refers to any of a variety of drugs or pharmaceutical compounds that can be used as active agents to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the pharmaceutical agents of the invention may also comprise two or more drugs or pharmaceutical compounds. Pharmaceutical agents, include but are not limited to antirestenotic agents, antidiabetics, analgesics, anti-inflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phytopharmaceuticals, chemotherapeutic agents and amino acids. Examples of suitable active ingredients are acarbose, antigens, beta-receptor blockers, non-steroidal anti-inflammatory drugs [NSAIDs], cardiac glycosides, acetylsalicylic acid, virustatics, aclarubicin, acyclovir, cisplatin, actinomycin, alpha- and beta-sympatomimetics, (dmeprazole, allopurinol, alprostadil, prostaglandins, amantadine, ambroxol, amlodipine, methotrexate, S-aminosalicylic acid, amitriptyline, amoxicillin, anastrozole, atenolol, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, cromoglicic acid, coumarin and coumarin derivatives, cysteine, cytarabine, cyclophosphamide, ciclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxorubizin, doxylamine, dapiprazole, benzodiazepines, diclofenac, glycoside antibiotics, desipramine, econazole, ACE inhibitors, enalapril, ephedrine, epinephrine, epoetin and epoetin derivatives, morphinans, calcium antagonists, irinotecan, modafinil, orlistat, peptide antibiotics, phenytoin, riluzoles, risedronate, sildenafil, topiramate, macrolide antibiotics, oestrogen and oestrogen derivatives, progestogen and progestogen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, fluarizine, fluorouracil, fluoxetine, flurbiprofen, ibuprofen, flutamide, fluvastatin, follitropin, formoterol, fosfomicin, furosemide, fusidic acid, gallopamil, ganciclovir, gemfibrozil, gentamicin, ginkgo, Saint John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenytoin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, roxatidine, roxithromycin, ruscogenin, rutoside and rutoside derivatives, sabadilla, salbutamol, salmeterol, scopolamine, selegiline, sertaconazole, sertindole, sertralion, silicates, sildenafil, simvastatin, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulfasalazine, sulpiride, sultamicillin, sultiam, sumatriptan, suxamethonium chloride, tacrine, tacrolimus, taliolol, tamoxifen, taurolidine, tazarotene, temazepam, teniposide, tenoxicam, terazosin, terbinafine, terbutaline, terfenadine, terlipressin, tertatolol, tetracyclins, teryzoline, theobromine, theophylline, butizine, thiamazole, phenothiazines, thiotepa, tiagabine, tiapride, propionic acid derivatives, ticlopidine, timolol, tinidazole, tioconazole, tioguanine, tioxolone, tiropramide, tizanidine, tolazoline, tolbutamide, tolcapone, tolnaftate, tolperisone, topotecan, torasemide, antioestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutine, tulobuterol, tyramine, tyrothricin, urapidil, ursodeoxycholic acid, chenodeoxycholic acid, valaciclovir, valproic acid, vancomycin, vecuronium chloride, Viagra, venlafaxine, verapamil, vidarabine, vigabatrin, viloazine, vinblastine, vincamine, vincristine, vindesine, vinorelbine, vinpocetine, viquidil, warfarin, xantinol nicotinate, xipamide, zafirlukast, zalcitabine, zidovudine, zolmitriptan, zolpidem, zoplicone, zotipine, clotrimazole, amphotericin B, caspofungin, or voriconazole, resveratrol, PARP-1 inhibitors (including imidazoquinolinone, imidazpyridine, and isoquinolindione, tissue plasminogen activator (tPA), melagatran, lanoteplase, reteplase, staphylokinase, streptokinase, tenecteplase, urokinase, and the like. See, e.g., U.S. Pat. No. 6,897,205; see also U.S. Pat. Nos. 6,838,528; 6,497,729.

Examples of therapeutic agents employed in conjunction with the invention include, rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-[(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy]ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), and salts, derivatives, isomers, racemates, diastereoisomers, prodrugs, hydrate, ester, or analogs thereof.

The active ingredients may, if desired, also be used in the form of their pharmaceutically acceptable salts or derivatives (meaning salts which retain the biological effectiveness and properties of the compounds of this invention and which are not biologically or otherwise undesirable), and in the case of chiral active ingredients it is possible to employ both optically active isomers and racemates or mixtures of diastereoisomers.

In some embodiments, a pharmaceutical agent is at least one of: Acarbose, acetylsalicylic acid, acyclovir, allopurinol, alprostadil, prostaglandins, amantadine, ambroxol, amlodipine, S-aminosalicylic acid, amitriptyline, atenolol, azathioprine, balsalazide, beclomethasone, betahistine, bezafibrate, diazepam and diazepam derivatives, budesonide, bufexamac, buprenorphine, methadone, calcium salts, potassium salts, magnesium salts, candesartan, carbamazepine, captopril, cetirizine, chenodeoxycholic acid, theophylline and theophylline derivatives, trypsins, cimetidine, clobutinol, clonidine, cotrimoxazole, codeine, caffeine, vitamin D and derivatives of vitamin D, colestyramine, cromoglicic acid, coumarin and coumarin derivatives, cysteine, ciclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxylamine, benzodiazepines, diclofenac, desipramine, econazole, ACE inhibitors, enalapril, ephedrine, epinephrine, epoetin and epoetin derivatives, morphinans, calcium antagonists, modafinil, orlistat, peptide antibiotics, phenytoin, riluzoles, risedronate, sildenafil, topiramate, estrogen, progestogen and progestogen derivatives, testosterone derivatives, androgen and androgen derivatives, ethenzamide, etofenamate, etofibrate, fenofibrate, etofylline, famciclovir, famotidine, felodipine, fentanyl, fenticonazole, gyrase inhibitors, fluconazole, fluarizine, fluoxetine, flurbiprofen, ibuprofen, fluvastatin, follitropin, formoterol, fosfomicin, furosemide, fusidic acid, gallopamil, ganciclovir, gemfibrozil, ginkgo, Saint John's wort, glibenclamide, urea derivatives as oral antidiabetics, glucagon, glucosamine and glucosamine derivatives, glutathione, glycerol and glycerol derivatives, hypothalamus hormones, guanethidine, halofantrine, haloperidol, heparin (and derivatives), hyaluronic acid, hydralazine, hydrochlorothiazide (and derivatives), salicylates, hydroxyzine, imipramine, indometacin, indoramine, insulin, iodine and iodine derivatives, isoconazole, isoprenaline, glucitol and glucitol derivatives, itraconazole, ketoprofen, ketotifen, lacidipine, lansoprazole, levodopa, levomethadone, thyroid hormones, lipoic acid (and derivatives), lisinopril, lisuride, lofepramine, loperamide, loratadine, maprotiline, mebendazole, mebeverine, meclozine, mefenamic acid, mefloquine, meloxicam, mepindolol, meprobamate, mesalazine, mesuximide, metamizole, metformin, methylphenidate, metixene, metoprolol, metronidazole, mianserin, miconazole, minoxidil, misoprostol, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, novamine sulfone, noscapine, nystatin, olanzapine, olsalazine, omeprazole, omoconazole, oxaceprol, oxiconazole, oxymetazoline, pantoprazole, paracetamol (acetaminophen), paroxetine, penciclovir, pentazocine, pentifylline, pentoxifylline, perphenazine, pethidine, plant extracts, phenazone, pheniramine, barbituric acid derivatives, phenylbutazone, pimozide, pindolol, piperazine, piracetam, pirenzepine, piribedil, piroxicam, pramipexole, pravastatin, prazosin, procaine, promazine, propiverine, propranolol, propyphenazone, protionamide, proxyphylline, quetiapine, quinapril, quinaprilat, ramipril, ranitidine, reproterol, reserpine, ribavirin, risperidone, ritonavir, ropinirole, roxatidine, ruscogenin, rutoside (and derivatives), sabadilla, salbutamol, salmeterol, scopolamine, selegiline, sertaconazole, sertindole, sertralion, silicates, simvastatin, sitosterol, sotalol, spaglumic acid, spirapril, spironolactone, stavudine, streptomycin, sucralfate, sufentanil, sulfasalazine, sulpiride, sultiam, sumatriptan, suxamethonium chloride, tacrine, tacrolimus, taliolol, taurolidine, temazepam, tenoxicam, terazosin, terbinafine, terbutaline, terfenadine, terlipressin, tertatolol, teryzoline, theobromine, butizine, thiamazole, phenothiazines, tiagabine, tiapride, propionic acid derivatives, ticlopidine, timolol, tinidazole, tioconazole, tioguanine, tioxolone, tiropramide, tizanidine, tolazoline, tolbutamide, tolcapone, tolnaftate, tolperisone, topotecan, torasemide, tramadol, tramazoline, trandolapril, tranylcypromine, trapidil, trazodone, triamcinolone derivatives, triamterene, trifluperidol, trifluridine, trimipramine, tripelennamine, triprolidine, trifosfamide, tromantadine, trometamol, tropalpin, troxerutine, tulobuterol, tyramine, tyrothricin, urapidil, valaciclovir, valproic acid, vancomycin, vecuronium chloride, Viagra, venlafaxine, verapamil, vidarabine, vigabatrin, viloazine, vincamine, vinpocetine, viquidil, warfarin, xantinol nicotinate, xipamide, zafirlukast, zalcitabine, zidovudine, zolmitriptan, zolpidem, zoplicone, zotipine, amphotericin B, caspofungin, voriconazole, resveratrol, PARP-1 inhibitors (including imidazoquinolinone, imidazpyridine, and isoquinolindione, tissue plasminogen activator (tPA), melagatran, lanoteplase, reteplase, staphylokinase, streptokinase, tenecteplase, urokinase, 40-O-(2-Hydroxyethyl)rapamycin (everolimus), biolimus (biolimus A9), 40-O-Benzyl-rapamycin, 40-O-(4'-Hydroxymethyl) benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E, 4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy) hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido) ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), abciximab (ReoPro), eptifibatide, tirofiban, prasugrel, clopidogrel, dipyridamole, cilostazol, VEGF, heparan sulfate, chondroitin sulfate, elongated "RGD" peptide binding domain, CD34 antibodies, cerivastatin, etorvastatin, losartan, valartan, erythropoietin, rosiglitazone, pioglitazone, mutant protein Apo A1 Milano, adiponectin, (NOS) gene therapy, glucagon-like peptide 1, atorvastatin, and atrial natriuretic peptide (ANP), lidocaine, tetracaine, dibucaine, hyssop, ginger, turmeric, Arnica montana, helenalin, cannabichromene, rofecoxib, hyaluronidase, and salts, derivatives, isomers, racemates, diastereoisomers, prodrugs, hydrate, ester, or analogs thereof.

The pharmaceutical agents may, if desired, also be used in the form of their pharmaceutically acceptable salts or derivatives (meaning salts which retain the biological effectiveness and properties of the compounds of this invention and which are not biologically or otherwise undesirable), and in the case of chiral active ingredients it is possible to employ both optically active isomers and racemates or mixtures of diastereoisomers. As well, the pharmaceutical agent may include a prodrug, a hydrate, an ester, a derivative or analogs of a compound or molecule.

The pharmaceutical agent may be an antibiotic agent, as described herein.

The pharmaceutical agent may be a chemotherapeutic agent, as described herein.

The pharmaceutical agent may be an antithrombotic agent, as described herein.

The pharmaceutical agent may be a statin, as described herein.

The pharmaceutical agent may be an angiogenesis promoter, as described herein.

The pharmaceutical agent may be a local anesthetic, as described herein.

The pharmaceutical agent may be an anti-inflammatory agent, as described herein.

A "pharmaceutically acceptable salt" may be prepared for any pharmaceutical agent having a functionality capable of forming a salt, for example an acid or base functionality. Pharmaceutically acceptable salts may be derived from organic or inorganic acids and bases. The term "pharmaceutically-acceptable salts" in these instances refers to the relatively non-toxic, inorganic and organic base addition salts of the pharmaceutical agents.

"Prodrugs" are derivative compounds derivatized by the addition of a group that endows greater solubility to the compound desired to be delivered. Once in the body, the prodrug is typically acted upon by an enzyme, e.g., an esterase, amidase, or phosphatase, to generate the active compound.

An "anti-cancer agent", "anti-tumor agent" or "chemotherapeutic agent" refers to any agent useful in the treatment of a neoplastic condition. There are many chemotherapeutic agents available in commercial use, in clinical evaluation and in pre-clinical development that are useful in the devices and methods of the present invention for treatment of cancers.

Chemotherapeutic agents may comprise any chemotherapeutic agent described, for example, in Ser. No. 12/729,580, filed Mar. 23, 2010, incorporated by reference herein in its entirety.

An "antibiotic agent," as used herein, is a substance or compound that kills bacteria (i.e., is bacteriocidal) or inhibits the growth of bacteria (i.e., is bacteriostatic). Antibiotics that can be used in the devices and methods of the present invention include, but are not limited to, amikacin, amoxicillin, gentamicin, kanamycin, neomycin, netilmicin, paromomycin, tobramycin, geldanamycin, herbimycin, carbacephem (loracarbef), ertapenem, doripenem, imipenem, cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, clarithromycin, clavulanic acid, clindamycin, teicoplanin, azithromycin, dirithromycin, erythromycin, troleandomycin, telithromycin, aztreonam, ampicillin, azlocillin, bacampicillin, carbenicillin, cloxacillin, dicloxacillin, flucloxacillin, mezlocillin, meticillin, nafcillin, norfloxacin, oxacillin, penicillin G, penicillin V, piperacillin, pvampicillin, pivmecillinam, ticarcillin, bacitracin, colistin, polymyxin B, ciprofloxacin, enoxacin, gatifloxacin, levofloxacin, lomefloxacin, moxifloxacin, ofloxacin, trovafloxacin, grepafloxacin, sparfloxacin, afenide, prontosil, sulfacetamide, sulfamethizole, sulfanilimide, sulfamethoxazole, sulfisoxazole, trimethoprim, trimethoprim-sulfamethoxazole, demeclocycline, doxycycline, oxytetracycline, tetracycline, arsphenamine, chloramphenicol, lincomycin, ethambutol, fosfomycin, furazolidone, isoniazid, linezolid, mupirocin, nitrofurantoin, platensimycin, pyrazinamide, quinupristin/dalfopristin, rifampin, thiamphenicol, rifampicin, minocycline, sultamicillin, sulbactam, sulphonamides, mitomycin, spectinomycin, spiramycin, roxithromycin, and meropenem.

Antibiotics can also be grouped into classes of related drugs, for example, aminoglycosides (e.g., amikacin, gentamicin, kanamycin, neomycin, netilmicin, paromomycin, streptomycin, tobramycin), ansamycins (e.g., geldanamycin, herbimycin), carbacephem (loracarbef) carbapenems (e.g., ertapenem, doripenem, imipenem, meropenem), first generation cephalosporins (e.g., cefadroxil, cefazolin, cefalotin, cefalexin), second generation cephalosporins (e.g., cefaclor, cefamandole, cefoxitin, cefprozil, cefuroxime), third generation cephalosporins (e.g., cefixime, cefdinir, cefditoren, cefoperazone, cefotaxime, cefpodoxime, ceftazidime, ceftibuten, ceftizoxime, ceftriaxone), fourth generation cephalosporins (e.g., cefepime), fifth generation cephalosporins (e.g., ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, bacampicillin, carbenicillin, cloxacillin, dicloxacillin, flucloxacillin, mezlocillin, meticillin, nafcillin, oxacillin, penicillins G and V, piperacillin, pvampicillin, pivmecillinam, ticarcillin), polypeptides (e.g., bacitracin, colistin, polymyxin B), quinolones (e.g., ciprofloxacin, enoxacin, gatifloxacin, levofloxacin, lomefloxacin, moxifloxacin, norfloxacin, ofloxacin, trovafloxacin, grepafloxacin, sparfloxacin, trovafloxacin), sulfonamides (e.g., afenide, prontosil, sulfacetamide, sulfamethizole, sulfanilimide, sulfasalazine, sulfamethoxazole, sulfisoxazole, trimethoprim, trimethoprim-sulfamethoxazole), tetracyclines (e.g., demeclocycline, doxycycline, minocycline, oxytetracycline, tetracycline).

"Anti-thrombotic agents" are contemplated for use in the methods of the invention in adjunctive therapy for treatment of coronary stenosis. The use of anti-platelet drugs, e.g., to prevent platelet binding to exposed collagen, is contemplated for anti-restenotic or anti-thrombotic therapy. Anti-platelet agents include "GpIIb/IIIa inhibitors" (e.g., abciximab, eptifibatide, tirofiban, RheoPro) and "ADP receptor blockers" (prasugrel, clopidogrel, ticlopidine). Particularly useful for local therapy are dipyridamole, which has local vascular effects that improve endothelial function (e.g., by causing local release of t-PA, that will break up clots or prevent clot formation) and reduce the likelihood of platelets and inflammatory cells binding to damaged endothelium, and cAMP phosphodiesterase inhibitors, e.g., cilostazol, that could bind to receptors on either injured endothelial cells or bound and injured platelets to prevent further platelet binding.

"Statins" (e.g., cerivastatin, etorvastatin), which can have endothelial protective effects and improve progenitor cell function, are contemplated for use in embodiments of methods and/or devices provided herein. Other drugs that have demonstrated some evidence to improve EPC colonization, maturation or function and are contemplated for use in the methods of the invention are angiotensin converting enzyme inhibitors (ACE-I, e.g., Captopril, Enalapril, and Ramipril), Angiotensin II type I receptor blockers (AT-II-blockers, e.g., losartan, valartan), peroxisome proliferator-activated receptor gamma (PPAR-γ) agonists, and erythropoietin. The PPAR-γ agonists like the glitazones (e.g., rosiglitazone, pioglitazone) can provide useful vascular effects, including the ability to inhibit vascular smooth muscle cell proliferation, and have anti-inflammatory functions, local antithrombotic properties, local lipid lowing effects, and can inhibit matrix metalloproteinase (MMP) activity so as to stabilize vulnerable plaque.

"Angiogenesis promoters" can be used for treating reperfusion injury, which can occur when severely stenotic arteries, particular chronic total occlusions, are opened. Angiogenesis promoters are contemplated for use in embodiments of methods and/or devices provided herein. Myocardial cells downstream from a blocked artery will downregulate the pathways normally used to prevent damage from oxygen free radicals and other blood borne toxins. A sudden infusion of oxygen can lead to irreversible cell damage and death. Drugs developed to prevent this phenomenon can be effective if provided by sustained local delivery. Neurovascular interventions can particularly benefit from this treatment strategy. Examples of pharmacological agents potentially useful in preventing reperfusion injury are glucagon-like peptide 1, erythropoietin, atorvastatin, and atrial natriuretic peptide (ANP). Other angiogenesis promoters have been described, e.g., in U.S. Pat. No. 6,284,758, "Angiogenesis promoters and angiogenesis potentiators," U.S. Pat. No. 7,462,593, "Compositions and methods for promoting angiogenesis," and U.S. Pat. No. 7,456,151, "Promoting angiogenesis with netrin1 polypeptides."

"Local anesthetics" are substances which inhibit pain signals in a localized region. Examples of such anesthetics include procaine, lidocaine, tetracaine and dibucaine. Local anesthetics are contemplated for use in embodiments of methods and/or devices provided herein.

"Anti-inflammatory agents" as used herein refer to agents used to reduce inflammation. Anti-inflammatory agents useful in the devices and methods of the invention include, but are not limited to: aspirin, ibuprofen, naproxen, hyssop, ginger, turmeric, helenalin, cannabichromene, rofecoxib, celecoxib, paracetamol (acetaminophen), sirolimus (rapamycin), dexamethasone, dipyridamole, alfuzosin, statins, and glitazones. Anti-inflammatory agents are contemplated for use in embodiments of methods and/or devices provided herein.

Anti-inflammatory agents can be classified by action. For example, glucocorticoids are steroids that reduce inflammation or swelling by binding to cortisol receptors. Non-steroidal anti-inflammatory drugs (NSAIDs), alleviate pain by acting on the cyclooxygenase (COX) enzyme. COX synthesizes prostaglandins, causing inflammation. A cannabinoid, cannabichromene, present in the cannabis plant, has been reported to reduce inflammation. Newer COX-inhibitors, e.g., rofecoxib and celecoxib, are also anti-inflammatory agents. Many anti-inflammatory agents are also analgesics (painkillers), including salicylic acid, paracetamol (acetaminophen), COX-2 inhibitors and NSAIDs. Also included among analgesics are, e.g., narcotic drugs such as morphine, and synthetic drugs with narcotic properties such as tramadol.

Other anti-inflammatory agents useful in the methods of the present invention include sirolimus (rapamycin) and dexamethasone. Stents coated with dexamethasone were reported to be useful in a particular subset of patients with exaggerated inflammatory disease evidenced by high plasma C-reactive protein levels. Because both restenosis and atherosclerosis have such a large inflammatory component, anti-inflammatories remain of interest with regard to local therapeutic agents. In particular, the use of agents that have anti-inflammatory activity in addition to other useful pharmacologic actions is contemplated. Examples include dipyridamole, statins and glitazones. Despite an increase in cardiovascular risk and systemic adverse events reported with use of cyclooxygenase (COX)-inhibitors (e.g., celocoxib), these drugs can be useful for short term local therapy.

"Stability" as used herein in refers to the stability of the drug in a polymer coating deposited on a substrate in its final product form (e.g., stability of the drug in a coated stent). The term stability will define 5% or less degradation of the drug in the final product form.

"Active biological agent" as used herein refers to a substance, originally produced by living organisms, that can be used to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the active biological agents of the invention may also comprise two or more active biological agents or an active biological agent combined with a pharmaceutical agent, a stabilizing agent or chemical or biological entity. Although the active biological agent may have been originally produced by living organisms, those of the present invention may also have been synthetically prepared, or by methods combining biological isolation and synthetic modification. By way of a non-limiting example, a nucleic acid could be isolated form from a biological source, or prepared by traditional techniques, known to those skilled in the art of nucleic acid synthesis. Furthermore, the nucleic acid may be further modified to contain non-naturally occurring moieties. Non-limiting examples of active biological agents include peptides, proteins, enzymes, glycoproteins, nucleic acids (including deoxyribonucleotide or ribonucleotide polymers in either single or double stranded form, and unless otherwise limited, encompasses known analogues of natural nucleotides that hybridize to nucleic acids in a manner similar to naturally occurring nucleotides), antisense nucleic acids, fatty acids, antimicrobials, vitamins, hormones, steroids, lipids, polysaccharides, carbohydrates and the like. They further include, but are not limited to, antirestenotic agents, antidiabetics, analgesics, anti-inflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phytopharmaceuticals and chemotherapeutic agents. Preferably, the active biological agent is a peptide, protein or enzyme, including derivatives and analogs of natural peptides, proteins and enzymes.

"Activity" as used herein refers to the ability of a pharmaceutical or active biological agent to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). Thus the activity of a pharmaceutical or active biological agent should be of therapeutic or prophylactic value.

"Secondary, tertiary and quaternary structure" as used herein are defined as follows. The active biological agents of the present invention will typically possess some degree of secondary, tertiary and/or quaternary structure, upon which the activity of the agent depends. As an illustrative, non-limiting example, proteins possess secondary, tertiary and quaternary structure. Secondary structure refers to the spatial arrangement of amino acid residues that are near one another in the linear sequence. The α-helix and the β-strand are elements of secondary structure. Tertiary structure refers to the spatial arrangement of amino acid residues that are far apart in the linear sequence and to the pattern of disulfide bonds. Proteins containing more than one polypeptide chain exhibit an additional level of structural organization. Each polypeptide chain in such a protein is called a subunit. Quaternary structure refers to the spatial arrangement of subunits and the nature of their contacts. For example hemoglobin consists of two α and two β chains. It is well known that protein function arises from its conformation or three dimensional arrangement of atoms (a stretched out polypeptide chain is devoid of activity). Thus one aspect of the present invention is to manipulate active biological agents, while being careful to maintain their conformation, so as not to lose their therapeutic activity.

"Polymer" as used herein, refers to a series of repeating monomeric units that have been cross-linked or polymerized. Any suitable polymer can be used to carry out the present invention. It is possible that the polymers of the invention may also comprise two, three, four or more different polymers. In some embodiments, of the invention only one polymer is used. In some preferred embodiments a combination of two polymers are used. Combinations of polymers can be in varying ratios, to provide coatings with differing properties. Polymers useful in the devices and methods of the present invention include, for example, stable or inert polymers, organic polymers, organic-inorganic copolymers, inorganic polymers, bioabsorbable, bioresorbable, resorbable, degradable, and biodegradable polymers. Those of skill in the art of polymer chemistry will be familiar with the different properties of polymeric compounds.

In some embodiments, the coating comprises a polymer. In some embodiments, the active agent comprises a polymer. In some embodiments, the polymer comprises at least one of polyalkyl methacrylates, polyalkylene-co-vinyl acetates, polyalkylenes, polyurethanes, polyanhydrides, aliphatic polycarbonates, polyhydroxyalkanoates, silicone containing polymers, polyalkyl siloxanes, aliphatic polyesters, polyglycolides, polylactides, polylactide-co-glycolides, poly(e-caprolactone)s, polytetrahalooalkylenes, polystyrenes, poly (phosphasones), copolymers thereof, and combinations thereof.

Examples of polymers that may be used in the present invention include, but are not limited to polycarboxylic acids, cellulosic polymers, proteins, polypeptides, polyvinylpyrrolidone, maleic anhydride polymers, polyamides, polyvinyl alcohols, polyethylene oxides, glycosaminoglycans, polysaccharides, polyesters, aliphatic polyesters, polyurethanes, polystyrenes, copolymers, silicones, silicone containing polymers, polyalkyl siloxanes, polyorthoesters, polyanhydrides, copolymers of vinyl monomers, polycarbonates, polyethylenes, polypropytenes, polylactic acids, polylactides, polyglycolic acids, polyglycolides, polylactide-co-glycolides, polycaprolactones, poly(e-caprolactone) s, polyhodroxybutyrate valerates, polyacrylamides, polyethers, polyurethane dispersions, polyacrylates, acrylic latex dispersions, polyacrilic acid, polyalkyl methacrylates, polyalkylene-co-vinyl acetates, polyalkylenes, aliphatic polycarbonates polyhydroxyalkanoates, polytetrahalooalkylenes, poly(phosphasones), polytetrahalooalkylenes, poly (phosphasones), and mixtures, combinations, and copolymers thereof.

The polymers of the present invention may be natural or synthetic in origin, including gelatin, chitosan, dextrin, cyclodextrin, Poly(urethanes), Poly(siloxanes) or silicones, Poly(acrylates) such as [rho]oly(methyl methacracylate), poly(butyl methacrylate), and Poly(2-hydroxy ethyl methacrylate), Poly(vinyl alcohol) Poly(olefins) such as poly (ethylene), [rho]oly(isoprene), halogenated polymers such as Poly(tetrafluoroethylene)—and derivatives and copolymers such as those commonly sold as Teflon® producs, Poly(vinylidine fluoride), Poly(vinyl acetate), Poly(vinyl pyrrolidone), Poly(acrylic acid), Polyacrylamide, Poly(ethylene-co-vinyl acetate), Poly(ethylene glycol), Poly(propylene glycol), Poly(methacrylic acid); etc.

Examples of polymers that may be used in the present invention include, but are not limited to polycarboxylic acids, cellulosic polymers, proteins, polypeptides, polyvinylpyrrolidone, maleic anhydride polymers, polyamides, polyvinyl alcohols, polyethylene oxides, glycosaminoglycans, polysaccharides, polyesters, aliphatic polyesters, polyurethanes, polystyrenes, copolymers, silicones, silicone containing polymers, polyalkyl siloxanes, polyorthoesters, polyanhydrides, copolymers of vinyl monomers, polycarbonates, polyethylenes, polypropytenes, polylactic acids, polylactides, polyglycolic acids, polyglycolides, polylactide-co-glycolides, polycaprolactones, poly(e-caprolactone) s, polyhydroxybutyrate valerates, polyacrylamides, polyethers, polyurethane dispersions, polyacrylates, acrylic latex dispersions, polyacrylic acid, polyalkyl methacrylates, polyalkylene-co-vinyl acetates, polyalkylenes, aliphatic polycarbonates polyhydroxyalkanoates, polytetrahalooalkylenes, poly(phosphasones), polytetrahalooalkylenes, poly (phosphasones), and mixtures, combinations, and copolymers thereof.

The polymers of the present invention may be natural or synthetic in origin, including gelatin, chitosan, dextrin, cyclodextrin, Poly(urethanes), Poly(siloxanes) or silicones, Poly(acrylates) such as [rho]oly(methyl methacrylate), poly (butyl methacrylate), and Poly(2-hydroxy ethyl methacrylate), Poly(vinyl alcohol) Poly(olefins) such as poly(ethylene), [rho]oly(isoprene), halogenated polymers such as Poly (tetrafluoroethylene)—and derivatives and copolymers such as those commonly sold as Teflon® products, Poly(vinylidine fluoride), Poly(vinyl acetate), Poly(vinyl pyrrolidone), Poly(acrylic acid), Polyacrylamide, Poly(ethylene-co-vinyl acetate), Poly(ethylene glycol), Poly(propylene glycol), Poly(methacrylic acid); etc.

Suitable polymers also include absorbable and/or resorbable polymers including the following, combinations, copolymers and derivatives of the following: Polylactides (PLA), Polyglycolides (PGA), PolyLactide-co-glycolides (PLGA), Polyanhydrides, Polyorthoesters, Poly(N-(2-hydroxypropyl) methacrylamide), Poly(l-aspartamide), including the derivatives DLPLA—poly(dl-lactide); LPLA—poly(l-lactide); PDO—poly(dioxanone); PGA-TMC poly(glycolide-co-trimethylene carbonate); PGA-LPLA—poly(l-lactide-co-glycolide); PGA-DLPLA—poly(dl-lactide-co-glycolide); LPLA-DLPLA—poly(l-lactide-co-dl-lactide); and PDO-PGA-TMC—poly(glycolide-co-trimethylene carbonate-co-dioxanone), and combinations thereof.

"Copolymer" as used herein refers to a polymer being composed of two or more different monomers. A copolymer may also and/or alternatively refer to random, block, graft, copolymers known to those of skill in the art.

As used herein, the term "durable polymer" refers to a polymer that is not bioabsorbable (and/or is not bioerodible, and/or is not biodegradable, and/or is not bioresorbable) and is, thus biostable. In some embodiments, the device comprises a durable polymer. The polymer may include a cross-linked durable polymer. Example biocompatible durable polymers include, but are not limited to: polyester, aliphatic polyester, polyanhydride, polyethylene, polyorthoester, polyphosphazene, polyurethane, polycarbonate urethane, aliphatic polycarbonate, silicone, a silicone containing polymer, polyolefin, polyamide, polycaprolactam, polyamide, polyvinyl alcohol, acrylic polymer, acrylate, polystyrene, epoxy, polyethers, cellulosics, expanded polytetrafluoroethylene, phosphorylcholine, polyethyleneyerphthalate, polymethylmethavrylate, poly(ethylmethacrylate/n-butylmethacrylate), parylene C, polyethylene-co-vinyl acetate, polyalkyl methacrylates, polyalkylene-co-vinyl acetate, polyalkylene, polyalkyl siloxanes, polyhydroxyalkanoate, polyfluoroalkoxyphasphazine, poly(styrene-b-isobutylene-b-styrene), poly-butyl methacrylate, poly-bytadiene, and blends, combinations, homopolymers, condensation polymers, alternating, block, dendritic, cross-linked, and copolymers thereof. The polymer may include a thermoset material. The polymer may provide strength for the coated implantable medical device. The polymer may provide durability for the coated implantable medical device. The coatings and coating methods provided herein provide substantial protection from these by establishing a multi-layer coating which can be bioabsorbable or durable or a combination thereof, and which can both deliver active agents and provide elasticity and radial strength for the vessel in which it is delivered.

The terms "bioabsorbable," "biodegradable," "bioerodible," "bioresorbable," and "resorbable" are art-recognized synonyms. These terms are used herein interchangeably. Bioabsorbable polymers typically differ from non-bioabsorbable polymers or "durable" polymers in that the former may be absorbed (e.g.; degraded) during use. In certain embodiments, such use involves in vivo use, such as in vivo therapy, and in other certain embodiments, such use involves in vitro use. In general, degradation attributable to biodegradability involves the degradation of a bioabsorbable polymer into its component subunits, of digestion, e.g., by a biochemical process, of the polymer into smaller, non-polymeric subunits. In certain embodiments, biodegradation may occur by enzymatic mediation, degradation in the presence of water (hydrolysis) and/or other chemical species in the body, or both. The bioabsorbability of a polymer may be shown in-vitro as described herein or by methods known to one of skill in the art. An in-vitro test for bioabsorbability of a polymer does not require living cells or other biologic materials to show bioabsorption properties (e.g. degradation, digestion). Thus, resorbtion, resorption, absorption, absorption, erosion may also be used synonymously with the terms "bioabsorbable," "biodegradable," "bioerodible," and "bioresorbable." Mechanisms of degradation of a bioabsorbable polymer may include, but are not limited to, bulk degradation, surface erosion, and combinations thereof.

As used herein, the term "biodegradation" encompasses both general types of biodegradation. The degradation rate of a biodegradable polymer often depends in part on a variety of factors, including the chemical identity of the linkage responsible for any degradation, the molecular weight, crystallinity, biostability, and degree of cross-linking of such polymer, the physical characteristics (e.g., shape and size) of the implant, and the mode and location of administration. For example, the greater the molecular weight, the higher the degree of crystallinity, and/or the greater the biostability, the biodegradation of any bioabsorbable polymer is usually slower "Biocompatible" as used herein, refers to any material that does not cause injury or death to the animal or induce an adverse reaction in an animal when placed in intimate contact with the animal's tissues. Adverse reactions include for example inflammation, infection, fibrotic tissue formation, cell death, or thrombosis. The terms "biocompatible" and "biocompatibility" when used herein are art-recognized and mean that the referent is neither itself toxic to a host (e.g., an animal or human), nor degrades (if it degrades) at a rate that produces byproducts (e.g., monomeric or oligomeric subunits or other byproducts) at toxic concentrations, causes inflammation or irritation, or induces an immune reaction in the host. It is not necessary that any subject composition have a purity of 100% to be deemed biocompatible. Hence, a subject composition may comprise 99%, 98%, 97%, 96%, 95%, 90% 85%, 80%, 75% or even less of biocompatible agents, e.g., including polymers and other materials and excipients described herein, and still be biocompatible. "Non-biocompatible" as used herein, refers to any material that may cause injury or death to the animal or induce an adverse reaction in the animal when placed in intimate contact with the animal's tissues. Such adverse reactions are as noted above, for example.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner the sample is degraded in 1 M NaOH at 37 degrees C. until complete degradation is observed. The solution is then neutralized with 1 M HCl. About 200 microliters of various concentrations of the degraded sample products are placed in 96-well tissue culture plates and seeded with human gastric carcinoma cells (GT3TKB) at 104/well density. The degraded sample products are incubated with the GT3TKB cells for 48 hours. The results of the assay may be plotted as % relative growth vs. concentration of degraded sample in the tissue-culture well. In addition, polymers and formulations of the present invention may also be evaluated by well-known in vivo tests, such as subcutaneous implantations in rats to confirm that they do not cause significant levels of irritation or inflammation at the subcutaneous implantation sites.

"Therapeutically desirable morphology" as used herein refers to the gross form and structure of the pharmaceutical agent, once deposited on the substrate, so as to provide for optimal conditions of ex vivo storage, in vivo preservation and/or in vivo release. Such optimal conditions may include, but are not limited to increased shelf life, increased in vivo stability, good biocompatibility, good bioavailability or modified release rates. Typically, for the present invention, the desired morphology of a pharmaceutical agent would be crystalline or semi-crystalline or amorphous, although this may vary widely depending on many factors including, but not limited to, the nature of the pharmaceutical agent, the disease to be treated/prevented, the intended storage conditions for the substrate prior to use or the location within the body of any biomedical implant. Preferably at least 10%, 20%, 30%, 40%, 50%, 60%, 70%, 80%, 90% or 100% of the pharmaceutical agent is in crystalline or semi-crystalline form.

"Stabilizing agent" as used herein refers to any substance that maintains or enhances the stability of the biological agent. Ideally these stabilizing agents are classified as Generally Regarded As Safe (GRAS) materials by the US Food and Drug Administration (FDA). Examples of stabilizing agents include, but are not limited to carrier proteins, such as albumin, gelatin, metals or inorganic salts. Pharmaceutically acceptable excipient that may be present can further be found in the relevant literature, for example in the Handbook of Pharmaceutical Additives: An International Guide to More Than 6000 Products by Trade Name, Chemical, Function, and Manufacturer; Michael and Irene Ash (Eds.); Gower Publishing Ltd.; Aldershot, Hampshire, England, 1995.

"Layer" as used herein refers to a material covering a surface or forming an overlying part or segment. Two different layers may have overlapping portions whereby material from one layer may be in contact with material from another layer. Contact between materials of different layers can be measured by determining a distance between the materials. For example, Raman spectroscopy may be employed in identifying materials from two layers present in close proximity to each other.

While layers defined by uniform thickness and/or regular shape are contemplated herein, several embodiments described herein relate to layers having varying thickness and/or irregular shape. Material of one layer may extend into the space largely occupied by material of another layer. For example, in a coating having three layers formed in sequence as a first polymer layer, a pharmaceutical agent layer and a second polymer layer, material from the second polymer layer which is deposited last in this sequence may extend into the space largely occupied by material of the pharmaceutical agent layer whereby material from the second polymer layer may have contact with material from the pharmaceutical layer. It is also contemplated that material from the second polymer layer may extend through the entire layer largely occupied by pharmaceutical agent and contact material from the first polymer layer.

It should be noted however that contact between material from the second polymer layer (or the first polymer layer) and material from the pharmaceutical agent layer (e.g.; a pharmaceutical agent crystal particle or a portion thereof) does not necessarily imply formation of a mixture between the material from the first or second polymer layers and material from the pharmaceutical agent layer. In some embodiments, a layer may be defined by the physical three-dimensional space occupied by crystalline particles of a pharmaceutical agent (and/or biological agent). It is contemplated that such layer may or may not be continuous as physical space occupied by the crystal particles of pharmaceutical agents may be interrupted, for example, by polymer material from an adjacent polymer layer. An adjacent polymer layer may be a layer that is in physical proximity to be pharmaceutical agent particles in the pharmaceutical agent layer. Similarly, an adjacent layer may be the layer formed in a process step right before or right after the process step in which pharmaceutical agent particles are deposited to form the pharmaceutical agent layer.

As described herein, material deposition and layer formation provided herein are advantageous in that the pharmaceutical agent remains largely in crystalline form during the entire process. While the polymer particles and the pharmaceutical agent particles may be in contact, the layer formation process is controlled to avoid formation of a mixture between the pharmaceutical agent particles the polymer particles during formation of a coated device.

In some embodiments, the coating comprises a plurality of layers deposited on said substrate, wherein at least one of the layers comprises the active agent. In some embodiments, at least one of the layers comprises a polymer. In some embodiments, the polymer is bioabsorbable. In some embodiments, the polymer is a durable polymer. In some embodiments, the active agent and the polymer are in the same layer, in separate layers, or form overlapping layers. In some embodiments, the plurality of layers comprise five layers deposited as follows: a first polymer layer, a first active agent layer, a second polymer layer, a second active agent layer and a third polymer layer.

In some embodiments of the methods and/or devices provided herein, the coating comprises a plurality of layers deposited on said substrate, wherein at least one of the layers comprises the active agent. In some embodiments, at least one of the layers comprises a polymer. In some embodiments, the polymer is bioabsorbable. In some embodiments, the polymer is a durable polymer. In some embodiments, the active agent and the polymer are in the same layer, in separate layers, or form overlapping layers. In some embodiments, the coating comprises a plurality of layers deposited on said substrate, wherein at least one of the layers comprises the pharmaceutical agent. In some embodiments, the pharmaceutical agent and the polymer are in the same layer, in separate layers, or form overlapping layers. In some embodiments, the plurality of layers comprise five layers deposited as follows: a first polymer layer, a first active agent layer, a second polymer layer, a second active agent layer and a third polymer layer. In some embodiments, the plurality of layers comprise five layers deposited as follows: a first polymer layer, a first pharmaceutical agent layer, a second polymer layer, a second pharmaceutical agent layer and a third polymer layer. In some embodiments, the plurality of layers comprise five layers deposited as follows: a first polymer layer, a first active biological agent layer, a second polymer layer, a second active biological agent layer and a third polymer layer.

"Compressed fluid" as used herein refers to a fluid of appreciable density (e.g., >0.2 g/cc) that is a gas at standard temperature and pressure. "Supercritical fluid", "near-critical fluid", "near-supercritical fluid", "critical fluid", "densified fluid" or "densified gas" as used herein refers to a compressed fluid under conditions wherein the temperature is at least 80% of the critical temperature of the fluid and the pressure is at least 50% of the critical pressure of the fluid.

Examples of substances that demonstrate supercritical or near critical behavior suitable for the present invention include, but are not limited to carbon dioxide, isobutylene, ammonia, water, methanol, ethanol, ethane, propane, butane, pentane, dimethyl ether, xenon, sulfur hexafluoride, halogenated and partially halogenated materials such as chlorofluorocarbons, hydrochlorofluorocarbons, hydrofluorocarbons, perfluorocarbons (such as perfluoromethane and perfuoropropane, chloroform, trichloro-fluoromethane, dichloro-difluoromethane, dichloro-tetrafluoroethane) and mixtures thereof.

"Sintering" as used herein refers to the process by which parts of the matrix or the entire polymer matrix becomes continuous (e.g., formation of a continuous polymer film). As discussed below, the sintering process is controlled to produce a fully conformal continuous matrix (complete sintering) or to produce regions or domains of continuous coating while producing voids (discontinuities) in the matrix. As well, the sintering process is controlled such that some phase separation is obtained between polymer different polymers (e.g., polymers A and B) and/or to produce phase separation between discrete polymer particles. Through the sintering process, the adhesions properties of the coating are improved to reduce flaking of detachment of the coating from the substrate during manipulation in use. As described below, in some embodiments, the sintering process is controlled to provide incomplete sintering of the polymer matrix. In embodiments involving incomplete sintering, a polymer matrix is formed with continuous domains, and voids, gaps, cavities, pores, channels or, interstices that provide space for sequestering a therapeutic agent which is released under controlled conditions. Depending on the nature of the polymer, the size of polymer particles and/or other polymer properties, a compressed gas, a densified gas, a near critical fluid or a super-critical fluid may be employed. In one example, carbon dioxide is used to treat a substrate that has been coated with a polymer and a drug, using dry powder and RESS electrostatic coating processes. In another example, isobutylene is employed in the sintering process. In other examples a mixture of carbon dioxide and isobutylene is employed.

When an amorphous material is heated to a temperature above its glass transition temperature, or when a crystalline material is heated to a temperature above a phase transition temperature, the molecules comprising the material are more mobile, which in turn means that they are more active and thus more prone to reactions such as oxidation. However, when an amorphous material is maintained at a temperature below its glass transition temperature, its molecules are substantially immobilized and thus less prone to reactions. Likewise, when a crystalline material is maintained at a temperature below its phase transition temperature, its molecules are substantially immobilized and thus less prone to reactions. Accordingly, processing drug components at mild conditions, such as the deposition and sintering conditions described herein, minimizes cross-reactions and degradation of the drug component. One type of reaction that is minimized by the processes of the invention relates to the ability to avoid conventional solvents which in turn minimizes autoxidation of drug, whether in amorphous, semi-crystalline, or crystalline form, by reducing exposure thereof to free radicals, residual solvents and autoxidation initiators.

"Rapid Expansion of Supercritical Solutions" or "RESS" as used herein involves the dissolution of a polymer into a compressed fluid, typically a supercritical fluid, followed by rapid expansion into a chamber at lower pressure, typically near atmospheric conditions. The rapid expansion of the supercritical fluid solution through a small opening, with its accompanying decrease in density, reduces the dissolution capacity of the fluid and results in the nucleation and growth of polymer particles. The atmosphere of the chamber is maintained in an electrically neutral state by maintaining an isolating "cloud" of gas in the chamber. Carbon dioxide or other appropriate gas is employed to prevent electrical charge is transferred from the substrate to the surrounding environment.

"Bulk properties" properties of a coating including a pharmaceutical or a biological agent that can be enhanced through the methods of the invention include for example: adhesion, smoothness, conformality, thickness, and compositional mixing.

"Electrostatically charged" or "electrical potential" or "electrostatic capture" or "e-" as used herein refers to the collection of the spray-produced particles upon a substrate that has a different electrostatic potential than the sprayed particles. Thus, the substrate is at an attractive electronic potential with respect to the particles exiting, which results in the capture of the particles upon the substrate. i.e. the substrate and particles are oppositely charged, and the particles transport through the fluid medium of the capture vessel onto the surface of the substrate is enhanced via electrostatic attraction. This may be achieved by charging the particles and grounding the substrate or conversely charging the substrate and grounding the particles, or by some other process, which would be easily envisaged by one of skill in the art of electrostatic capture.

Means for creating the bioabsorbable polymer(s)+drug(s) matrix on the stent-form—forming the final device:
  Spray coat the stent-form with drug and polymer as is done in Miceli process (e-RESS, e-DPC, compressed-gas sintering).
  Perform multiple and sequential coatingsintering steps where different materials may be deposited in each step, thus creating a laminated structure with a multitude of thin layers of drug(s), polymer(s) or drug+polymer that build the final stent.
  Perform the deposition of polymer(s)+drug(s) laminates with the inclusion of a mask on the inner (luminal) surface of the stent. Such a mask could be as simple as a non-conductive mandrel inserted through the internal diameter of the stent form. This masking could take place prior to any layers being added, or be purposefully inserted after several layers are deposited continuously around the entire stent-form.

Another advantage of the present invention is the ability to create a stent with a controlled (dialed-in) drug-elution profile. Via the ability to have different materials in each layer of the laminate structure and the ability to control the location of drug(s) independently in these layers, the method enables a stent that could release drugs at very specific elution profiles, programmed sequential and/or parallel elution profiles. Also, the present invention allows controlled elution of one drug without affecting the elution of a second drug (or different doses of the same drug).

The embodiments incorporating a stent form or stent provide the ability to radiographically monitor the stent in deployment. In an alternative embodiment, the inner-diameter of the stent can be masked (e.g. by a non-conductive mandrel). Such masking would prevent additional layers from being on the interior diameter (abluminal) surface of the stent. The resulting configuration may be desirable to provide preferential elution of the drug toward the vessel wall (luminal surface of the stent) where the therapeutic effect of anti-restenosis is desired, without providing the same antiproliferative drug(s) on the abluminal surface, where they may retard healing, which in turn is suspected to be a cause of late-stage safety problems with current DESs.

The present invention provides numerous advantages. The invention is advantageous allows for employing a platform combining layer formation methods based on compressed fluid technologies; electrostatic capture and sintering methods. The platform results in drug eluting stents having enhanced therapeutic and mechanical properties. The invention is particularly advantageous in that it employs optimized laminate polymer technology. In particular, the present invention allows the formation of discrete layers of specific drug platforms.

Conventional processes for spray coating stents require that drug and polymer be dissolved in solvent or mutual solvent before spray coating can occur. The platform provided herein the drugs and polymers are coated on the stent in discrete steps, which can be carried out simultaneously or alternately. This allows discrete deposition of the active agent (e.g.; a drug) within a polymer matrix thereby allowing the placement of more than one drug on a single medical device with or without an intervening polymer layer. For example, the present platform provides a dual drug eluting stent.

Some of the advantages provided by the subject invention include employing compressed fluids (e.g., supercritical fluids, for example E-RESS based methods); solvent free deposition methodology; a platform that allows processing at lower temperatures thereby preserving the qualities of the active agent and the polymer matrix; the ability to incorporate two, three or more drugs while minimizing deleterious effects from direct interactions between the various drugs and/or their excipients during the fabrication and/or storage of the drug eluting stents; a dry deposition; enhanced adhesion and mechanical properties of the layers on the stent; precision deposition and rapid batch processing; and ability to form intricate structures.

In one embodiment, the present invention provides a multi-drug delivery platform which produces strong, resilient and flexible drug eluting stents including an anti-restenosis drug (e.g.; a limus or taxol) and anti-thrombosis drug (e.g.; heparin or an analog thereof) and well characterized bioabsorbable polymers. The drug eluting stents provided herein minimize potential for thrombosis, in part, by reducing or totally eliminating thrombogenic polymers and reducing or totally eliminating residual drugs that could inhibit healing.

The platform provides optimized delivery of multiple drug therapies for example for early stage treatment (restenosis) and late-stage (thrombosis).

The platform also provides an adherent coating which enables access through tortuous lesions without the risk of the coating being compromised.

Another advantage of the present platform is the ability to provide highly desirable eluting profiles.

Advantages of the invention include the ability to reduce or completely eliminate potentially thrombogenic polymers as well as possibly residual drugs that may inhibit long term healing. As well, the invention provides advantageous stents having optimized strength and resilience if coatings which in turn allows access to complex lesions and reduces or completely eliminates delamination. Laminated layers of bioabsorbable polymers allow controlled elution of one or more drugs.

The platform provided herein reduces or completely eliminates shortcoming that have been associated with conventional drug eluting stents. For example, the platform provided herein allows for much better tuning of the period of time for the active agent to elute and the period of time necessary for the polymer matrix to resorb thereby minimizing thrombosis and other deleterious effects associate with poorly controlled drug release.

The present invention provides several advantages which overcome or attenuate the limitations of current technology for bioabsorbable stents. For example, an inherent limitation of conventional bioabsorbable polymeric materials relates to the difficulty in forming to a strong, flexible, deformable (e.g. balloon deployable) stent with low profile. The polymers generally lack the strength of high-performance metals. The present invention overcomes these limitations by creating a laminate structure in the essentially polymeric stent. Without wishing to be bound by any specific theory or analogy, the increased strength provided by the stents of the invention can be understood by comparing the strength of plywood vs. the strength of a thin sheet of wood.

Embodiments of the invention involving a thin metallic stent-stent provide advantages including the ability to overcome the inherent elasticity of most polymers. It is generally difficult to obtain a high rate (e.g., 100%) of plastic deformation in polymers (compared to elastic deformation where the materials have some 'spring back' to the original shape).

Again, without wishing to be bound by any theory, the central metal stent (that would be too small and weak to serve as a stent itself) would act like wires inside of a plastic, deformable stent, basically overcoming any 'elastic memory' of the polymer.

Provided herein is a coated stent, comprising a stent comprising a plurality of stent struts each having an abluminal surface, a luminal surface, and two sidewall surfaces; a coating comprising an active agent and a polymer; wherein the coating is substantially conformal to the abluminal, luminal, and sidewall surfaces of the struts of the stent. Provided herein is a coated stent, comprising a stent comprising a plurality of stent struts each having an abluminal surface, a luminal surface, and two sidewall surfaces; a coating comprising an active agent and a polymer; wherein the coating is substantially conformal to at least one of the abluminal, the luminal, and the sidewall surfaces of the struts of the stent. When viewing a cross section of a stent and looking at the struts of the stent along the stent's longitudinal axis, the abluminal surface of a strut is the surface on the side of the wall of a lumen and/or on the side of the strut that is away from the lumen where the luminal surface is the surface on the lumen side of the cavity or channel within the tube or hollow organ (e.g. vessel). The sidewalls extend between the luminal and the abluminal surfaces.

In some embodiments, a coating that is substantially conformal to the surface of the strut of the stent is a coating that adheres to at least 70% the given surface of the strut (whether the abluminal, the luminal, a sidewall surface, or a combination thereof). In some embodiments, the coating adheres to the abluminal, luminal, and sidewall surfaces of the struts of the stent. In some embodiments, the coating adheres to at least 70% of at least one of: the abluminal surface, the luminal surface, and the sidewall surfaces of the struts of the stent. In some embodiments, the coating adheres to at least 70% of the abluminal, luminal, and sidewall surfaces of the struts of the stent. In some embodiments, the coating adheres to at least 75% of at least one of: the abluminal surface, the luminal surface, and the sidewall surfaces of the struts of the stent. In some embodiments, the coating adheres to at least 75% of the abluminal, luminal, and sidewall surfaces of the struts of the stent. In some embodiments, the coating adheres to at least 80% of at least one of: the abluminal surface, the luminal surface, and the sidewall surfaces of the struts of the stent. In some embodiments, the coating adheres to at least 80% of the abluminal, luminal, and sidewall surfaces of the struts of the stent. In some embodiments, the coating adheres to at least 85% of at least one of: the abluminal surface, the luminal surface, and the sidewall surfaces of the struts of the stent. In some embodiments, the coating adheres to at least 85% of the abluminal, luminal, and sidewall surfaces of the struts of the stent. In some embodiments, the coating adheres to at least 90% of at least one of: the abluminal surface, the luminal surface, and the sidewall surfaces of the struts of the stent. In some embodiments, the coating adheres to at least 90% of the abluminal, luminal, and sidewall surfaces of the struts of the stent. In some embodiments, the coating adheres to at least 95% of at least one of: the abluminal surface, the luminal surface, and the sidewall surfaces of the struts of the stent. In some embodiments, coating adheres to at least 95% of the abluminal, luminal, and sidewall surfaces of the struts of the stent. In some embodiments, the coating adheres to at least 99% of at least one of: the abluminal surface, the luminal surface, and the sidewall surfaces of the struts of the stent. In some embodiments, coating adheres to at least 99% of the abluminal, luminal, and sidewall surfaces of the struts of the stent.

In some embodiments, adherence of the coating is measured by scanning electron microscopy of at least one cross section of a strut of the stent.

In some embodiments, adherence of the coating is measured when the stent is in a collapsed condition. In some embodiments, adherence of the coating is measured by when the stent is in an expanded condition.

In some embodiments, a coating that is substantially conformal to the surface of the strut of the stent is a coating that contacts at least 70% the given surface of the strut (whether the abluminal, the luminal, a sidewall surface, or a combination thereof). In some embodiments, the coating contacts the abluminal, luminal, and sidewall surfaces of the struts of the stent. In some embodiments, the coating contacts at least 70% of at least one of: the abluminal surface, the luminal surface, and the sidewall surfaces of the struts of the stent. In some embodiments, the coating contacts at least 70% of the abluminal, luminal, and sidewall surfaces of the struts of the stent. In some embodiments, the coating contacts at least 75% of at least one of: the abluminal surface, the luminal surface, and the sidewall surfaces of the struts of the stent. In some embodiments, the coating contacts at least 75% of the abluminal, luminal, and sidewall surfaces of the struts of the stent. In some embodiments, the coating contacts at least 80% of at least one of: the abluminal surface, the luminal surface, and the sidewall surfaces of the struts of the stent. In some embodiments, the coating contacts at least 80% of the abluminal, luminal, and sidewall surfaces of the struts of the stent. In some embodiments, the coating contacts at least 85% of at least one of: the abluminal surface, the luminal surface, and the sidewall surfaces of the struts of the stent. In some embodiments, the coating contacts at least 85% of the abluminal, luminal, and sidewall surfaces of the struts of the stent. In some embodiments, the coating contacts at least 90% of at least one of: the abluminal surface, the luminal surface, and the sidewall surfaces of the struts of the stent. In some embodiments, the coating contacts at least 90% of the abluminal, luminal, and sidewall surfaces of the struts of the stent. In some embodiments, the coating contacts at least 95% of at least one of: the abluminal surface, the luminal surface, and the sidewall surfaces of the struts of the stent. In some embodiments, the coating contacts at least 95% of the abluminal, luminal, and sidewall surfaces of the struts of the stent. In some embodiments, the coating contacts at least 99% of at least one of: the abluminal surface, the luminal surface, and the sidewall surfaces of the struts of the stent. In some embodiments, the coating contacts at least 99% of the abluminal, luminal, and sidewall surfaces of the struts of the stent.

In some embodiments, contact of the coating to the stent surfaces is measured by scanning electron microscopy of at least one cross section of a strut of the stent.

In some embodiments, contact of the coating is measured by when the stent is in a collapsed condition. In some embodiments, contact of the coating is measured by when the stent is in an expanded condition.

In some embodiments, the polymer comprises at least one of: a bioabsorbable polymer and a durable polymer. In some embodiments, at least a part of the polymer is bioabsorbable, as further described herein. In some embodiments, the active agent comprises at least one of a pharmaceutical agent and a biological agent as further described herein. In some embodiments, the active agent comprises rapamycin. In some embodiments, the pharmaceutical agent comprises rapamycin. In some embodiments, the active agent comprises a macrolide immunosuppressive (limus) drug. In some embodiments, at least a part of the polymer is durable.

Provided herein is a coated stent, comprising a stent comprising a plurality of stent struts each having an abluminal surface, a luminal surface, and two sidewall surfaces; a coating comprising an active agent and a bioabsorbable polymer; wherein an abluminal coating thickness on the abluminal surface and a luminal coating thickness on the luminal surface are substantially the same. When referring to a coating thickness that is "substantially the same" as another coating thickness, there is no more than 50% difference in the coating thicknesses, in some embodiments. When referring to a coating thickness that is "substantially the same" as another coating thickness, there is no more than 30% difference in the coating thicknesses, in some embodiments. When referring to a coating thickness that is "substantially the same" as another coating thickness, there is no more than 20% difference in the coating thicknesses, in some embodiments. When referring to a coating thickness that is "substantially the same" as another coating thickness, there is no more than 10% difference in the coating thicknesses, in some embodiments.

In some embodiments, the abluminal coating thickness is at most 10% greater than the luminal coating thickness. In some embodiments, the abluminal coating thickness is at most 20% greater than the luminal coating thickness. In some embodiments, the abluminal coating thickness is at most 30% greater than the luminal coating thickness. In some embodiments, the abluminal coating thickness is at most 50% greater than the luminal coating thickness.

Provided herein is a coated stent, comprising a stent comprising a plurality of stent struts each having an abluminal surface, a luminal surface, and two sidewall surfaces; a coating comprising an active agent and a bioabsorbable polymer; wherein a ratio of an abluminal coating thickness on the abluminal surface to a luminal coating thickness on the luminal surface is at most 90:10.

In some embodiments, the ratio of abluminal coating thickness to luminal coating thickness is at most 50:50. In some embodiments, the ratio of abluminal coating thickness to luminal coating thickness is at most 65:35. In some embodiments, the ratio of abluminal coating thickness to luminal coating thickness is at most 70:30. In some embodiments, the ratio of abluminal coating thickness to luminal coating thickness is at most 75:25. In some embodiments, the ratio of abluminal coating thickness to luminal coating thickness is at most 80:20. In some embodiments, the ratio of abluminal coating thickness to luminal coating thickness is achieved during coating of the stent with the coating without a masking element. In some embodiments, the ratio of abluminal coating thickness to luminal coating thickness is achieved during coating of the stent with the coating without shielding the luminal surfaces. In some embodiments, the ratio of abluminal coating thickness to luminal coating thickness is achieved during coating of the stent with the coating wherein the stent is in a collapsed condition.

In some embodiments, the ratio of abluminal coating thickness to luminal coating thickness is achieved during coating of the stent with the coating wherein the stent is in an expanded condition.

In some embodiments, the ratio of abluminal coating thickness to luminal coating thickness is achieved during coating of the stent with the coating wherein the stent is in an intermediate condition. In some embodiments, an inner diameter of the stent in the intermediate condition is between an inner diameter of the stent in the expanded condition and an inner diameter of the stent in the collapsed condition. In some embodiments, an outer diameter of the stent in the intermediate condition is between an outer diameter of the stent in the expanded condition and an outer diameter of the stent in the collapsed condition.

In some embodiments, an average strut thickness of the stent when measured from the abluminal surface to the luminal surface is at most 140 microns. In some embodiments, an average strut thickness of the stent when measured from the abluminal surface to the luminal surface is at most 125 microns. In some embodiments, average strut thickness of the stent when measured from the abluminal surface to the luminal surface is at most 100 microns. In some embodiments, an average strut thickness of the stent when measured from the abluminal surface to the luminal surface is at most 90 microns. In some embodiments, an average strut thickness of the stent when measured from the abluminal surface to the luminal surface is at most 80 microns. In some embodiments, an average strut thickness of the stent when measured from the abluminal surface to the luminal surface is at most 75 microns. In some embodiments, an average strut thickness of the stent when measured from the abluminal surface to the luminal surface is about 65 microns. In some embodiments, an average strut thickness of the stent when measured from the abluminal surface to the luminal surface is about 63 microns. In some embodiments, an average strut thickness of the stent when measured from the abluminal surface to the luminal surface is 63 microns.

Provided herein is a method of preparing a stent as described herein comprising: providing the stent; depositing a plurality of layers on said stent to form said stent; wherein at least one of said layers comprises a drug-polymer coating wherein at least part of the drug of the drug-polymer coating is in crystalline form and the polymer of the drug-polymer coating is a bioabsorbable polymer. Provided herein is a method of preparing a stent as described herein comprising: providing the stent; depositing a plurality of layers on said stent to form said stent; wherein at least one of said layers comprises a drug-polymer coating wherein at least part of the drug of the drug-polymer coating is in crystalline form and the polymer of the drug-polymer coating is a durable polymer. As used herein "drug" may refer to any active agent as defined herein.

Provided herein is a method of preparing a stent as described herein comprising: providing the stent; depositing a coating comprising a plurality of layers on said stent; wherein at least one of said layers comprises a pharmaceutical agent, wherein at least one of said layers comprises a polymer, and wherein at least a portion of the pharmaceutical agent is in crystalline form, and wherein the polymer comprises at least one of a bioabsorbable polymer, and a durable polymer.

In some embodiments, the drug and polymer are in the same layer; in separate layers or in overlapping layers. In some embodiments, the pharmaceutical agent and the polymer are in the same layer; in separate layers or in overlapping layers.

In some embodiments, the stent is made of stainless steel. In some embodiments, the stent is formed from a metal alloy. In some embodiments, the stent is formed from a cobalt chromium alloy. In some embodiments, the stent is formed from a material comprising the following percentages by weight: 0.05-0.15 C, 1.00-2.00 Mn, 0.040 Si, 0.030 P, 0.3 S, 19.00-21.00 Cr, 9.00-11.00 Ni, 14.00-16.00 W, 3.00 Fe, and Bal. Co. In some embodiments, the stent is formed from a material comprising at most the following percentages by weight: about 0.025 maximum C, 0.15 maximum Mn, 0.15 maximum Si, 0.015 maximum P, 0.01 maximum S, 19.00-21.00 maximum Cr, 33-37 Ni, 9.0-10.5 Mo, 1.0 maximum Fe, 1.0 maximum Ti, and Bal. Co.

In some embodiments, the stent has a thickness of about 50% or less of a thickness of the coated stent. In some embodiments, the stent has a thickness of about 100 µm or less.

In some embodiments, the bioabsorbable polymer is selected from PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid).

Some embodiments comprise depositing 3 or more layers. Some embodiments comprise depositing 4 or more layers. Some embodiments comprise depositing 5 or more layers. Some embodiments comprise depositing 6 or more layers. Some embodiments comprise depositing 7 or more layers. Some embodiments comprise depositing 8 or more layers. Some embodiments comprise depositing 9 or more layers. Some embodiments comprise depositing 10, 20, 50, or 100 layers. Some embodiments comprise depositing at least one of: at least 10, at least 20, at least 50, and at least 100 layers. In some embodiments, the layers comprise alternate drug and polymer layers. In some embodiments, the drug layers are substantially free of polymer and the polymer layers are substantially free of drug.

In some embodiments, the active agent comprises a macrolide immunosuppressive (limus) drug. In some embodiments, the macrolide immunosuppressive drug comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholinolacetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), and salts, derivatives, isomers, racemates, diastereoisomers, prodrugs, hydrate, ester, or analogs thereof.

In some embodiments, the macrolide immunosuppressive drug is at least 50% crystalline.

Some embodiments comprise depositing a plurality of layers on said stent to form said coronary stent comprises depositing polymer particles on said stent by an RESS process. Some embodiments comprise depositing a plurality of layers on said stent to form said coated stent comprises depositing the polymer on said stent by an RESS process. In some embodiments, depositing a plurality of layers on said stent to form said coated stent comprises depositing polymer particles on said stent in dry powder form.

Provided herein is a method of preparing a coated stent comprising: providing a stent; depositing a plurality of layers on said stent to form said stent; wherein at least one of said layers comprises a bioabsorbable polymer; wherein depositing each layer of said plurality of layers on said stent comprises the following steps: discharging at least one pharmaceutical agent and/or at least one active biological agent in dry powder form through a first orifice; discharging the at least one polymer in dry powder form through said first orifice or through a second orifice; depositing the polymer and pharmaceutical agent and/or active biological agent particles onto said stent, wherein an electrical potential is maintained between the stent and the polymer and pharmaceutical agent and/or active biological agent particles, thereby forming said layer; and sintering said layer under conditions that do not substantially modify the morphology of said pharmaceutical agent and/or the activity of said biological agent, wherein the coating is substantially conformal to each of an abluminal, luminal, and sidewall surface of the struts of the stent.

Provided herein is a method of preparing a coated stent comprising: providing a stent; depositing a coating comprising a plurality of layers on said stent; wherein at least one of said layers comprises at least one of a bioabsorbable polymer and a durable polymer; wherein depositing the coating comprises depositing each layer by the following steps: discharging at least one pharmaceutical agent and/or at least one active biological agent in dry powder form through a first orifice; discharging the at least one polymer in dry powder form through said first orifice or through a second orifice; depositing the polymer and pharmaceutical agent and/or active biological agent particles onto said stent, wherein an electrical potential is maintained between the stent and the polymer and pharmaceutical agent and/or active biological agent particles, thereby forming said layer; and sintering said layer under conditions that do not substantially modify the morphology of said pharmaceutical agent and/or the activity of said biological agent, wherein the coating is substantially conformal to each of an abluminal, luminal, and sidewall surface of the struts of the stent.

In some embodiments, the coating adheres to at least one of: at least 70%, at least 75%, at least 80%, at least 85%, at least 90%, at least 95%, at least 99% of the abluminal, luminal, and sidewall surfaces of the struts of the stent. In some embodiments, the coating contacts at least one of: at least 70%, at least 75%, at least 80%, at least 85%, at least 90%, at least 95%, at least 99% of the abluminal, luminal, and sidewall surfaces of the struts of the stent.

Provided herein is a method of preparing a coated stent comprising: providing a stent; depositing a plurality of layers on said stent to form said stent; wherein at least one of said layers comprises a bioabsorbable polymer; wherein depositing each layer of said plurality of layers on said stent comprises the following steps: discharging at least one pharmaceutical agent and/or at least one active biological agent in dry powder form through a first orifice; discharging the at least one polymer in dry powder form through said first orifice or through a second orifice; depositing the polymer and pharmaceutical agent and/or active biological agent particles onto said stent, wherein an electrical potential is maintained between the stent and the polymer and pharmaceutical agent and/or active biological agent particles, thereby forming said layer; and sintering said layer under conditions that do not substantially modify the morphology of said pharmaceutical agent and/or the activity of said biological agent, wherein an abluminal coating thickness on the abluminal surface and a luminal coating thickness on the luminal surface are substantially the same.

Provided herein is a method of preparing a coated stent comprising: providing a stent; depositing a coating comprising a plurality of layers on said stent; wherein at least one of said layers comprises at least one of a bioabsorbable polymer and a durable polymer; wherein depositing the coating comprises depositing each layer by the following steps: discharging at least one pharmaceutical agent and/or at least one active biological agent in dry powder form through a first orifice; discharging the at least one polymer in dry powder form through said first orifice or through a second orifice; depositing the polymer and pharmaceutical agent and/or active biological agent particles onto said stent, wherein an electrical potential is maintained between the stent and the polymer and pharmaceutical agent and/or active biological agent particles, thereby forming said layer; and sintering said layer under conditions that do not substantially modify the morphology of said pharmaceutical agent and/or the activity of said biological agent, wherein an abluminal coating thickness on the abluminal surface and a luminal coating thickness on the luminal surface are substantially the same.

In some embodiments, the abluminal coating thickness is at least one of: at most 10% greater than the luminal coating thickness, at most 20% greater than the luminal coating thickness, at most 30% greater than the luminal coating thickness, at most 50% greater than the luminal coating thickness. In some embodiments, an average strut thickness of the stent when measured from the abluminal surface to the luminal surface is at least one of: at most 140 microns, at most 125 microns, at most 100 microns, at most 90 microns, at most 80 microns, at most 75 microns, at most 65 microns, and at most 63 microns.

Provided herein is a method of preparing a coated stent comprising: providing a stent; depositing a plurality of layers on said stent to form said stent; wherein at least one of said layers comprises a bioabsorbable polymer; wherein depositing each layer of said plurality of layers on said stent comprises the following steps: discharging at least one pharmaceutical agent and/or at least one active biological agent in dry powder form through a first orifice; discharging the at least one polymer in dry powder form through said first orifice or through a second orifice; depositing the polymer and pharmaceutical agent and/or active biological agent particles onto said stent, wherein an electrical potential is maintained between the stent and the polymer and pharmaceutical agent and/or active biological agent particles, thereby forming said layer; and sintering said layer under conditions that do not substantially modify the morphology of said pharmaceutical agent and/or the activity of said biological agent, wherein a ratio of an abluminal coating thickness on the abluminal surface to a luminal coating thickness on the luminal surface is at most 90:10.

Provided herein is a method of preparing a coated stent comprising: providing a stent; depositing a coating comprising a plurality of layers on said stent; wherein at least one of said layers comprises at least one of a bioabsorbable polymer and a durable polymer; wherein depositing the coating comprises depositing each layer by the following steps: discharging at least one pharmaceutical agent and/or at least one active biological agent in dry powder form through a first orifice; discharging the at least one polymer in dry powder form through said first orifice or through a second orifice; depositing the polymer and pharmaceutical agent and/or active biological agent particles onto said stent, wherein an electrical potential is maintained between the stent and the polymer and pharmaceutical agent and/or active biological agent particles, thereby forming said layer; and sintering said layer under conditions that do not substantially modify the morphology of said pharmaceutical agent and/or the activity of said biological agent, wherein a ratio of an abluminal coating thickness on the abluminal surface to a luminal coating thickness on the luminal surface is at most 90:10.

In some embodiments, the ratio of abluminal coating thickness to luminal coating thickness is at least one of: at most 50:50, at most 65:35, at most 70:30, and at most 80:20. In some embodiments, the ratio of abluminal coating thickness to luminal coating thickness is achieved during coating of the stent with the coating wherein the stent is in at least one of: a collapsed condition, an expanded condition, and an intermediate condition. In some embodiments, an average strut thickness of the stent when measured from the abluminal surface to the luminal surface is at least one of: at most 140 microns, at most 125 microns, at most 100 microns, at most 90 microns, at most 80 microns, at most 75 microns, at most 65 microns, and at most 63 microns.

Some embodiments further comprise discharging a third dry powder comprising a second pharmaceutical agent in a therapeutically desirable morphology in dry powder form and/or active biological agent whereby a layer comprising at least two different pharmaceutical agents and/or active biological agents is deposited on said stent or at least two layers each comprising one of two different pharmaceutical agents and/or active biological agents are deposited on said stent.

In some embodiments, the stent is electrostatically charged.

In some embodiments, the stent is biodegradable.

In some embodiments, the therapeutically desirable morphology of said pharmaceutical agent is crystalline or semicrystalline.

In some embodiments, at least 50% of said pharmaceutical agent in powder form is crystalline or semicrystalline.

In some embodiments, the pharmaceutical agent comprises at least one drug.

In some embodiments, the at least one drug is selected from the group consisting of antirestenotic agents, antidiabetics, analgesics, anti-inflammatory agents, antirheumatics, antihypotensive agents, antihypertensive agents.

In some embodiments, the activity of said active biological agent is of therapeutic or prophylactic value.

In some embodiments, the biological agent is selected from the group comprising peptides, proteins, enzymes, nucleic acids, antisense nucleic acids, antimicrobials, vitamins, hormones, steroids, lipids, polysaccharides and carbohydrates.

In some embodiments, the activity of said active biological agent is influenced by the secondary, tertiary or quaternary structure of said active biological agent.

In some embodiments, the active biological agent possesses a secondary, tertiary or quaternary structure which is not substantially changed after the step of sintering said layer.

In some embodiments, the active biological agent further comprises a stabilizing agent.

In some embodiments, the sintering comprises treating said layer with a compressed gas, compressed liquid or supercritical fluid that is a non-solvent for both the polymer and the pharmaceutical and/or biological agents.

In some embodiments, the compressed gas, compressed liquid or supercritical fluid comprises carbon dioxide, isobutylene or a mixture thereof.

In some embodiments, at least one layer comprises a microstructure. In some embodiments, the microstructure comprises microchannels, micropores and/or microcavities. In some embodiments, the particles of said pharmaceutical agent and/or active biological agent are sequestered or encapsulated within said microstructure. In some embodiments, the microstructure is selected to allow controlled release of said pharmaceutical agent and/or active biological agent. In some embodiments, the microstructure is selected to allow sustained release of said pharmaceutical agent and/or active biological agent. In some embodiments, the microstructure is selected to allow continuous release of said pharmaceutical agent and/or active biological agent. In some embodiments, the microstructure is selected to allow pulsatile release of said pharmaceutical agent and/or active biological agent.

In some embodiments, the bioabsorbable polymer is selected from PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid).

Some embodiments of the methods comprise depositing 3 or more layers. Some embodiments comprise depositing 4 or more layers. Some embodiments comprise depositing 5 or more layers. Some embodiments comprise depositing 6 or more layers. Some embodiments comprise depositing 7 or more layers. Some embodiments comprise depositing 8 or more layers. Some embodiments comprise depositing 9 or more layers.

Some embodiments of the methods comprise depositing 10, 20, 50, or 100 layers. Some embodiments of the methods comprise depositing at least one of: at least 10, at least 20, at least 50, and at least 100 layers.

In some embodiments, the layers comprise alternate drug and polymer layers. In some embodiments, the drug layers are substantially free of polymer and the polymer layers are substantially free of drug. In some embodiments, the one or more active agents comprise a macrolide immunosuppressive (limus) drug. In some embodiments, the layers comprise alternate pharmaceutical agent and/or active biological agent layers and polymer layers. In some embodiments, the pharmaceutical agent and/or active biological agent layers are substantially free of polymer and the polymer layers are substantially free of pharmaceutical agent and/or active biological agent. In some embodiments, the said pharmaceutical agent comprise a macrolide immunosuppressive (limus) drug.

In some embodiments, the macrolide immunosuppressive drug comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 40-O-[2-(N-Morpholinolacetoxy]ethyl-rapamycin 4O—O-(2-N-Imidazolylacetoxy)ethyl-rapamycin, 4O—O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), and salts, derivatives, isomers, racemates, diastereoisomers, prodrugs, hydrate, ester, or analogs thereof.

Provided herein is a coated coronary stent, comprising: a stent; a first layer of bioabsorbable polymer; and a coating comprising rapamycin and a second bioabsorbable polymer wherein at least part of rapamycin is in crystalline form and wherein the first polymer is a slow absorbing polymer and the second polymer is a fast absorbing polymer, and wherein the coating is substantially conformal to each of an abluminal, luminal, and sidewall surface of the struts of the stent.

Provided herein is a coated coronary stent, comprising: a stent; a first layer of bioabsorbable polymer; and a coating comprising rapamycin and a second bioabsorbable polymer wherein at least part of rapamycin is in crystalline form and wherein the first polymer is a slow absorbing polymer and the second polymer is a fast absorbing polymer, and wherein an abluminal coating thickness on the abluminal surface and a luminal coating thickness on the luminal surface are substantially the same.

Provided herein is a coated coronary stent, comprising: a stent; a first layer of bioabsorbable polymer; and a coating comprising rapamycin and a second bioabsorbable polymer wherein at least part of rapamycin is in crystalline form and wherein the first polymer is a slow absorbing polymer and the second polymer is a fast absorbing polymer, and wherein a ratio of an abluminal coating thickness on the abluminal surface to a luminal coating thickness on the luminal surface is at most 90:10

In some embodiments, the fast absorbing polymer is PLGA copolymer with a ratio of about 40:60 l-lactide: glycolide to about 60:40 l-lactide: glycolide and the slow absorbing polymer is a PLGA copolymer with a ration of about 70:30 l-lactide: glycolide to about 90:10 l-lactide: glycolide. The term "about" when used with respect to ratio of l-lactide: glycolide in PLGA can mean variations of any of: up to 5%, up to 10%, and up to 20%.

The stents provided herein may be thinner than other coated stents because the stent itself may be thinner since the coating can provide rigidity and radial strength to the coated stent. Also, or alternatively, the coating itself can be thinner than other coated stents because of the processes described herein which can lay very thin layers on the stent.

EXAMPLES

The following examples are provided to illustrate selected embodiments. They should not be considered as limiting the scope of the invention, but merely as being illustrative and representative thereof. For each example listed herein, multiple analytical techniques may be provided. Any single technique of the multiple techniques listed may be sufficient to show the parameter and/or characteristic being tested, or any combination of techniques may be used to show such parameter and/or characteristic. Those skilled in the art will be familiar with a wide range of analytical techniques for the characterization of drug/polymer coatings. Techniques presented here, but not limited to, may be used to additionally and/or alternatively characterize specific properties of the coatings with variations and adjustments employed which would be obvious to those skilled in the art.

Sample Preparation

Generally speaking, coatings on stents, on balloons, on coupons, on other substrates, or on samples prepared for in-vivo models are prepared as herein. Nevertheless, modifications for a given analytical method are presented within the examples shown, and/or would be obvious to one having skill in the art. Thus, numerous variations, changes, and substitutions will now occur to those skilled in the art without departing from the invention. It should be understood that various alternatives to the embodiments of the invention described herein and examples provided may be employed in practicing the invention and showing the parameters and/or characteristics described.

Coatings on Stents

Coated stents as described herein and/or made by a method disclosed herein are prepared. In some examples, the coated stents have a targeted thickness of ~15 microns (5 microns of active agent). In some examples, the coating process is PDPDP (Polymer, sinter, Drug, Polymer, sinter, Drug, Polymer, sinter) using deposition of drug in dry powder form and deposition of polymer particles by RESS methods and equipment described herein. In the illustrations herein, resulting coated stents may have a 3-layer coating comprising polymer (for example, PLGA) in the first layer, drug (for example, rapamycin) in a second layer and polymer in the third layer, where a portion of the third layer is substantially drug free (e.g. a sub-layer within the third layer having a thickness equal to a fraction of the thickness of the third layer). As described, the middle layer (or drug layer) may be overlapping with one or both first (polymer) and third (polymer) layer. The overlap between the drug layer and the polymer layers is defined by extension of polymer material into physical space largely occupied by the drug. The overlap between the drug and polymer layers may relate to partial packing of the drug particles during the formation of the drug layer. When crystal drug particles are deposited on top of the first polymer layer, voids and or gaps may remain between dry crystal particles. The voids and gaps are available to be occupied by particles deposited during the formation of the third (polymer) layer. Some of the particles from the third (polymer) layer may rest in the vicinity of drug particles in the second (drug) layer. When the sintering step is completed for the third (polymer) layer, the third polymer layer particles fuse to form a continuous film that forms the third (polymer) layer. In some embodiments, the third (polymer) layer however will have a portion along the longitudinal axis of the stent whereby the portion is free of contacts between polymer material and drug particles. The portion of the third layer that is substantially of contact with drug particles can be as thin as 1 nanometer.

Polymer-coated stents having coatings comprising polymer but no drug are made by a method disclosed herein and are prepared having a targeted thickness of, for example, ~5 microns. An example coating process is PPP (PLGA, sinter, PLGA, sinter, PLGA, sinter) using RESS methods and equipment described herein. These polymer-coated stents may be used as control samples in some of the examples, infra.

In some examples, the stents are made of a cobalt-chromium alloy and are 5 to 50 mm in length, preferably 10-20 mm in length, with struts of thickness between 20 and 100 microns, preferably 50-70 microns, measuring from an abluminal surface to a luminal surface, or measuring from a side wall to a side wall. In some examples, the stent may be cut lengthwise and opened to lay flat be visualized and/or assayed using the particular analytical technique provided.

The coating may be removed (for example, for analysis of a coating band and/or coating on a strut, and/or coating on the abluminal surface of a flattened stent) by scraping the coating off using a scalpel, knife or other sharp tool. This coating may be sliced into sections which may be turned 90 degrees and visualized using the surface composition techniques presented herein or other techniques known in the art for surface composition analysis (or other characteristics, such as crystallinity, for example). In this way, what was an analysis of coating composition through a depth when the coating was on the stent or as removed from the stent (i.e. a depth from the abluminal surface of the coating to the surface of the removed coating that once contacted the strut or a portion thereof), becomes a surface analysis of the coating which can, for example, show the layers in the slice of coating, at much higher resolution. Coating removed from the stent may be treated the same way, and assayed, visualized, and/or characterized as presented herein using the techniques described and/or other techniques known to a person of skill in the art.

Coatings on Coupons

In some examples, samples comprise coupons of glass, metal, e.g. cobalt-chromium, or another substance that are prepared with coatings as described herein, with a plurality of layers as described herein, and/or made by a method disclosed herein. In some examples, the coatings comprise polymer. In some examples, the coatings comprise polymer and active agent. In some examples, the coated coupons are prepared having a targeted thickness of ~10 microns (with ~5 microns of active agent), and have coating layers as described for the coated stent samples, infra.

Sample Preparation for In-Vivo Models

Devices comprising balloons having coatings disclosed herein are deployed in the porcine coronary arteries of pigs (domestic swine, juvenile farm pigs, or Yucatan miniature swine). Porcine coronary angioplasty is exploited herein since such model yields results that are comparable to other investigations assaying neointimal hyperplasia in human subjects. The balloons are expanded to a 1:1.1 balloon:artery ratio. At multiple time points, animals are euthanized (e.g. t=1 day, 7 days, 14 days, 21 days, and 28 days), the tissue surrounding the intervention site is extracted, and assayed.

Devices comprising balloons having coatings disclosed herein alternatively are implanted in the common iliac arteries of New Zealand white rabbits. The balloons are expanded to a 1:1.1 balloon:artery ratio. At multiple time points, animals are euthanized (e.g., t=1 day, 7 days, 14 days, 21 days, and 28 days), the tissue surrounding the intervention site is extracted, and assayed.

Example 1

In this example illustrates embodiments that provide a coated coronary stent, comprising: a stent and a rapamycin-polymer coating wherein at least part of rapamycin is in crystalline form and the rapamycin-polymer coating comprises one or more resorbable polymers.

In these experiments two different polymers were employed:

Metal stents were coated as follows:
AS1: Polymer A/Rapamycin/Polymer A/Rapamycin/Polymer A
AS2: Polymer A/Rapamycin/Polymer A/Rapamycin/Polymer B
AS1 (B): Polymer B/Rapamycin/Polymer B/Rapamycin/Polymer B
AS1b: Polymer A/Rapamycin/Polymer A/Rapamycin/Polymer A
AS2b: Polymer A/Rapamycin/Polymer A/Rapamycin/Polymer B The coated stents stent prepared as described are loaded onto a balloon catheter. A segment of optically clear TYGON® B-44-3 Beverage Tubing with O.D.=0.125", I.D.=0.0625" (available from McMaster-Carr, Part Number: 5114K11 (www.mcmaster.com) is filled with phosphate-buffered saline solution and immersed in a water bath at 37° C. to mimic physiological conditions of deployment into a coronary artery. The coated stents are inserted into the tubing and the catheter-balloon is inflated to 13 ATM for less than 20 seconds to deploy the stent against the tubing wall. Optical microscopy of the stents and of the tubing is performed immediately after retraction of the stent delivery system to show that some of the coating was released from the strut. Calculations of the amount of coating left on the stent and/or freed from the stent, by means of area measurements, can determine the amount of coating that was freed from, transferred from, and or dissociated from the stent, and the amount of coating that was deposited at, and/or delivered to the tubing (i.e., the intervention site).

In an alternative embodiment, the stent framework is not comprised of a memory metal, rather is plastically deformable and connected to the balloon, such that the stent shape (e.g. diameter) is defined by and/or controlled by the shape (e.g., diameter) of the balloon, and the stent expands and collapses with the balloon.

Example 2: Crystallinity of Drug on a Device

The presence and or quantification of the Active agent crystallinity can be determined from a number of characterization methods known in the art, but not limited to, XRPD, vibrational spectroscopy (FTIR, NIR, Raman), polarized optical microscopy, calorimetry, thermal analysis and solid-state NMR.

X-Ray Diffraction to Determine the Presence and/or Quantification of Active Agent Crystallinity Active agent and polymer coated proxy substrates are prepared using 316L stainless steel coupons for X-ray powder diffraction (XRPD) measurements to determine the presence of crystallinity of the active agent. The coating on the coupons is equivalent to the coating on the stents described herein. Coupons of other materials described herein, such as cobalt-chromium alloys, may be similarly prepared and tested. Likewise, substrates such as stents, or other medical devices described herein may be prepared and tested. Where a coated stent is tested, the stent may be cut lengthwise and opened to lay flat in a sample holder.

For example XRPD analyses are performed using an X-ray powder diffractometer (for example, a Bruker D8 Advance X-ray diffractometer) using Cu Kα radiation. Diffractograms are typically collected between 2 and 40 degrees 2 theta. Where required low background XRPD sample holders are employed to minimize background noise.

The diffractograms of the deposited active agent are compared with diffractograms of known crystallized active agents, for example micronized crystalline sirolimus in powder form. XRPD patterns of crystalline forms show strong diffraction peaks whereas amorphous show diffuse and non-distinct patterns. Crystallinity is shown in arbitrary Intensity units.

A related analytical technique which may also be used to provide crystallinity detection is wide angle scattering of radiation (e.g.; Wide Angle X-ray Scattering or WAXS), for example, as described in F. Unger, et al., "Poly(ethylene carbonate): A thermoelastic and biodegradable biomaterial for drug eluting stent coatings?" Journal of Controlled Release, Volume 117, Issue 3, 312-321 (2007) for which the technique and variations of the technique specific to a particular sample would be obvious to one of skill in the art.

Raman Spectroscopy

Raman spectroscopy, a vibrational spectroscopy technique, can be useful, for example, in chemical identification, characterization of molecular structures, effects of bonding, identification of solid state form, environment and stress on a sample. Raman spectra can be collected from a very small volume (<1 µm3); these spectra allow the identification of species present in that volume. Spatially resolved chemical information, by mapping or imaging, terms often used interchangeably, can be achieved by Raman microscopy.

Raman spectroscopy and other analytical techniques such as described in Balss, et al., "Quantitative spatial distribution of sirolimus and polymers in drug-eluting stents using confocal Raman microscopy" J. of Biomedical Materials Research Part A, 258-270 (2007), incorporated in its entirety herein by reference, and/or described in Belu et al., "Three-Dimensional Compositional Analysis of Drug Eluting Stent Coatings Using Cluster Secondary Ion Mass Spectroscopy" Anal. Chem. 80: 624-632 (2008) incorporated herein in its entirety by reference may be used.

For example, to test a sample using Raman microscopy and in particular confocal Raman microscopy, it is understood that to get appropriate Raman high resolution spectra sufficient acquisition time, laser power, laser wavelength, sample step size and microscope objective need to be optimized. For example a sample (a coated stent) is prepared as described herein. Alternatively, a coated coupon could be tested in this method. Maps are taken on the coating using Raman microscopy. A WITec CRM 200 scanning confocal Raman microscope using a Nd:YAG laser at 532 nm is applied in the Raman imaging mode. The laser light is focused upon the sample using a 100× dry objective (numerical aperture 0.90), and the finely focused laser spot is scanned into the sample. As the laser scans the sample, over each 0.33 micron interval a Raman spectrum with high signal to noise is collected using 0.3 seconds of integration time. Each confocal cross-sectional image of the coatings displays a region 70 µm wide by 10 µm deep, and results from the gathering of 6300 spectra with a total imaging time of 32 min.

Multivariate analysis using reference spectra from samples of rapamycin (amorphous and crystalline) and polymer are used to deconvolve the spectral data sets, to provide chemical maps of the distribution.

Infrared (IR) Spectroscopy for In-Vitro Testing

Infrared (IR) Spectroscopy such as FTIR and ATR-IR are well utilized techniques that can be applied to show, for example, the quantitative drug content, the distribution of the drug in the sample coating, the quantitative polymer content in the coating, and the distribution of polymer in the coating. Infrared (IR) Spectroscopy such as FTIR and ATR-IR can similarly be used to show, for example, drug crystallinity. The following table (Table 2) lists the typical IR materials for various applications. These IR materials are used for IR windows, diluents or ATR crystals.

TABLE 2

| | MATERIAL | | | | | | |
|---|---|---|---|---|---|---|---|
| | NACL | KBR | SCI | AGCL | GE | ZNSE | DIAMOND |
| Transmission range (cm-1) | 40,000 ~625 | 40,000 ~400 | 40,000 ~200 | 25,000 ~360 | 5,500 ~625 | 20,200 ~425 | 40,000 ~2,500 & 1667-33 |
| Water Sol (g/100 g, 25 C.) | 35.7 | 53.5 | 44.4 | Insol. | Insol. | Insol. | Insol. |
| Attacking materials | Wet Solvent | Wet Solvent | Wet Solvent | Ammonuim Salts | H2S04, aqua resin | Acids, strong aklalies, chlorinated solvents | K2Cr2Os, conc. H2S04 |

In one test, a coupon of crystalline ZnSe is coated by the processes described herein, creating a PDPDP (Polymer, Drug, Polymer, Drug, Polymer) layered coating that is about 10 microns thick. The coated coupon is analyzed using FTIR. The resulting spectrum shows crystalline drug as determined by comparison to the spectrum obtained for the crystalline form of a drug standard (i.e. a reference spectrum).

Differential Scanning Calorimetry (DSC)

DSC can provide qualitative evidence of the crystallinity of the drug (e.g. rapamycin) using standard DSC techniques obvious to one of skilled in the art. Crystalline melt can be shown using this analytical method (e.g. rapamycin crystalline melting—at about 185 degrees C. to 200 degrees C., and having a heat of fusion at or about 46.8 J/g). The heat of fusion decreases with the percent crystallinity. Thus, the degree of crystallinity could be determined relative to a pure sample, or versus a calibration curve created from a sample of amorphous drug spiked and tested by DSC with known amounts of crystalline drug. Presence (at least) of crystalline drug on a stent could be measured by removing (scraping or stripping) some drug from the stent and testing the coating using the DSC equipment for determining the melting temperature and the heat of fusion of the sample as compared to a known standard and/or standard curve.

Confocal Raman Microscopy

Confocal Raman Microscopy can provide nondestructive depth analysis and allows coating specific Raman spectral features to be obtained (Bugay et al., "Raman Analysis of Pharmaceuticals," in "Applications *of Vibrational Spectroscopy in Pharmaceutical Research and Development,"* Ed. Pivonka, D. E., Chalmers, J. M., Griffiths, P. R. (2007) Wiley and Sons). In confocal Raman microscopy an aperture is place in a focal place of the collected beam. This limitation defines a shallow portion of the depth of field and thereby provides definition of the z-axis spatial resolution for data collection. By adjusting the aperture and moving the focus within the sample, the sampling position within the sample moves. Moving the sample focus from the top surface, deeper into the specimen facilitates nondestructive depth analysis.

Example 3: Determination of Bioabsorbability/Bioresorbability/Dissolution Rate of a Polymer Coating a Device Gel Permeation Chromatography In-Vivo Weight Loss Determination Standard methods known in the art can be applied to determine polymer weight loss, for example gel permeation chromatography and other analytical techniques such as described in Jackson et al., "Characterization of perivascular poly(lactic-co-glycolic acid) films containing paclitaxel" *Int. J. of Pharmaceutics,* 283:97-109 (2004), incorporated in its entirety herein by reference.

For example rabbit in vivo models as described above are euthanized at multiple time points (t=1 day, 2 days, 4 days, 7 days, 14 days, 21 days, 28 days, 35 days n=5 per time point). Alternatively, pig in vivo models as described above are euthanized at multiple time points (t=1 day, 2 days, 4 days, 7 days, 14 days, 21 days, 28 days, 35 days n=5 per time point). The stents are explanted, and dried down at 30° C. under a stream of gas to complete dryness. A stent that has not been implanted in the animal is used as a control for no loss of polymer.

The remaining polymer on the explanted stent is removed using a solubilizing solvent (for example chloroform). The solutions containing the released polymers for each time point are filtered. Subsequent GPC analysis is used for quantification of the amount of polymer remaining in the stent at each explant time point. The system, for example, comprises a Shimadzu LC-10 AD HPLC pump, a Shimadzu RID-6A refractive index detector coupled to a 50 Å Hewlett Packard Pl-Gel column. The polymer components are detected by refractive index detection and the peak areas are used to determine the amount of polymer remaining in the stents at the explant time point. A calibration graph of log molecular weight versus retention time is established for the 50A Pl-Gel column using polystyrene standards with molecular weights of 300, 600, 1.4 k, 9 k, 20 k, and 30 k g/mol. The decreases in the polymer peak areas on the subsequent time points of the study are expressed as weight percentages relative to the 0 day stent Gel Permeation Chromatography In-Vitro Testing Gel Permeation Chromatography (GPC) can also be used to quantify the bioabsorbability/bioresorbability, dissolution rate, and/or biodegradability of the polymer coating. The in vitro assay is a degradation test where the concentration and molecular weights of the polymers can be assessed when released from the stents in an aqueous solution that mimics physiological surroundings. See for example, Jackson et al., "Characterization of perivascular poly(lactic-co-glycolic acid) films containing paclitaxel" *Int. J. of Pharmaceutics,* 283:97-109 (2004), incorporated in its entirety herein by reference.

For example Stents (n=15) described herein are expanded and then placed in a solution of 1.5 ml solution of phosphate buffered saline (pH=7.4) with 0.05% wt of Tween20, or in the alternative 10 mM Tris, 0.4 wt. % SDS, pH 7.4, in a 37° C. bath with bath rotation at 70 rpm. Alternatively, a coated coupon could be tested in this method. The solution is then collected at the following time points: 0 min., 15 min., 30 min., 1 hr, 2 hr, 4 hr, 6 hr, 8 hr, 12 hr, 16 hr, 20 hr, 24 hr, 30 hr, 36 hr, 48 hr, and daily up to 70 days, for example. The solution is replaced at least at each time point, and/or periodically (e.g. every four hours, daily, weekly, or longer for later time points) to prevent saturation, the removed solution is collected, saved, and assayed. The solutions containing the released polymers for each time point are filtered to reduce clogging the GPC system. For time points over 4 hours, the multiple collected solutions are pooled together for liquid extraction.

1 ml Chloroform is added to the phosphate buffered saline solutions and shaken to extract the released polymers from the aqueous phase. The chloroform phase is then collected for assay via GPC.

The system comprises a Shimadzu LC-10 AD HPLC pump, a Shimadzu RID-6A refractive index (RI) detector coupled to a 50 Å Hewlett Packard Pl-Gel column The mobile phase is chloroform with a flow rate of 1 mL/min. The injection volume of the polymer sample is 100 μL of a polymer concentration. The samples are run for 20 minutes at an ambient temperature.

For determination of the released polymer concentrations at each time point, quantitative calibration graphs are first made using solutions containing known concentrations of each polymer in chloroform. Stock solutions containing each polymer in 0-5 mg/ml concentration range are first analyzed by GPC and peak areas are used to create separate calibration curves for each polymer.

For polymer degradation studies, a calibration graph of log molecular weight versus retention time is established for a 50 Å Pl-Gel column (Hewlett Packard) using polystyrene standards with molecular weights of 300, 600, 1.4 k, 9 k, 20 k, and 30 k g/mol. In the alternative, a Multi Angle Light Scattering (MALS) detector may be fitted to directly assess the molecular weight of the polymers without the need of polystyrene standards.

To perform an accelerated in-vitro dissolution of the bioresorbable polymers, a protocol is adapted from ISO Standard 13781 "Poly(L-lactide) Resins and Fabricated Forms for Surgical Implants in vitro degradation testing" (1997), incorporated in its entirety herein by reference. Briefly, elution buffer comprising 18% v/v of a stock solution of 0.067 mol/L $KH_2PO_4$ and 82% v/v of a stock solution of 0.067 mol/L $Na_2HPO_4$ with a pH of 7.4 is used. Stents described herein are expanded and then placed in 1.5 ml solution of this accelerated elution in a 70° C. bath with rotation at 70 rpm. The solutions are then collected at the following time points: 0 min., 15 min., 30 min., 1 hr, 2 hr, 4 hr, 6 hr, 8 hr, 12 hr, 16 hr, 20 hr, 24 hr, 30 hr, 36 hr and 48 hr. Fresh accelerated elution buffer are added periodically every two hours to replace the incubated buffers that are collected and saved in order to prevent saturation. The solutions containing the released polymers for each time point are filtered to reduce clogging the GPC system. For time points over 2 hours, the multiple collected solutions are pooled together for liquid extraction by chloroform. Chloroform extraction and GPC analysis is performed in the manner described above Scanning Electron Microscopy (SEM) with Focused Ion Beam (FIB) Milling In-Vitro Testing Focused ion beam FIB is a tool that allows precise site-specific sectioning, milling and depositing of materials. FIB can be used in conjunction with SEM, at ambient or cryo conditions, to produce in-situ sectioning followed by high-resolution imaging. FIB-SEM can produce a cross-sectional image of the polymer layers on the stent. The image can be used to quantitate the thickness of the layers to reveal rate of bioresorbability of single or multiple polymers as well as show whether there is uniformity of the layer thickness at manufacture and at time points after stenting (or after in-vitro elution at various time points).

For example, testing is performed at multiple time points. Stents are removed from the elution media and dried, the dried stent is visualized using FIB-SEM for changes in the coating. Alternatively, a coated coupon could be tested in this method.

Stents (n=15) described herein are expanded and then placed in 1.5 ml solution of phosphate buffered saline (pH=7.4) with 0.05% wt of Tween20 in a 37° C. bath with bath rotation at 70 rpm. Alternatively, a coated coupon could be tested in this method. The phosphate buffered saline solution is periodically replaced with fresh solution at each time point and/or every four hours to prevent saturation. The stents are collected at the following time points: 30 min, 1 hr, 2 hr, 4 hr, 6 hr, 8, hr, 12 hr, 16 hr, 20 hr, 24 hr, 30 hr, 36 hr, 48 hr, 60 h and 72 h. The stents are dried down at 30° C. under a stream of gas to complete dryness. A stent that not been subjected to these conditions is used as a t=0 control.

A FEI Dual Beam Strata 235 FIB/SEM system is a combination of a finely focused Ga ion beam (FIB) accelerated by 30 kV with a field emission electron beam in a scanning electron microscope instrument and is used for imaging and sectioning the stents. Both beams focus at the same point of the sample with a probe diameter less than 10 nm. The FIB can also produce thinned down sections for TEM analysis.

To prevent damaging the surface of the stent with incident ions, a Pt coating is first deposited via electron beam assisted deposition and ion beam deposition prior to FIB sectioning. For FIB sectioning, the Ga ion beam is accelerated to 30 kV and the sectioning process is about 2 h in duration. Completion of the FIB sectioning allows one to observe and quantify by SEM the thickness of the polymer layers that are left on the stent as they are absorbed.

Raman Spectroscopy In-Vitro Testing

As discussed in example 2, Raman spectroscopy can be applied to characterize the chemical structure and relative concentrations of drug and polymer coatings. This can also be applied to characterize in-vitro tested polymer coatings on stents or other substrates.

For example, confocal Raman Spectroscopy/microscopy can be used to characterize the relative drug to polymer ratio at the outer ~1 μm of the coated surface as a function of time exposed to elution media. In addition confocal Raman x-z or z (maps or line scans) microscopy can be applied to characterize the relative drug to polymer ratio as a function of depth at time t after exposure to elution media.

For example a sample (a coated stent) is prepared as described herein and placed in elution media (e.g., 10 mM tris(hydroxymethyl)aminomethane (Tris), 0.4 wt. % Sodium dodecyl sulphate (SDS), pH 7.4 or 1.5 ml solution of phosphate buffered saline (pH=7.4) with 0.05% wt of Tween20) in a 37° C. bath with bath rotation at 70 rpm. Confocal Raman Images are taken on the coating before elution. At at least four elution time points within a 48 day interval, (e.g. 0 min., 15 min., 30 min., 1 hr, 2 hr, 4 hr, 6 hr, 8, hr, 12 hr, 16 hr, 20 hr, 24 hr, 30 hr, 36 hr and 48 hr) the sample is removed from the elution, and dried (for example, in a stream of nitrogen). The dried stent is visualized using Raman Spectroscopy for changes in coating. Alternatively, a coated coupon could be tested in this method. After analysis, each is returned to the buffer for further elution.

Raman spectroscopy and other analytical techniques such as described in Balss, et al., "Quantitative spatial distribution of sirolimus and polymers in drug-eluting stents using confocal Raman microscopy" *J. of Biomedical Materials Research Part A,* 258-270 (2007), incorporated in its entirety herein by reference, and/or described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

For example a WITec CRM 200 scanning confocal Raman microscope using a Nd:YAG laser at 532 nm is applied in the Raman imaging mode to generate an x-z map. The sample is placed upon a piezoelectrically driven table, the laser light is focused upon the sample using a 100× dry objective (numerical aperture 0.90), and the finely focused laser spot is scanned into the sample. As the laser scans the sample, over each 0.33 micron interval a Raman spectrum with high signal to noise is collected using 0.3 Seconds of integration time. Each confocal crosssectional image of the coatings displays a region 70 μm wide by 10 μm deep, and results from the gathering of 6300 spectra with a total imaging time of 32 mM.

SEM—In-Vitro Testing

Testing is performed at multiple time points (e.g. 0 min., 15 min., 30 min., 1 hr, 2 hr, 4 hr, 6 hr, 8, hr, 12 hr, 16 hr, 20 hr, 24 hr, 30 hr, 36 hr and 48 hr). Stents are removed from the elution media (described supra) and dried at these time points. The dried stent is visualized using SEM for changes in coating.

For example the samples are observed by SEM using a Hitachi S-4800 with an accelerating voltage of 800V. Various magnifications are used to evaluate the coating integrity, especially at high strain regions. Change in coating over time is evaluated to visualize the bioabsorption of the polymer over time.

X-Ray Photoelectron Spectroscopy (XPS)—In-Vitro Testing

XPS can be used to quantitatively determine elemental species and chemical bonding environments at the outer 5-10 nm of sample surface. The technique can be operated in spectroscopy or imaging mode. When combined with a sputtering source, XPS can be utilized to give depth profiling chemical characterization.

XPS testing can be used to characterize the drug to polymer ratio at the very surface of the coating of a sample. Additionally XPS testing can be run in time lapse to detect changes in composition. Thus, in one test, samples are tested using XPS at multiple time points (e.g. 0 min., 15 min., 30 min., 1 hr, 2 hr, 4 hr, 6 hr, 8, hr, 12 hr, 16 hr, 20 hr, 24 hr, 30 hr, 36 hr and 48 hr). Stents are removed from the elution media (e.g., 10 mM Tris, 0.4 wt. % SDS, pH 7.4 or 1.5 ml solution of phosphate buffered saline (pH=7.4) with 0.05% wt of Tween20) in a 37° C. bath with rotation at 70 rpm and dried at these time points.

XPS (ESCA) and other analytical techniques such as described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

For example, XPS analysis is performed using a Physical Electronics Quantum 2000 Scanning ESCA. The monochromatic Al Kα source is operated at 15 kV with a power of 4.5 W. The analysis is performed at a 45° take off angle. Three measurements are taken along the length of each stent with the analysis area ~20 microns in diameter. Low energy electron and $Ar^+$ ion floods are used for charge compensation Time of Flight Secondary Ion Mass Spectrometery (TOF-SIMS)

TOF-SIMS can be used to determine molecular species at the outer 1-2 nm of sample surface when operated under static conditions. The technique can be operated in spectroscopy or imaging mode at high spatial resolution. When operated under dynamic experimental conditions, known in the art, depth profiling chemical characterization can be achieved.

TOF-SIMS testing can be used to characterize the presence of polymer and or drug at uppermost surface of the coating of a sample. Additionally TOF-SIMS testing can be run in time lapse to detect changes in composition. Thus, in one test, samples are tested using TOF-SIMS at multiple time points (e.g., 0 min., 15 min., 30 min., 1 hr, 2 hr, 4 hr, 6 hr, 8, hr, 12 hr, 16 hr, 20 hr, 24 hr, 30 hr, 36 hr and 48 hr). Stents are removed from the elution media (e.g. 10 mM Tris, 0.4 wt. % SDS, pH 7.4 or 1.5 ml solution of phosphate buffered saline (pH=7.4) with 0.05% wt of Tween20) in a 37° C. bath with rotation at 70 rpm and dried at these time points.

For example, to analyze the uppermost surface only, static conditions (for example a ToF-SIMS IV (IonToF, Munster)) using a 25 Kv $Bi^{++}$ primary ion source maintained below $10^{12}$ ions per $cm^2$ is used. Where necessary a low energy electron flood gun (0.6 nA DC) is used to charge compensate insulating samples.

Cluster Secondary Ion Mass Spectrometry, may be employed for depth profiling as described Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference.

For example, a stent as described herein is obtained. The stent is prepared for SIMS analysis by cutting it longitudinally and opening it up with tweezers. The stent is then pressed into multiple layers of indium foil with the outer diameter facing outward.

TOF-SIMS depth profiling experiments are performed using an Ion-TOF IV instrument equipped with both Bi and SF5+ primary ion beam cluster sources. Sputter depth profiling is performed in the dual-beam mode, while preserving the chemical integrity of the sample. For example, the analysis source is a pulsed, 25-keV bismuth cluster ion source, which bombarded the surface at an incident angle of 45° to the surface normal. The target current is maintained at ~0.3 pÅ (+10%) pulsed current with a raster size of 200 micron×200 micron for all experiments. Both positive and negative secondary ions are extracted from the sample into a reflectron-type time-of-flight mass spectrometer. The secondary ions are then detected by a microchannel plate detector with a post-acceleration energy of 10 kV. A low-energy electron flood gun is utilized for charge neutralization in the analysis mode.

The sputter source used is a 5-keV SF5+ cluster source also operated at an incident angle of 45° to the surface normal. For thin model samples on Si, the SF5+ current is maintained at ~2.7 nÅ with a 750 micron×750 micron raster. For the thick samples on coupons and for the samples on stents, the current is maintained at 6 nA with a 500 micron× 500 micron raster. All primary beam currents are measured with a Faraday cup both prior to and after depth profiling.

All depth profiles are acquired in the noninterlaced mode with a 5-ms pause between sputtering and analysis. Each spectrum is averaged over a 7.37 second time period. The analysis is immediately followed by 15 seconds of $SF_5^+$ sputtering. For depth profiles of the surface and subsurface regions only, the sputtering time was decreased to 1 second for the 5% active agent sample and 2 seconds for both the 25% and 50% active agent samples.

Temperature-controlled depth profiles are obtained using a variable-temperature stage with Eurotherm Controls temperature controller and IPSG V3.08 software. Samples are first placed into the analysis chamber at room temperature. The samples are brought to the desired temperature under ultra high-vacuum conditions and are allowed to stabilize for 1 minute prior to analysis. All depth profiling experiments are performed at −100 degrees C. and 25 degrees C.

Infrared (IR) Spectroscopy for In-Vitro Testing

Infrared (IR) Spectroscopy such as, but not limited to, FTIR, ATR-IR and micro ATR-IR are well utilized techniques that can be applied to show the quantitative polymer content in the coating, and the distribution of polymer in the coating.

For example using FTIR, a coupon of crystalline ZnSe is coated by the processes described herein, creating a PDPDP (Polymer, Drug, Polymer, Drug, Polymer) layered coating that is about 10 microns thick. At time=0 and at at least four elution time points within a 48 day interval (e.g., 0 min., 15 min., 30 min., 1 hr, 2 hr, 4 hr, 6 hr, 8, hr, 12 hr, 16 hr, 20 hr, 24 hr, 30 hr, 36 hr and 48 hr), the sample (coated crystal) was tested by FTIR for polymer content. The sample was placed in an elution media (e.g. 10 mM Tris, 0.4 wt. % SDS, pH 7.4 or 1.5 ml solution of phosphate buffered saline (pH=7.4) with 0.05% wt of Tween20) in a 37° C. bath with bath rotation at 70 rpm and at each time point, the sample is removed from the elution media and dried (e.g. in a stream of nitrogen). FTIR spectrometry was used to quantify the polymer on the sample. After analysis, each is returned to the buffer for further elution.

In another example using FTIR, sample elution media at each time point was tested for polymer content. In this example, a coated stent was prepared that was coated by the processes described herein, creating a PDPDP (Polymer, Drug, Polymer, Drug, Polymer) layered coating that is about 10 microns thick. The coated stent was placed in an elution media (e.g. 10 mM Tris, 0.4 wt. % SDS, pH 7.4 or 1.5 ml solution of phosphate buffered saline (pH=7.4) with 0.05% wt of Tween20) in a 37° C. bath with rotation at 70 rpm. and at each time point (e.g., 0 min., 15 min, 30 min., 1 hr, 2 hr, 4 hr, 6 hr, 8, hr, 12 hr, 16 hr, 20 hr, 24 hr, 30 hr, 36 hr and 48 hr), a sample of the elution media is removed and dried onto a crystalline ZnSe window(e.g. in a stream of nitrogen). At each elution time point, the sample elution media was tested by FTIR for polymer content.

Atomic Force Microscopy (AFM)

AFM is a high resolution surface characterization technique. AFM is used in the art to provide topographical imaging, in addition when employed in Tapping Mode™ can image material and or chemical properties of the surface. The technique can be used under ambient, solution, humidified or temperature controlled conditions. Other modes of operation are well known and can be readily employed here by those skilled in the art. The AFM topography images can be run in time-lapse to characterize the surface as a function of elution time. Three-dimensionally rendered images show the surface of a coated stent, which can show holes or voids of the coating which may occur as the polymer is absorbed and the drug is eluted over time.

A stent as described herein is obtained. AFM is used to determine the drug polymer distribution. AFM may be employed as described in Ranade et al., "Physical characterization of controlled release of paclitaxel from the TAXUS Express2 drug-eluting stent" *J. Biomed. Mater. Res.* 71(4):625-634 (2004) incorporated herein in its entirety by reference.

For example a multi-mode AFM (Digital Instruments/Veeco Metrology, Santa Barbara, Calif.) controlled with Nanoscope Ina and NanoScope Extender electronics is used. Samples are examined in the dry state using AFM before elution of the drug (e.g. rapamycin). Samples are also examined at select time points through a elution period (e.g. 48 hours) by using an AFM probe-tip and flow-through stage built to permit analysis of wet samples. The wet samples are examined in the presence of the same elution medium used for in-vitro kinetic drug release analysis (e.g. PBS-Tween20, or 10 mM Tris, 0.4 wt. % SDS, pH 7.4). Saturation of the solution is prevented by frequent exchanges of the release medium with several volumes of fresh medium. TappingMode™ AFM imaging may be used to show topography (a real-space projection of the coating surface microstructure) and phase-angle changes of the AFM over the sample area to contrast differences in the material and physical structure.

Nano X-Ray Computer Tomography

Another technique that may be used to view the physical structure of a device in 3-D is Nano X-Ray Computer Tomography (e.g. such as made by SkyScan), which could be used in an elution test and/or bioabsorbability test, as described herein to show the physical structure of the coating remaining on stents at each time point, as compared to a scan prior to elution/bioabsorbtion.

pH Testing

The bioabsorbability of PLGA of a coated stent can be shown by testing the pH of an elution media (EtOH/PBS, for example) in which the coated stent is placed. Over time, a bioabsorbable PLGA coated stent (with or without the drug) will show a decreased pH until the PLGA is fully bioabsorbed by the elution media.

Figure 2:
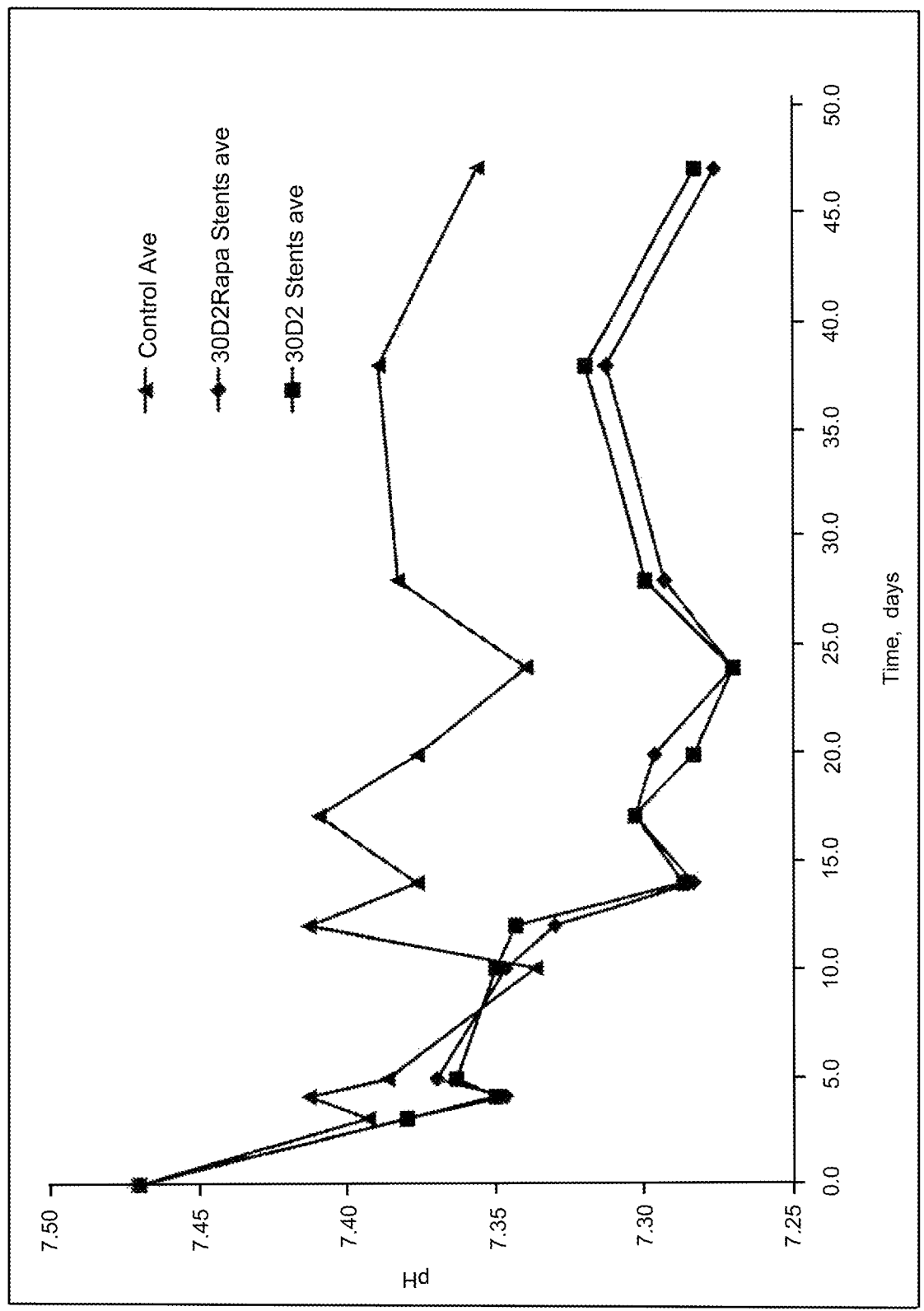
FIG. 2: Bioabsorbability testing of 50:50 PLGA-carboxylate end group (MW 10 kD) PLGA polymer coating formulations on stents by determination of pH Changes with Polymer Film Degradation in 20% Ethanol/Phosphate Buffered Saline as set forth in Example 3 described herein.
Figure 3:
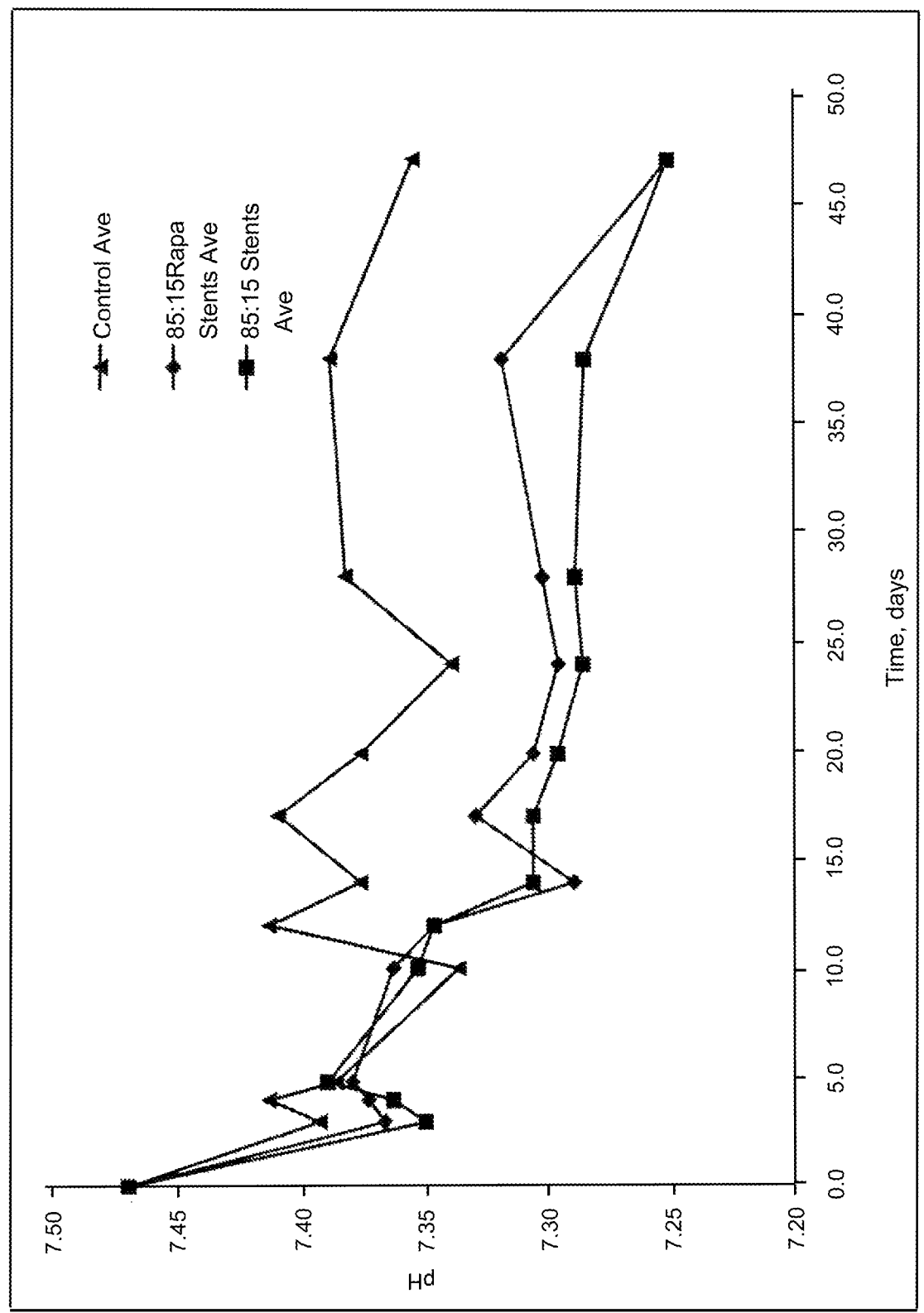
FIG. 3: Bioabsorbability testing of 85:15 (85% lactic acid, 15% glycolic acid) PLGA polymer coating formulations on stents by determination of pH Changes with Polymer Film Degradation in 20% Ethanol/Phosphate Buffered Saline as set forth in Example 3 described herein.
Figure 4:
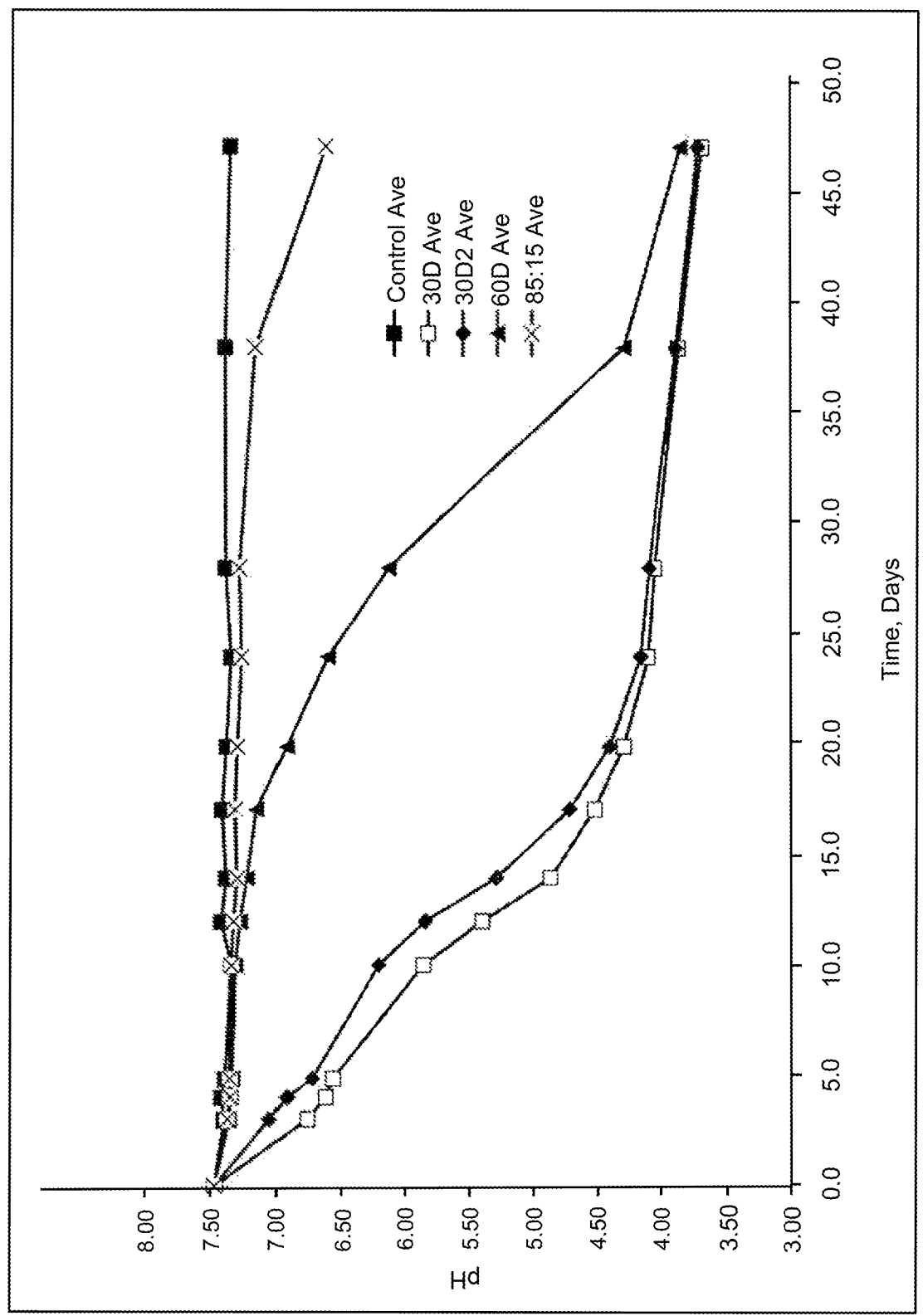
FIG. 4: Bioabsorbability testing of various PLGA polymer coating film formulations by determination of pH Changes with Polymer Film Degradation in 20% Ethanol/Phosphate Buffered Saline as set forth in Example 3 described herein.

A test was performed using stents coated with PLGA alone, stents coated with PLGA and rapamycin, PLGA films, and PLGA films containing rapamycin. The samples were put in elution media of 20% EtOH/PBS at 37° C. The elution media was tested at multiple intervals from 0 to 48 days. In FIGS. 1, 2 and 3, stents having coatings as provided herein were tested for pH over time according to this method. FIG. 4 shows results of the PLGA films (with and without rapamycin) tested according to this method. Control elution media was run in triplicate alongside the samples, and the results of this pH testing was averaged and is presented as "Control AVE" in each of the FIGS. 1-4.

In FIG. 2, the "30D2Rapa Stents ave" line represents a stent having coating according to AS1(213) of Example 1 (PDPDP) with Polymer B (50:50 PLGA-Carboxylate end group, MW ~10 kD) and rapamycin, where the coating was removed from the stent and tested in triplicate for pH changes over time in the elution media, the average of which is presented. The "30D2 Stents ave" line represents a stent having coating of only Polymer B (50:50 PLGA-Carboxylate end group, MW 10 kD) (no rapamycin), where the coating was removed from the stent and tested in triplicate for pH changes over time in the elution media, the average of which is presented.

In FIG. 1, the "60DRapa Stents ave" line represents a stent having coating according to AS1 of Example 1 (PDPDP) with Polymer A (50:50 PLGA-Ester end group, MW ~191(D) and rapamycin, where the coating was removed from the stent and tested in triplicate for pH changes over time in the elution media, the average of which is presented. The "60D Stents ave" line represents a stent having coating of only Polymer A (50:50 PLGA-Ester end group, MW ~19 kD) (no rapamycin), where the coating was removed from the stent and tested in triplicate for pH changes over time in the elution media, the average of which is presented.

In FIG. 3, the "85:15Rapa Stents ave" line represents a stent having coating according to PDPDP with a PLGA comprising 85% lactic acid, 15% glycolic acid, and rapamycin, where the coating was removed from the stent and tested in triplicate for pH changes over time in the elution media, the average of which is presented. The "85:15 Stents ave" line represents a stent having coating of only PLGA comprising 85% lactic acid, 15% glycolic acid (no rapamycin), where the coating was removed from the stent and tested in triplicate for pH changes over time in the elution media, the average of which is presented.

In FIG. 4, the "30D Ave" line represents a polymer film comprising Polymer B (50:50 PLGA-Carboxylate end group, MW ~10 kD) (no rapamycin), where the film was tested in triplicate for pH changes over time in the elution media, the average of which is presented. The "30D2 Ave" line also represents a polymer film comprising Polymer B (50:50 PLGA-Carboxylate end group, MW ~10 kD) (no rapamycin), where the film was tested in triplicate for pH changes over time in the elution media, the average of which is presented. The "60D Ave" line represents a polymer film comprising Polymer A (50:50 PLGA-Ester end group, MW ~19 kD) (no rapamycin), where the film was tested in triplicate for pH changes over time in the elution media, the average of which is presented. The "85:15 Ave" line represents a polymer film comprising PLGA comprising 85% lactic acid, 15% glycolic acid (no rapamycin), where the film was tested in triplicate for pH changes over time in the elution media, the average of which is presented. To create the polymer films in FIG. 4, the polymers were dissolved in methylene chloride, THF, and ethyl acetate. The films that were tested had the following average thicknesses and masses, 30D-152.4 um, 12.0 mg; 30D2-127.0 um, 11.9 mg; 60D-50.8 um, 12.4 mg; 85:15-127 um, 12.5 mg.

Example 4: Visualization of Polymer/Active Agent Layers Coating a Device Raman Spectroscopy As discussed in example 2, Raman spectroscopy can be applied to characterize the chemical structure and relative concentrations of drug and polymer coatings. For example, confocal Raman Spectroscopy/microscopy can be used to characterize the relative drug to polymer ratio at the outer ~1 μm of the coated surface. In addition confocal Raman x-z or z (maps or line scans) microscopy can be applied to characterize the relative drug to polymer ratio as a function of depth. Additionally cross-sectioned samples can be analysed Raman spectroscopy and other analytical techniques such as described in Balss, et al., "Quantitative spatial distribution of sirolimus and polymers in drug-eluting stents using confocal Raman microscopy" *J. of Biomedical Materials Research Part A*, 258-270 (2007), incorporated in its entirety herein by reference, and/or described in Belu et al., "Three- Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

A sample (a coated stent) is prepared as described herein. Images are taken on the coating using Raman Spectroscopy. Alternatively, a coated coupon could be tested in this method. To test a sample using Raman microscopy and in particular confocal Raman microscopy, it is understood that to get appropriate Raman high resolution spectra sufficient acquisition time, laser power, laser wavelength, sample step size and microscope objective need to be optimized.

For example a WITec CRM 200 scanning confocal Raman microscope using a Nd:YAG laser at 532 nm is applied in the Raman imaging mode to give x-z maps. The sample is placed upon a piezoelectrically driven table, the laser light is focused upon the sample using a 100× dry objective (numerical aperture 0.90), and the finely focused laser spot is scanned into the sample. As the laser scans the sample, over each 0.33 micron interval a Raman spectrum with high signal to noise is collected using 0.3 Seconds of integration time. Each confocal cross-sectional image of the coatings displays a region 70 μm wide by 10 μm deep, and results from the gathering of 6300 spectra with a total imaging time of 32 min. Multivariate analysis using reference spectra from samples of rapamycin and polymer are used to deconvolve the spectral data sets, to provide chemical maps of the distribution.

In another test, spectral depth profiles (x-z maps) of samples are performed with a CRM200 microscope system from WITec Instruments Corporation (Savoy, Ill.). The instrument is equipped with a Nd:YAG frequency doubled laser (532 excitation), a single monochromator (Acton) employing a 600 groove/mm grating and a thermoelectrically cooled 1024 by 128 pixel array CCD camera (Andor Technology). The microscope is equipped with appropriate collection optics that include a holographic laser bandpass rejection filter (Kaiser Optical Systems Inc.) to minimize Rayleigh scatter into the monochromator. The Raman scattered light are collected with a 50 micron optical fiber. Using the "Raman Spectral Imaging" mode of the instrument, spectral images are obtained by scanning the sample in the x, z direction with a piezo driven xyz scan stage and collecting a spectrum at every pixel. Typical integration times are 0.3 s per pixel. The spectral images are 4800 total spectra corresponding to a physical scan dimension of 40 by 20 microns. For presentation of the confocal Raman data, images are generated based on unique properties of the spectra (i.e. integration of a Raman band, band height intensity, or band width). The microscope stage is modified with a custom-built sample holder that positioned and rotated the stents around their primary axis. The x direction is defined as the direction running parallel to the length of the stent and the z direction refers to the direction penetrating through the coating from the air-coating to the coating-metal interface. Typical laser power is <10 mW on the sample stage. All experiments can be conducted with a plan achromat objective, 100×$N_A$=0.9 (Nikon).

Samples (n=5) comprising stents made of L605 (0.05-0.15% C, 1.00-2.00% Mn, maximum 0.040% Si, maximum 0.030% P, maximum 0.3% S, 19.00-21.00% Cr, 9.00-11.00% Ni, 14.00-16.00% W, 3.00% Fe, and Bal. Co) and having coatings as described herein and/or produced by methods described herein can be analyzed. For each sample, three locations are selected along the stent length. The three locations are located within one-third portions of the stents so that the entire length of the stent are represented in the data. The stent is then rotated 180 degrees around the circumference and an additional three locations are sampled along the length. In each case, the data is collected from the strut portion of the stent. Six random spatial locations are also profiled on coated coupon samples made of L605 and having coatings as described herein and/or produced by methods described herein. The Raman spectra of each individual component present in the coatings are also collected for comparison and reference. Using the instrument software, the average spectra from the spectral image data are calculated by selecting the spectral image pixels that are exclusive to each layer. The average spectra are then exported into GRAMS/AI v. 7.02 software (Thermo Galactic) and the appropriate Raman bands are fit to a Voigt function. The band areas and shift positions are recorded.

The pure component spectrum for each component of the coating (e.g. drug, polymer) are also collected at 532 and 785 nm excitation. The 785 nm excitation spectra are collected with a confocal Raman microscope (WITec Instruments Corp. Savoy, Ill.) equipped with a 785 nm diode laser, appropriate collection optics, and a back-illuminated thermoelectrically cooled 1024×128 pixel array CCD camera optimized for visible and infrared wavelengths (Andor Technology).

X-Ray Photoelectron Spectroscopy (XPS)

XPS can be used to quantitatively determine elemental species and chemical bonding environments at the outer 5-10 nm of sample surface. The technique can be operated in spectroscopy or imaging mode. When combined with a sputtering source XPS can be utilized to give depth profiling chemical characterization. XPS (ESCA) and other analytical techniques such as described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

For example, in one test, a sample comprising a stent coated by methods described herein and/or a device as described herein is obtained. XPS analysis is performed on a sample using a Physical Electronics Quantum 2000 Scanning ESCA. The monochromatic Al Kα source is operated at 15 kV with a power of 4.5 W. The analysis is done at a 45° take off angle. Three measurements are taken along the length of each sample with the analysis area 20 microns in diameter. Low energy electron and Ar$^+$ ion floods are used for charge compensation.

Time of Flight Secondary Ion Mass Spectrometery (TOF-SIMS)

TOF-SIMS can be used to determine molecular species (drug and polymer) at the outer 1-2 nm of sample surface when operated under static conditions. The technique can be operated in spectroscopy or imaging mode at high spatial resolution. Additionally cross-sectioned samples can be analysed. When operated under dynamic experimental conditions, known in the art, depth profiling chemical characterization can be achieved.

For example, to analyze the uppermost surface only, static conditions (for example a ToF-SIMS IV (IonToF, Munster)) using a 25 Kv Br$^{++}$ primary ion source maintained below $10^{12}$ ions per cm$^2$ is used. Where necessary a low energy electron flood gun (0.6 nA DC) is used to charge compensate insulating samples.

Cluster Secondary Ion Mass Spectrometry, may be employed for depth profiling as described Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference.

For example, a stent as described herein is obtained. The stent is prepared for SIMS analysis by cutting it longitudinally and opening it up with tweezers. The stent is then pressed into multiple layers of indium foil with the outer diameter facing outward.

TOF-SIMS depth profiling experiments are performed using an Ion-TOF IV instrument equipped with both Bi and SF5+ primary ion beam cluster sources. Sputter depth profiling is performed in the dual-beam mode, whilst preserving the chemical integrity of the sample. The analysis source is a pulsed, 25-keV bismuth cluster ion source, which bombarded the surface at an incident angle of 45° to the surface normal. The target current is maintained at ~0.3 pÅ (+10%) pulsed current with a raster size of 200 um×200 um for all experiments. Both positive and negative secondary ions are extracted from the sample into a reflectron-type time-of-flight mass spectrometer. The secondary ions are then detected by a microchannel plate detector with a post-acceleration energy of 10 kV. A low-energy electron flood gun is utilized for charge neutralization in the analysis mode.

The sputter source used is a 5-keV SF5+ cluster source also operated at an incident angle of 45° to the surface normal. For thin model samples on Si, the SF5+ current is maintained at ~2.7 nÅ with a 750 um×750 um raster. For the thick samples on coupons and for the samples on stents, the current is maintained at 6 nA with a 500 um×500 um raster. All primary beam currents are measured with a Faraday cup both prior to and after depth profiling.

All depth profiles are acquired in the noninterlaced mode with a 5-ms pause between sputtering and analysis. Each spectrum is averaged over a 7.37 second time period. The analysis is immediately followed by 15 seconds of $SF_5^+$ sputtering. For depth profiles of the surface and subsurface regions only, the sputtering time was decreased to 1 second for the 5% active agent sample and 2 seconds for both the 25% and 50% active agent samples.

Temperature-controlled depth profiles are obtained using a variable-temperature stage with Eurotherm Controls temperature controller and IPSG V3.08 software. Samples are first placed into the analysis chamber at room temperature. The samples are brought to the desired temperature under ultra high-vacuum conditions and are allowed to stabilize for 1 minute prior to analysis. All depth profiling experiments are performed at −100 C and 25 C.

Atomic Force Microscopy (AFM)

AFM is a high resolution surface characterization technique. AFM is used in the art to provide topographical imaging, in addition when employed in Tapping Mode™ can image material and or chemical properties of the surface. Additionally cross-sectioned samples can be analyzed. The technique can be used under ambient, solution, humidified or temperature controlled conditions. Other modes of operation are well known and can be readily employed here by those skilled in the art.

A stent as described herein is obtained. AFM is used to determine the structure of the drug polymer layers. AFM may be employed as described in Ranade et al., "Physical characterization of controlled release of paclitaxel from the TAXUS Express2 drug-eluting stent" *J. Biomed. Mater. Res.* 71(4):625-634 (2004) incorporated herein in its entirety by reference.

Polymer and drug morphologies, coating composition, at least may be determined using atomic force microscopy (AFM) analysis. A multi-mode AFM (Digital Instruments/ Veeco Metrology, Santa Barbara, Calif.) controlled with Nanoscope Ina and NanoScope Extender electronics is used. Samples are examined in the dry state using AFM before elution of the drug (e.g. rapamycin). Samples are also examined at select time points through a elution period (e.g. 48 hours) by using an AFM probe-tip and flow-through stage built to permit analysis of wet samples. The wet samples are examined in the presence of the same elution medium used for in-vitro kinetic drug release analysis (e.g. PBS-Tween20, or 10 mM Tris, 0.4 wt. % SDS, pH 7.4). Saturation of the solution is prevented by frequent exchanges of the release medium with several volumes of fresh medium. Tapping-Mode™ AFM imaging may be used to show topography (a real-space projection of the coating surface microstructure) and phase-angle changes of the AFM over the sample area to contrast differences in the materials properties. The AFM topography images can be three-dimensionally rendered to show the surface of a coated stent, which can show holes or voids of the coating which may occur as the polymer is absorbed and the drug is eluted over time, for example.

Scanning Electron Microscopy (SEM) with Focused Ion Beam (FIB) Milling Stents as described herein, and or produced by methods described herein are visualized using SEM-FIB. Alternatively, a coated coupon could be tested in this method. Focused ion beam FIB is a tool that allows precise site-specific sectioning, milling and depositing of materials. FIB can be used in conjunction with SEM, at ambient or cryo conditions, to produce in-situ sectioning followed by high-resolution imaging. FIB-SEM can produce a cross-sectional image of the polymer and drug layers on the stent. The image can be used to quantitate the thickness of the layers and uniformity of the layer thickness at manufacture and at time points after stenting (or after in-vitro elution at various time points).

A FEI Dual Beam Strata 235 FIB/SEM system is a combination of a finely focused Ga ion beam (FIB) accelerated by 30 kV with a field emission electron beam in a scanning electron microscope instrument and is used for imaging and sectioning the stents. Both beams focus at the same point of the sample with a probe diameter less than 10 nm. The FIB can also produce thinned down sections for TEM analysis.

To prevent damaging the surface of the stent with incident ions, a Pt coating is first deposited via electron beam assisted deposition and ion beam deposition prior to FIB sectioning. For FIB sectioning, the Ga ion beam is accelerated to 30 kV and the sectioning process is about 2 h in duration. Completion of the FIB sectioning allows one to observe and quantify by SEM the thickness of the polymer layers that are, for example, left on the stent as they are absorbed.

Example 5: Analysis of the Thickness of a Device Coating

Analysis can be determined by either in-situ analysis or from cross-sectioned samples.

X-Ray Photoelectron Spectroscopy (XPS)

XPS can be used to quantitatively determine the presence of elemental species and chemical bonding environments at the outer 5-10 nm of sample surface. The technique can be operated in spectroscopy or imaging mode. When combined with a sputtering source XPS can be utilized to give depth profiling chemical characterization. XPS (ESCA) and other analytical techniques such as described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

Thus, in one test, a sample comprising a stent coated by methods described herein and/or a device as described herein is obtained. XPS analysis is done on a sample using a Physical Electronics Quantum 2000 Scanning ESCA. The monochromatic Al Kα source is operated at 15 kV with a power of 4.5 W. The analysis is done at a 45° take off angle. Three measurements are taken along the length of each sample with the analysis area ~20 microns in diameter. Low energy electron and Ar+ ion floods are used for charge compensation.

Time of Flight Secondary Ion Mass Spectrometery

TOF-SIMS can be used to determine molecular species (drug and polymer) at the outer 1-2 nm of sample surface when operated under static conditions. The technique can be operated in spectroscopy or imaging mode at high spatial resolution. Additionally cross-sectioned samples can be analysed. When operated under dynamic experimental conditions, known in the art, depth profiling chemical characterization can be achieved.

For example, under static conditions (for example a ToF-SIMS IV (IonToF, Munster)) using a 25 Kv $Br^{++}$ primary ion source maintained below $10^{12}$ ions per $cm^2$ is used. Where necessary a low energy electron flood gun (0.6 nA DC) is used to charge compensate insulating samples.

Cluster Secondary Ion Mass Spectrometry, may be employed for depth profiling as described Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference.

A stent as described herein is obtained. The stent is prepared for SIMS analysis by cutting it longitudinally and opening it up with tweezers. The stent is then pressed into multiple layers of iridium foil with the outer diameter facing outward.

TOF-SIMS experiments are performed on an Ion-TOF IV instrument equipped with both Bi and SF5+ primary ion beam cluster sources. Sputter depth profiling is performed in the dual-beam mode. The analysis source is a pulsed, 25-keV bismuth cluster ion source, which bombarded the surface at an incident angle of 45° to the surface normal. The target current is maintained at ~0.3 pÅ (+10%) pulsed current with a raster size of 200 um×200 um for all experiments. Both positive and negative secondary ions are extracted from the sample into a reflectron-type time-of-flight mass spectrometer. The secondary ions are then detected by a microchannel plate detector with a post-acceleration energy of 10 kV. A low-energy electron flood gun is utilized for charge neutralization in the analysis mode.

The sputter source used is a 5-keV SF5+ cluster source also operated at an incident angle of 45° to the surface normal. For thin model samples on Si, the SF5+ current is maintained at ~2.7 nÅ with a 750 um×750 um raster. For the thick samples on coupons and for the samples on stents, the current is maintained at 6 nA with a 500 um×500 um raster. All primary beam currents are measured with a Faraday cup both prior to and after depth profiling.

All depth profiles are acquired in the noninterlaced mode with a 5-ms pause between sputtering and analysis. Each spectrum is averaged over a 7.37 second time period. The analysis is immediately followed by 15 seconds of $SF_5^+$ sputtering. For depth profiles of the surface and subsurface regions only, the sputtering time was decreased to 1 second for the 5% active agent sample and 2 seconds for both the 25% and 50% active agent samples.

Temperature-controlled depth profiles are obtained using a variable-temperature stage with Eurotherm Controls temperature controller and IPSG V3.08 software. samples are first placed into the analysis chamber at room temperature. The samples are brought to the desired temperature under ultra high-vacuum conditions and are allowed to stabilize for 1 minute prior to analysis. All depth profiling experiments are performed at −100 C and 25 C.

Atomic Force Microscopy (AFM)

AFM is a high resolution surface characterization technique. AFM is used in the art to provide topographical imaging, in addition when employed in Tapping Mode™ can image material and or chemical properties of the surface. Additionally cross-sectioned samples can be analyzed.

A stent as described herein is obtained. AFM may alternatively be employed as described in Ranade et al., "Physical characterization of controlled release of paclitaxel from the TAXUS Express2 drug-eluting stent" *J. Biomed. Mater. Res.* 71(4):625-634 (2004) incorporated herein in its entirety by reference.

Polymer and drug morphologies, coating composition, and cross-sectional thickness at least may be determined using atomic force microscopy (AFM) analysis. A multi-mode AFM (Digital Instruments/Veeco Metrology, Santa Barbara, Calif.) controlled with Nanoscope Ma and Nano-Scope Extender electronics is used TappingMode™ AFM imaging may be used to show topography (a real-space projection of the coating surface microstructure) and phase-angle changes of the AFM over the sample area to contrast differences in the materials properties. The AFM topography images can be three-dimensionally rendered to show the surface of a coated stent or cross-section.

Scanning Electron Microscopy (SEM) with Focused Ion Beam (FIB)

Stents as described herein, and/or produced by methods described herein, are visualized using SEM-FIB analysis. Alternatively, a coated coupon could be tested in this method. Focused ion beam FIB is a tool that allows precise site-specific sectioning, milling and depositing of materials. FIB can be used in conjunction with SEM, at ambient or cryo conditions, to produce in-situ sectioning followed by high-resolution imaging. FIB-SEM can produce a cross-sectional image of the polymer layers on the stent. The image can be used to quantitate the thickness of the layers as well as show whether there is uniformity of the layer thickness at manufacture and at time points after stenting (or after in-vitro elution at various time points).

A FEI Dual Beam Strata 235 FIB/SEM system is a combination of a finely focused Ga ion beam (FIB) accelerated by 30 kV with a field emission electron beam in a scanning electron microscope instrument and is used for imaging and sectioning the stents. Both beams focus at the same point of the sample with a probe diameter less than 10 nm. The FIB can also produce thinned down sections for TEM analysis.

To prevent damaging the surface of the stent with incident ions, a Pt coating is first deposited via electron beam assisted deposition and ion beam deposition prior to FIB sectioning. For FIB sectioning, the Ga ion beam is accelerated to 30 kV and the sectioning process is about 2 h in duration. Completion of the FIB sectioning allows one to observe and quantify by SEM the thickness of the polymer layers that are, for example, left on the stent as they are absorbed.

Interferometry

Interferometry may additionally and/or alternatively used to determine the thickness of the coating as noted in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

Ellipsometry

Ellipsometry is sensitive measurement technique for coating analysis on a coupon. It uses polarized light to probe the dielectric properties of a sample. Through an analysis of the state of polarization of the light that is reflected from the sample the technique allows the accurate characterization of the layer thickness and uniformity. Thickness determinations ranging from a few angstroms to tens of microns are possible for single layers or multilayer systems. See, for example, Jewell, et al., "Release of Plasmid DNA from Intravascular Stents Coated with Ultrathin Multilayered Polyelectrolyte Films" *Biomacromolecules.* 7: 2483-2491 (2006) incorporated herein in its entirety by reference.

Scanning Electron Microscopy (SEM)

A sample coated stent described herein is obtained. Thickness of the coating can be assessed using this analytical technique. The thickness the coating on multiple struts or on a single strut may be taken to characterize the coating and stent. The thickness of the coating can be observed by SEM using a Hitachi S-4800 with an accelerating voltage of 800V. Various magnifications are used. SEM can provide top-down and cross-section images at various magnifications.

Coating thicknesses on a particular surface of the stent (e.g. a sidewall, an abluminal surface, a luminal surface) may be taken as a single measurement along the particular surface, for example, near the center of the surface, or may be an average of a plurality of thicknesses measured along the particular surface. A sidewall surface coating thickness may be an average of thicknesses measured on either or both sidewalls, or it may be a single measurement along a single sidewall.

Figure 5:
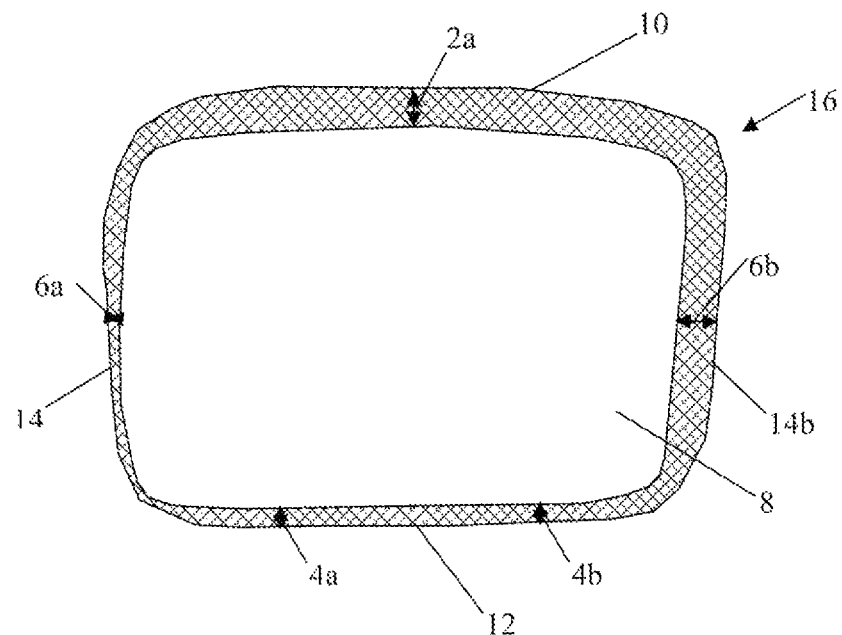
FIG. 5 depicts coating thicknesses of a coated stent of an embodiment of the invention.

In one test, stents were produced as described herein. The stent was coated with sirolimus in about a 1 to 4 ratio with nominally 50:50 poly(d,l-lacitde-co-glycolide) bioabsorbable polymer. The coating process applied potential to the stent at about +2 kV and used oppositely polarized drug particles at lower magnitude potential. The total spray time was about 40 seconds pulsed in a sequence of 3 unequal times. The sprayed polymer was first dissolved in a supercritical gas and diluted to a concentration of approximately two milligrams per milliliter. The powder produced during the spray sequence was collected on the stents over an approximately equal time interval across all three spray pulses. The drug was burst into the chamber using a nitrogen back pressure of approximately 250 psi. The coating thickness was measured using SEM techniques described of a cross section of the stent. The results of the testing are shown in FIG. 5. Thicknesses were taken with the following settings: EAG 10.0 kV, 15.5 mm×700. FIG. 5 depicts coating thicknesses of a coated stent 16 comprising a stent 8 and a coating (depicted as cross-hatched in the figure) of an embodiment of the invention. Depicted is a coated stent 16 having an abluminal surface 10, a luminal surface 12, and two sidewall surfaces 14a, 14b. Coating thicknesses were measured in this test in one location 2a of the abluminal surface, for which thickness was recorded to be 9.07 microns. Coating thicknesses were measured in this test in two locations 4a, 4b of the luminal surface, for which thicknesses were recorded to be 3.69 microns, and 4.54 microns, respectively, with an average luminal coating thickness of 4.115 microns. Coating thicknesses were measured in this test in two locations 6a, 6b of the sidewall surfaces, for which thicknesses were recorded to be 2.83 microns, 8.79 microns, respectively, with an average sidewall coating thickness of 5.81 microns. Thus, for this test, the coating thickness ratio Abluminal: Luminal was determined to be 9.07:4.115, which equates to 68.79:31.21. This is within a coating ratio as described herein of about 70:30 including a variation of 5% (i.e. 5% of 100). This coated stent also meets a coating ratio specification (abluminal:luminal) as described herein of at most 70:30. This coated stent also meets a coating ratio specification (abluminal:luminal) as described herein of at most 80:20. This coated stent also meets a coating ratio specification (abluminal:luminal) as described herein of at most 90:10.

Figure 6:
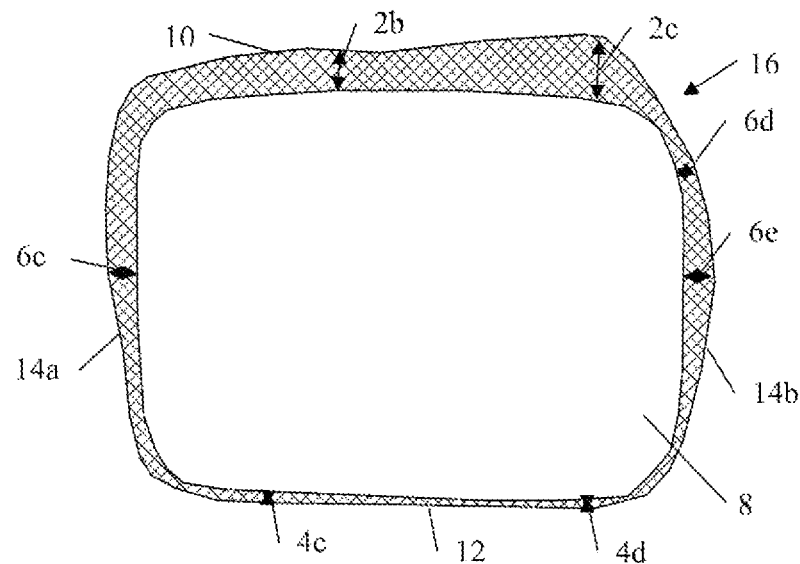
FIG. 6 depicts coating thicknesses of a coated stent of an embodiment of the invention.

In another test, stents were produced as described herein. The stent was coated with sirolimus in about a 1 to 4 ratio with nominally 50:50 poly(d,l-lacitde-co-glycolide) bioabsorbable polymer. The coating process applied potential to the stent at about +2 kV and used oppositely polarized drug particles at lower magnitude potential. The total spray time was about 40 seconds pulsed in a sequence of 3 unequal times. The sprayed polymer was first dissolved in a supercritical gas and diluted to a concentration of approximately two milligrams per milliliter. The powder produced during the spray sequence was collected on the stents over an approximately equal time interval across all three spray pulses. The drug was burst into the chamber using a nitrogen back pressure of approximately 250 psi. The coating thickness was measured using SEM techniques described of a cross section of the stent. The results of the testing are shown in FIG. 6. Thicknesses were taken with the following settings: EAG 10.0 kV, 15.5 mm×700. FIG. 6 depicts coating thicknesses of a coated stent 16 comprising a stent 8 and a coating (depicted as cross-hatched in the figure) of an embodiment of the invention. Depicted is a coated stent 16 having an abluminal surface 10, a luminal surface 12, and two sidewall surfaces 14a, 14b. Coating thicknesses were measured in this test in two locations 2b, 2c of the abluminal surface, for which thicknesses were recorded to be 7.94 microns, and 14.2 microns, respectively, with an average abluminal coating thickness of 11.07 microns. Coating thicknesses were measured in this test in two locations 4c, 4d of the luminal surface, for which thicknesses were recorded to be 1.98 microns, and 2.55 microns, respectively, with an average luminal coating thickness of 2.265 microns. Coating thicknesses were measured in this test in three locations 6c, 6d, and 6e of the sidewall surfaces, for which thicknesses were recorded to be 5.67 microns, 5.76 microns, and 3.32 microns, respectively, with an average sidewall coating thickness of 4.917 microns. Thus, for this test, the coating thickness ratio Abluminal: Luminal was determined to be 11.07:2.265, which equates to 83.01:16.99. This also meets a ratio specification (abluminal:luminal) as described herein of at most 80:20 (wherein there is a 5% variation allowed in the specification i.e. 5% of 100). This coated stent also meets a coating ratio specification (abluminabluminal) as described herein of at most 90:10.

Example 6: Analysis of the Thickness of a Device

Scanning Electron Microscopy (SEM)

A sample coated stent described herein is obtained. Thickness of the device can be assessed using this analytical technique. The thickness of multiple struts were taken to ensure reproducibility and to characterize the coating and stent. The thickness of the coating was observed by SEM using a Hitachi S-4800 with an accelerating voltage of 800V. Various magnifications are used. SEM can provide top-down and cross-section images at various magnifications.

Nano X-Ray Computer Tomography

Another technique that may be used to view the physical structure of a device in 3-D is Nano X-Ray Computer Tomography (e.g. such as made by SkyScan).

Example 7: Determination of the Type or Composition of a Polymer Coating a Device Nuclear Magnetic Resonance (NMR)

Composition of the polymer samples before and after elution can be determined by $^1$H NMR spectrometry as described in Xu et al., "Biodegradation of poly(l-lactide-co-glycolide tube stents in bile" Polymer *Degradation and Stability.* 93:811-817 (2008) incorporated herein in its entirety by reference. Compositions of polymer samples are determined for example using a 300M Bruker spectrometer with d-chloroform as solvent at room temperature.

Raman Spectroscopy

FT-Raman or confocal raman microscopy can be employed to determine composition.

For example, a sample (a coated stent) is prepared as described herein. Images are taken on the coating using Raman Spectroscopy. Alternatively, a coated coupon could be tested in this method. To test a sample using Raman microscopy and in particular confocal Raman microscopy, it is understood that to get appropriate Raman high resolution spectra sufficient acquisition time, laser power, laser wavelength, sample step size and microscope objective need to be optimized. Raman spectroscopy and other analytical techniques such as described in Balss, et al., "Quantitative spatial distribution of sirolimus and polymers in drug-eluting stents using confocal Raman microscopy" *J. of Biomedical Materials Research Part A,* 258-270 (2007), incorporated in its entirety herein by reference, and/or described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

For example a WITec CRM 200 scanning confocal Raman microscope using a Nd:YAG laser at 532 nm is applied in the Raman imaging mode. The sample is placed upon a piezoelectrically driven table, the laser light is focused upon the sample using a 100× dry objective (numerical aperture 0.90), and the finely focused laser spot is scanned into the sample. As the laser scans the sample, over each 0.33 micron interval a Raman spectrum with high signal to noise is collected using 0.3 Seconds of integration time. Each confocal cross-sectional image of the coatings displays a region 70 µm wide by 10 µm deep, and results from the gathering of 6300 spectra with a total imaging time of 32 min. Multivariate analysis using reference spectra from samples of rapamycin (amorphous and crystalline) and polymer references are used to deconvolve the spectral data sets, to provide chemical maps of the distribution.

In another test, spectral depth profiles of samples are performed with a CRM200 microscope system from WITec Instruments Corporation (Savoy, Ill.). The instrument is equipped with a NdYAG frequency doubled laser (532 excitation), a single monochromator (Acton) employing a 600 groove/mm grating and a thermoelectrically cooled 1024 by 128 pixel array CCD camera (Andor Technology). The microscope is equipped with appropriate collection optics that include a holographic laser bandpass rejection filter (Kaiser Optical Systems Inc.) to minimize Rayleigh scatter into the monochromator. The Raman scattered light are collected with a 50 micron optical fiber. Using the "Raman Spectral Imaging" mode of the instrument, spectral images are obtained by scanning the sample in the x, z direction with a piezo driven xyz scan stage and collecting a spectrum at every pixel. Typical integration times are 0.3 s per pixel. The spectral images are 4800 total spectra corresponding to a physical scan dimension of 40 by 20 microns. For presentation of the confocal Raman data, images are generated base don unique properties of the spectra (i.e. integration of a Raman band, band height intensity, or band width). The microscope stage is modified with a custom-built sample holder that positioned and rotated the stents around their primary axis. The x direction is defined as the direction running parallel to the length of the stent and the z direction refers to the direction penetrating through the coating from the air-coating to the coating-metal interface. Typical laser power is <10 mW on the sample stage. All experiments can be conducted with a plan achromat objective, 100×$N_A$=0.9 (Nikon).

Samples (n=5) comprising stents made of L605 and having coatings as described herein and/or produced by methods described herein can be analyzed. For each sample, three locations are selected along the stent length. The three locations are located within one-third portions of the stents so that the entire length of the stent are represented in the data. The stent is then rotated 180 degrees around the circumference and an additional three locations are sampled along the length. In each case, the data is collected from the strut portion of the stent. Six random spatial locations are also profiled on coated coupon samples made of L605 and having coatings as described herein and/or produced by methods described herein. The Raman spectra of each individual component present in the coatings are also collected for comparison and reference. Using the instrument software, the average spectra from the spectral image data are calculated by selecting the spectral image pixels that are exclusive to each layer. The average spectra are then exported into GRAMS/AI v. 7.02 software (Thermo Galactic) and the appropriate Raman bands are fit to a Voigt function. The band areas and shift positions are recorded.

The pure component spectrum for each component of the coating (e.g. drug, polymer) are also collected at 532 and 785 nm excitation. The 785 nm excitation spectra are collected with a confocal Raman microscope (WITec Instruments Corp. Savoy, Ill.) equipped with a 785 nm diode laser, appropriate collection optics, and a back-illuminated thermoelectrically cooled 1024×128 pixel array CCD camera optimized for visible and infrared wavelengths (Andor Technology).

Time of Flight Secondary Ion Mass Spectrometery

TOF-SIMS can be used to determine molecular species (drug and polymer) at the outer 1-2 nm of sample surface when operated under static conditions. The technique can be operated in spectroscopy or imaging mode at high spatial resolution. Additionally cross-sectioned samples can be analysed. When operated under dynamic experimental conditions, known in the art, depth profiling chemical characterization can be achieved.

For example, under static conditions (for example a ToF-SIMS IV (IonToF, Munster)) using a 25 Kv $Br^{++}$ primary ion source maintained below $10^{12}$ ions per $cm^2$ is used. Where necessary a low energy electron flood gun (0.6 nA DC) is used to charge compensate insulating samples.

Cluster Secondary Ion Mass Spectrometry, may be employed as described Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference.

A stent as described herein is obtained. The stent is prepared for SIMS analysis by cutting it longitudinally and opening it up with tweezers. The stent is then pressed into multiple layers of iridium foil with the outer diameter facing outward.

TOF-SIMS experiments are performed on an Ion-TOF IV instrument equipped with both Bi and SF5+ primary ion beam cluster sources. Sputter depth profiling is performed in the dual-beam mode. The analysis source is a pulsed, 25-keV bismuth cluster ion source, which bombarded the surface at an incident angle of 45° to the surface normal. The target current is maintained at ~0.3 pÅ (+10%) pulsed current with a raster size of 200 um×200 um for all experiments. Both positive and negative secondary ions are extracted from the sample into a reflectron-type time-of-flight mass spectrometer. The secondary ions are then detected by a microchannel plate detector with a post-acceleration energy of 10 kV. A low-energy electron flood gun is utilized for charge neutralization in the analysis mode.

The sputter source used is a 5-keV SF5+ cluster source also operated at an incident angle of 45° to the surface normal. For thin model samples on Si, the SF5+ current is maintained at ~2.7 nÅ with a 750 um×750 um raster. For the thick samples on coupons and for the samples on stents, the current is maintained at 6 nA with a 500 um×500 um raster. All primary beam currents are measured with a Faraday cup both prior to and after depth profiling All depth profiles are acquired in the noninterlaced mode with a 5-ms pause between sputtering and analysis. Each spectrum is averaged over a 7.37 second time period. The analysis is immediately followed by 15 seconds of $SF_5^+$ sputtering. For depth profiles of the surface and subsurface regions only, the sputtering time was decreased to 1 second for the 5% active agent sample and 2 seconds for both the 25% and 50% active agent samples.

Temperature-controlled depth profiles are obtained using a variable-temperature stage with Eurotherm Controls temperature controller and IPSG V3.08 software. Samples are first placed into the analysis chamber at room temperature. The samples are brought to the desired temperature under ultra high-vacuum conditions and are allowed to stabilize for 1 minute prior to analysis. All depth profiling experiments are performed at −100 C and 25 C Atomic Force Microscopy (AFM)

AFM is a high resolution surface characterization technique. AFM is used in the art to provide topographical imaging, in addition when employed in Tapping Mode™ can image material and or chemical properties of the surface. Additionally cross-sectioned samples can be analyzed. Coating composition may be determined using Tapping Mode™ atomic force microscopy (AFM) analysis. Other modes of operation are well known and can be employed here by those skilled in the art.

A stent as described herein is obtained. AFM may be employed as described in Ranade et al., "Physical characterization of controlled release of paclitaxel from the TAXUS Express2 drug-eluting stent" *J. Biomed. Mater. Res.* 71(4):625-634 (2004) incorporated herein in its entirety by reference.

Polymer and drug morphologies, coating composition, at least may be determined using atomic force microscopy (AFM) analysis. A multi-mode AFM (Digital Instruments/ Veeco Metrology, Santa Barbara, Calif.) controlled with Nanoscope Ina and NanoScope Extender electronics is used.

TappingMode™ AFM imaging may be used to show topography (a real-space projection of the coating surface microstructure) and phase-angle changes of the AFM over the sample area to contrast differences in the materials properties.

Infrared (IR) Spectroscopy for In-Vitro Testing

Infrared (IR) Spectroscopy using FTIR, ATR-IR or micro ATR-IR can be used to identify polymer composition by comparison to standard polymer reference spectra.

Example 8: Determination and Detection of Coating Conformality Including Adherence and/or Contact The ability to uniformly coat devices, e.g., pre- and post-expansion stents, and balloons, with controlled composition and thickness using electrostatic capture in a rapid expansion of supercritical solution (RESS) experimental series has been demonstrated.

Scanning Electron Microscopy (SEM)

Devices are observed by SEM using a Hitachi S-4800 with an accelerating voltage of 800V. Various magnifications are used to evaluate the integrity, especially at high strain regions. SEM can provide top-down and cross-section images at various magnifications. Coating uniformity and thickness can also be assessed using this analytical technique. Coating conformality, contact and/or adherence to the substrate may also be assessed using this analytical technique. Various magnifications are used to evaluate the integrity, especially at high strain regions of the substrate and or device generally. SEM can provide top-down and cross-section images at various magnifications to determine if a broken piece of the device and/or substrate penetrated the coating.

Pre- and post-inflation balloons, for example, may be observed by SEM using a Hitachi S-4800 with an accelerating voltage of 800V. Various magnifications may be used to evaluate the integrity of the layers, and or of the coating, and or of the substrate, or device integrity (to detect broken substrate piece or device piece and/or penetration of the coating by such broken piece(s)) or of coating conformality including, for example contact of the coating to the stent and/or adherence of the coating to the stent at various time points (post-manufacture, post-crimping, post simulated delivery, pre and/or post expansion of the stent).

Scanning Electron Microscopy (SEM) with Focused Ion Beam (FIB)

Devices as described herein, and/or produced by methods described herein, are visualized using SEM-FIB analysis. Alternatively, a coated coupon could be tested in this method. Focused ion beam FIB is a tool that allows precise site-specific sectioning, milling and depositing of materials. FIB can be used in conjunction with SEM, at ambient or cryo conditions, to produce in-situ sectioning followed by high-resolution imaging. Cross-sectional FIB images may be acquired, for example, at 7000× and/or at 20000× magnification. An even coating of consistent thickness is visible. A device that has a broken piece may be imaged using this method to determine whether the broken piece penetrated the coating. Coating conformality may be assessed using this technique, including, for example, visualization of contact of the coating to the stent and/or adherence of the coating to the stent at various time points (post-manufacture, post-crimping, post simulated delivery, pre and/or post expansion of the stent)

Optical Microscopy

An optical microscope may be used to create and inspect the devices and to empirically survey the coating of the substrate (e.g. coating uniformity). Nanoparticles of the drug and/or the polymer can be seen on the surfaces of the substrate using this analytical method. Following sintering, the coatings can be see using this method to view the coating conformality and for evidence of crystallinity of the drug. The device may thus be evaluated for broken substrate piece or broken device piece and to determine whether such broken substrate penetrated the coating. Coating conformality may be assessed using this technique, including, for example, visualization of contact of the coating to the stent and/or adherence of the coating to the stent at various time points (post-manufacture, post-crimping, post simulated delivery, pre and/or post expansion of the stent)

Example 10: Determination of Secondary Structures Presence of a Biological Agent Raman Spectroscopy FT-Raman or confocal raman microscopy can be employed to determine secondary structure of a biological Agent. For example fitting of the Amide I, II, or III regions of the Raman spectrum can elucidate secondary structures (e.g. alpha-helices, beta-sheets). See, for example, Iconomidou, et al., "Secondary Structure of Chorion Proteins of the Teleosetan Fish Dentex dentex by ATR FR-IR and FT-Raman Spectroscopy" *J. of Structural Biology*, 132, 112-122 (2000); Griebenow, et al., "On Protein Denaturation in Aqueous-Organic Mixtures but Not in Pure Organic Solvents" *J. Am. Chem. Soc.*, Vol. 118, No. 47, 11695-11700 (1996).

Infrared (IR) Spectroscopy for In-Vitro Testing

Infrared spectroscopy, for example FTIR, ATR-IR and micro ATR-IR can be employed to determine secondary structure of a biological Agent. For example fitting of the Amide I, II, of III regions of the infrared spectrum can elucidate secondary structures (e.g. alpha-helices, beta-sheets).

Example 11: Determination of the Microstructure of a Coating on a Medical Device Atomic Force Microscopy (AFM)

AFM is a high resolution surface characterization technique. AFM is used in the art to provide topographical imaging, in addition when employed in Tapping Mode™ can image material and or chemical properties of the surface. Additionally cross-sectioned samples can be analyzed. The technique can be used under ambient, solution, humidified or temperature controlled conditions. Other modes of operation are well known and can be readily employed here by those skilled in the art.

A device as described herein is obtained. AFM is used to determine the microstructure of the coating. A stent as described herein is obtained. AFM may be employed as described in Ranade et al., "Physical characterization of controlled release of paclitaxel from the TAXUS Express2 drug-eluting stent" *J. Biomed. Mater. Res.* 71(4):625-634 (2004) incorporated herein in its entirety by reference.

For example, polymer and drug morphologies, coating composition, and physical structure may be determined using atomic force microscopy (AFM) analysis. A multi-mode AFM (Digital Instruments/Veeco Metrology, Santa Barbara, Calif.) controlled with Nanoscope IIIa and Nano-Scope Extender electronics is used. Samples are examined in the dry state using AFM before elution of the drug (e.g. rapamycin). Samples are also examined at select time points through a elution period (e.g. 48 hours) by using an AFM probe-tip and flow-through stage built to permit analysis of wet samples. The wet samples are examined in the presence of the same elution medium used for in-vitro kinetic drug release analysis (e.g. PBS-Tween20, or 10 mM Tris, 0.4 wt. % SDS, pH 7.4). Saturation of the solution is prevented by frequent exchanges of the release medium with several volumes of fresh medium. TappingMode™ AFM imaging may be used to show topography (a real-space projection of the coating surface microstructure) and phase-angle changes of the AFM over the sample area to contrast differences in the materials properties. The AFM topography images can be three-dimensionally rendered to show the surface of a coated stent, which can show holes or voids of the coating which may occur as the polymer is absorbed and the drug is released from the polymer over time, for example.

Nano X-Ray Computer Tomography

Another technique that may be used to view the physical structure of a device in 3-D is Nano X-Ray Computer Tomography (e.g. such as made by SkyScan), which could be used in an elution test and/or bioabsorbability test, as described herein to show the physical structure of the coating remaining on substrates at each time point, as compared to a scan prior to elution/bioabsorbtion.

The foregoing is illustrative of the present invention, and is not to be construed as limiting thereof. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A coated stent comprising
   a. a stent having a plurality of struts;
   b. a coating having an active agent and a bioabsorbable polymer, wherein the active agent is a macrolide immunosuppressive drug in crystalline form, wherein the active agent remains in crystalline form after being included in the coating;
   wherein said coating is substantially conformal to abluminal, luminal, and sidewall surfaces of the struts of the stent to form a plurality of coated struts and a ratio of an abluminal coating thickness to a luminal coating thickness is at most 90:10.

2. The coated stent of claim 1, wherein a coated strut thickness measured from the abluminal surface of the coated strut to the luminal surface of the coated strut is at most 65-85 microns.

3. The coated stent of claim 1, wherein the ratio of abluminal coating thickness to luminal coating thickness is at least one of: at most 50:50, at most 65:35, at most 70:30, and at most 80:20.

4. The coated stent of claim 1, wherein the ratio of abluminal coating thickness to luminal coating thickness is achieved during coating of the stent without a masking element.

5. The coated stent of claim 1, wherein the ratio of abluminal coating thickness to luminal coating thickness is achieved during coating of the stent without shielding the luminal surfaces.

6. The coated stent of claim 1, wherein the ratio of abluminal coating thickness to luminal coating thickness is achieved during coating of the stent, wherein the stent is in at least one of: a collapsed condition, an expanded condition, and an intermediate condition.

7. The coated stent of claim 1, wherein an average coated strut thickness when measured from the abluminal surface of the coated strut to the luminal surface of the coated strut is at least one of: at most 85 microns and at most 75 microns.

8. A coated medical device comprising
 a. a medical device having first, second, third and fourth surfaces;
 b. a coating having an active agent and a bioabsorbable polymer, wherein the active agent is a macrolide immunosuppressive drug in crystalline form, wherein the active agent remains in crystalline form after being included in the coating;
 wherein said coating is substantially conformal to the first, second, third and fourth surfaces and a ratio of a first surface coating thickness to a second surface coating thickness is at most 90:10.

9. The coated medical device of claim 8, wherein a thickness measured from the coated first surface to the coated second surface is at most 65-85 microns.

10. The coated medical device of claim 8, wherein the ratio of first surface coating thickness to the second surface coating thickness is at least one of: at most 50:50, at most 65:35, at most 70:30, and at most 80:20.

11. The coated medical device of claim 8, wherein the ratio of the first surface coating thickness to the second surface coating thickness is achieved during coating of the medical device without a masking element.

12. The coated medical device of claim 8, wherein the ratio of the first surface coating thickness to the second surface coating thickness is achieved during coating of the medical device without shielding the second surface.

13. The coated medical device of claim 8, wherein the ratio of the first surface coating thickness to the second surface coating thickness is achieved during coating of the medical device, wherein the medical device is in at least one of: a first condition, a second condition and a third condition.

14. The coated medical device of claim 8, wherein an average coated thickness when measured from the first surface to the second surface is at least one of: at most 85 microns and at most 75 microns.

15. A method of coating a stent comprising
 a. depositing at least one bioabsorbable polymer layer on a plurality of struts of the stent;
 b. depositing at least one a macrolide immunosuppressive drug layer on the plurality of struts of the stent, the drug being in crystalline form and remaining in crystalline form after being included in the coating; and
 c. repeating at least one of steps (a) and (b),
 wherein said coating is substantially conformal to abluminal, luminal, and sidewall surfaces of the struts of the stent to form a plurality of coated struts and a ratio of an abluminal coating thickness to a luminal coating thickness is at most 80:20.

16. The method of claim 15, wherein a resultant coated strut thickness measured from the abluminal surface of the coated strut to the luminal surface of the coated strut is at most 65-85 microns.

17. The method of claim 15, wherein the ratio of abluminal coating thickness to luminal coating thickness is at least one of: at most 50:50, at most 65:35, and at most 70:30.

18. The method of claim 15, wherein the ratio of abluminal coating thickness to luminal coating thickness is achieved during coating of the stent without a masking element and without shielding the luminal surfaces.

19. The method of claim 15, wherein the depositing steps are performed when the stent is in at least one of: a collapsed condition, an expanded condition, and an intermediate condition.

20. The method of claim 15, wherein an average coated strut thickness when measured from the abluminal surface of the coated strut to the luminal surface of the coated strut is at least one of: at most 85 microns and at most 75 microns.

* * * * *